United States Patent
Chou et al.

(10) Patent No.: US 11,400,255 B1
(45) Date of Patent: Aug. 2, 2022

(54) ASPIRATION CATHETER SYSTEMS AND METHODS OF USE

(71) Applicant: Route 92 Medical, Inc., San Mateo, CA (US)

(72) Inventors: Tony M. Chou, San Mateo, CA (US);
Scott D. Wilson, San Mateo, CA (US);
Vera Shinsky, San Mateo, CA (US);
Casey Grey, San Mateo, CA (US);
John Miller, San Mateo, CA (US)

(73) Assignee: Route 92 Medical, Inc., San Mateo, CA (US)

( * ) Notice: Subject to any disclaimer, the term of this patent is extended or adjusted under 35 U.S.C. 154(b) by 236 days.

(21) Appl. No.: 16/684,324

(22) Filed: Nov. 14, 2019

Related U.S. Application Data

(60) Provisional application No. 62/885,019, filed on Aug. 9, 2019, provisional application No. 62/768,031, filed on Nov. 15, 2018.

(51) Int. Cl.
*A61M 25/01* (2006.01)
*A61M 25/10* (2013.01)
(Continued)

(52) U.S. Cl.
CPC ........ *A61M 25/01* (2013.01); *A61M 25/0054* (2013.01); *A61M 25/10185* (2013.11);
(Continued)

(58) Field of Classification Search
CPC ............ A61M 1/64; A61M 1/65; A61M 1/71; A61M 1/74; A61M 1/742; A61M 1/743; A61M 1/75; A61M 25/01; A61M 2025/0004; A61M 2025/0006; A61M 2025/0681; A61M 39/06;
(Continued)

(56) References Cited

U.S. PATENT DOCUMENTS

| | | |
|---|---|---|
| 3,612,050 A | 10/1971 | Sheridan |
| 4,946,443 A | 8/1990 | Hauser et al. |

(Continued)

OTHER PUBLICATIONS

"Clot Aspiration Thrombectomy in Acute Ischemic Stroke," (Sep. 23, 2017) *Neupsy Key*, Web. Date accessed Feb. 10, 2020, 12 pages. <URL: https://neupsykey.com/clot-aspiration-thrombectomy-in-acute-ischemic-stroke/>.

(Continued)

*Primary Examiner* — Kami A Bosworth
(74) *Attorney, Agent, or Firm* — Mintz Levin Cohn Ferris Glovsky and Popeo, P.C.

(57) ABSTRACT

A method of performing a medical procedure in a cerebral vessel including advancing a guide sheath into an internal carotid artery; advancing a catheter within a lumen of the guide sheath until a distal end of the catheter is adjacent to an embolus in a cerebral vessel; activating a vacuum source to create a vacuum in a lumen of the catheter; and cyclically controlling the vacuum applied with a valve. The vacuum is cyclically controlled by opening the valve for a first time period, closing the valve for a second time period longer than the first time period, opening the valve for a third time period shorter than the first time period, then closing the valve for a fourth time period greater than the first time period, and repeating for at least 40 cycles.

19 Claims, 27 Drawing Sheets

(51) Int. Cl.
  *A61M 25/00* (2006.01)
  *A61M 25/09* (2006.01)
  *A61M 25/06* (2006.01)
(52) U.S. Cl.
  CPC .............. *A61M 2025/0003* (2013.01); *A61M 2025/0197* (2013.01); *A61M 2025/0681* (2013.01); *A61M 2025/091* (2013.01)
(58) Field of Classification Search
  CPC .... A61M 2039/0613; A61M 2039/062; A61M 2039/0626
  See application file for complete search history.

(56) References Cited

U.S. PATENT DOCUMENTS

| | | | |
|---|---|---|---|
| 6,475,195 | B1 | 11/2002 | Voda |
| 7,736,355 | B2 | 6/2010 | Itou et al. |
| 7,967,789 | B2 | 6/2011 | Solar et al. |
| 8,048,032 | B2 | 11/2011 | Root et al. |
| 8,157,760 | B2 | 4/2012 | Criado et al. |
| 8,715,314 | B1 * | 5/2014 | Janardhan ............... B23K 26/14 606/200 |
| 8,996,095 | B2 | 3/2015 | Anderson et al. |
| 9,144,662 | B2 | 9/2015 | Di Caprio et al. |
| 9,820,761 | B2 | 11/2017 | Garrison et al. |
| 10,531,883 | B1 | 1/2020 | Deville et al. |
| 2003/0233038 | A1 | 12/2003 | Hassett |
| 2007/0208302 | A1 | 9/2007 | Webster et al. |
| 2009/0264865 | A1 | 10/2009 | Kawai |
| 2011/0264133 | A1 | 10/2011 | Hanlon et al. |
| 2012/0116350 | A1 | 5/2012 | Strauss et al. |
| 2013/0035628 | A1 | 2/2013 | Garrison et al. |
| 2013/0281788 | A1 | 10/2013 | Garrison |
| 2014/0371709 | A1 | 12/2014 | Allen et al. |
| 2015/0173782 | A1 | 6/2015 | Garrison et al. |
| 2015/0306286 | A1 * | 10/2015 | Ross ..................... A61M 1/743 604/319 |
| 2016/0058614 | A1 * | 3/2016 | Ross .................. A61F 9/00745 606/107 |
| 2016/0220741 | A1 | 8/2016 | Garrison et al. |
| 2016/0367274 | A1 | 12/2016 | Wallace |
| 2017/0020540 | A1 | 1/2017 | Chou et al. |
| 2017/0238950 | A1 * | 8/2017 | Yang .................. A61B 17/2202 |
| 2017/0274180 | A1 | 9/2017 | Garrison et al. |
| 2017/0281204 | A1 | 10/2017 | Garrison et al. |
| 2017/0368309 | A1 | 12/2017 | Garrison et al. |
| 2018/0028205 | A1 | 2/2018 | Chou et al. |
| 2018/0064453 | A1 | 3/2018 | Garrison et al. |
| 2018/0116684 | A1 | 5/2018 | Garrison et al. |
| 2018/0133436 | A1 | 5/2018 | Garrison et al. |
| 2018/0193042 | A1 | 7/2018 | Wilson et al. |
| 2018/0207399 | A1 | 7/2018 | Chou et al. |
| 2018/0242978 | A1 | 8/2018 | Chou et al. |
| 2018/0361114 | A1 | 12/2018 | Chou et al. |
| 2019/0008534 | A1 | 1/2019 | Garrison et al. |
| 2019/0046218 | A1 | 2/2019 | Garrison et al. |
| 2019/0343445 | A1 * | 11/2019 | Burnett ..................... A61B 5/01 |
| 2019/0351182 | A1 | 11/2019 | Chou et al. |
| 2019/0366042 | A1 | 12/2019 | Garrison et al. |
| 2019/0366043 | A1 | 12/2019 | Garrison et al. |
| 2020/0016369 | A1 | 1/2020 | Garrison et al. |
| 2020/0023160 | A1 | 1/2020 | Chou et al. |
| 2020/0038628 | A1 | 2/2020 | Chou et al. |
| 2020/0046939 | A1 | 2/2020 | Garrison et al. |
| 2020/0046940 | A1 | 2/2020 | Garrison et al. |
| 2020/0164178 | A1 | 5/2020 | Garrison et al. |
| 2020/0187965 | A1 | 6/2020 | Garrison et al. |
| 2020/0215306 | A1 | 7/2020 | Garrison et al. |

OTHER PUBLICATIONS

Arslanian, R., M. Gounis, and J. Chueh. "Pump or Syringe? Evaluation of Aspiration Efficacy with Neurovascular Catheters," (Oral Presentation, SNIS 2018), 2 pages. Web. Date accessed Feb. 10, 2020.
Farooq, Vasim et al. "Forward and Back Aspiration during ST-Elevation Myocardial Infarction: a Feasibility Study." *EuroIntervention*, vol. 11, No. 14, 2016, pp. 1639-1648.
Farooq, Vasim et al. "The Use of a Guide Catheter Extension System as an Aid During Transradial Percutaneous Coronary Intervention of Coronary Artery Bypass Grafts." *Catheterization and Cardiovascular Interventions*, vol. 78, No. 6, 2011, pp. 847-863.
Kallmes, D.F. et al. (Nov. 2018, e-published Jun. 15, 2018). "Let's -ectomize thrombectomy, shall we?" *J NeuroIntervent Surg* 10(11):1031-1032. Web. Date accessed Nov. 15, 2018.
Kayan, Y. and J. Delgado, "Neurointerventional Treatment of Acute Stroke in 2015 at Abbott Northwestern Hospital," (Nov. 16, 2015). 75 pages. (https://www.slideshare.net/AllinaHealth/neurointerventional-treatment-of-acute-stroke-in-2015-at-abbott-northwestern-hospital).
Patel, Tejas et al. (2014) "Balloon-Assisted Tracking: A Must-Know Technique to Overcome Difficult Anatomy During Transradial Approach," *Catheter Cardiovasc. Interv.* 83(2):211-220.
Rai, A.T., et al. (2013, first published Apr. 4, 2012). "Cerebrovascular geometry in the anterior circulation: an analysis of diameter, length and the vessel taper," *Journal of NeuroInterventional Surgery* 5:371-375. Web. Date accessed Feb. 13, 2020.
Simon, S. et al. (2014, e-published Nov. 14, 2013) "Exploring the efficacy of cyclic vs static aspiration in a cerebral thrombectomy model: an initial proof of concept study." *J. NeuroIntervent Surg* 6: 677-683. Web. Date accessed Oct. 18, 2017.
Spiotta, A. et al. (Feb. 2016). "ADAPT: A Direct Aspiration First Pass Technique." *Endovascular Today* 15(2):68-70.
Stys, Adam T. et al. "A Novel Application of GuideLiner Catheter for Thrombectomy in Acute Myocardial Infarction: A Case Series." *Journal of Invasive Cardiology*, vol. 25, No. 11, 2013, pp. E254-E259. 6 pages. (http://www.invasivecardiology.com/issue/4284).
Turk, Aquilla S et al. (2014, e-published Apr. 27, 2013) "Initial clinical experience with the ADAPT technique: A direct aspiration first pass technique for stroke thrombectomy." *J NeuroIntervent Surg* 2014;6:231-237. doi:10.1136/neurintsurg-2013-010713. Web. Accessed Sep. 26, 2018.
U.S. Appl. No. 13/921,165, filed Jun. 18, 2013, US 2013-0281788.
U.S. Appl. No. 15/625,135, filed Jun. 16, 2017, US 2017-0281204.
U.S. Appl. No. 15/699,401, filed Sep. 8, 2017, US 2017-0368309.
U.S. Appl. No. 15/727,373, filed Oct. 6, 2017, US 2018-0028205.
U.S. Appl. No. 15/747,089, filed Jan. 23, 2018, US 2018-0242978.
U.S. Appl. No. 15/866,012, filed Jan. 9, 2018, US 2018-0193042.
U.S. Appl. No. 15/875,214, filed Jan. 19, 2018, US 2018-0361114.
U.S. Appl. No. 15/875,342, filed Jan. 19, 2018, US 2018-0207399.
U.S. Appl. No. 16/117,741, filed Aug. 30, 2018, US 2019-0008534.
U.S. Appl. No. 16/117,753, filed Aug. 30, 2018, US 2019-0046218.
U.S. Appl. No. 16/414,532, filed May 16, 2019, US 2019-0351182.
U.S. Appl. No. 16/530,845, filed Aug. 2, 2019, US 2020-0023160.
U.S. Appl. No. 16/543,215, filed Aug. 16, 2019, US 2019-0366042.
U.S. Appl. No. 16/543,226, filed Aug. 16, 2019, US 2019-0366043.
U.S. Appl. No. 16/584,220, filed Sep. 26, 2019, US 2020-0016369.
U.S. Appl. No. 16/584,351, filed Sep. 26, 2019, US 2020-0038628.
U.S. Appl. No. 16/596,531, filed Oct. 8, 2019, US 2020-0046939.
U.S. Appl. No. 16/596,535, filed Oct. 8, 2019, US 2020-0046940.
PCT/US2019/032694, May 16, 2019, WO 2019/222518.

* cited by examiner

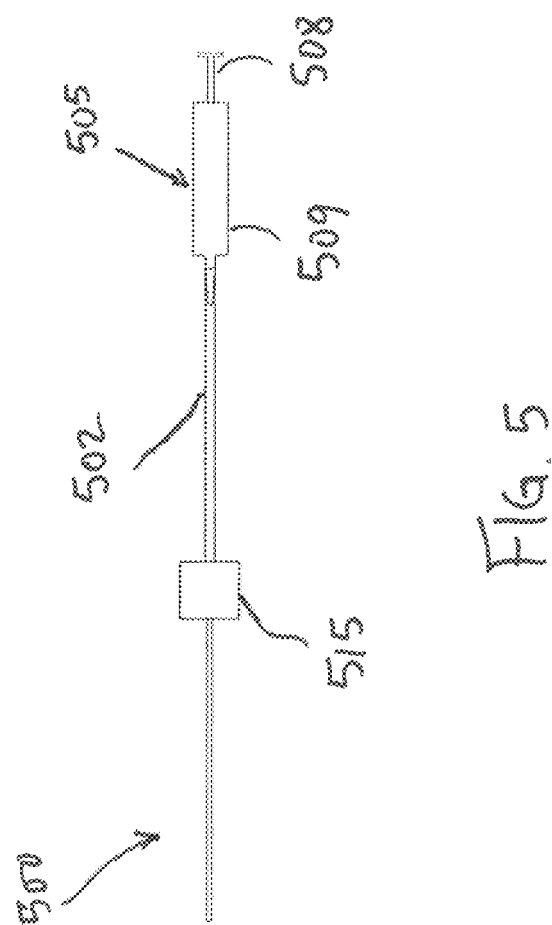

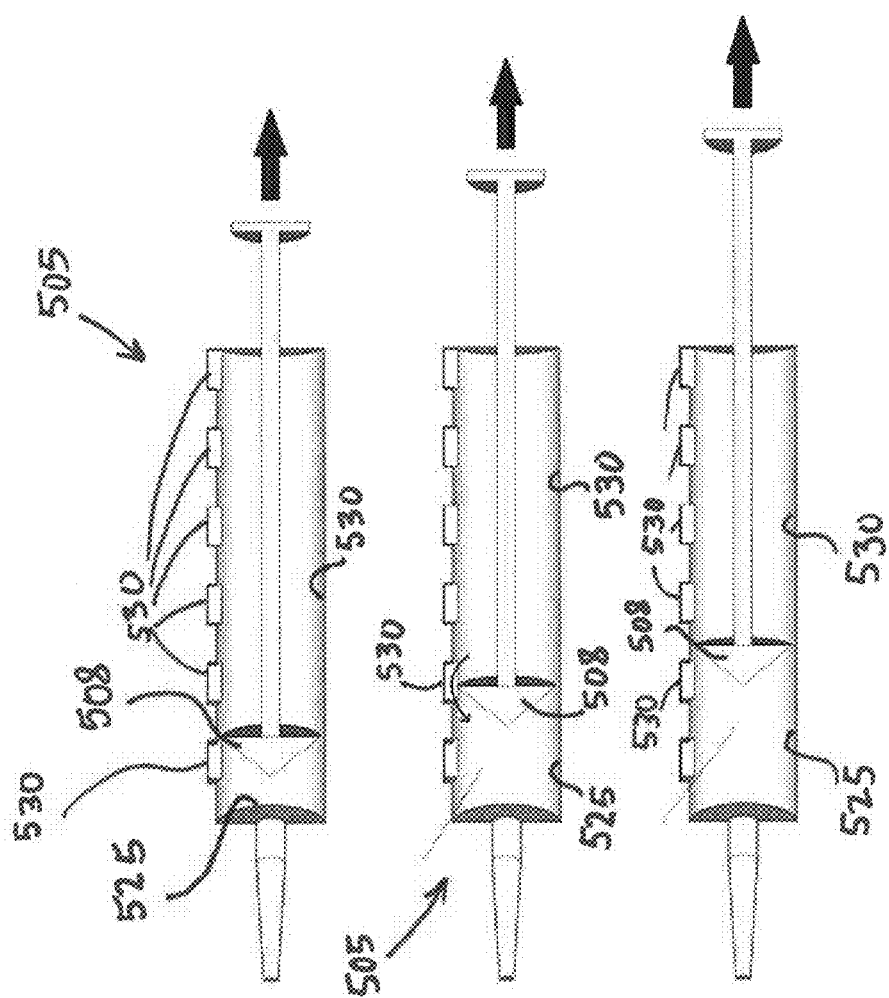

ASPIRATION CATHETER SYSTEMS AND METHODS OF USE

CROSS-REFERENCE TO RELATED APPLICATIONS

This application claims the benefit of priority under 35 U.S.C. § 119(e) to U.S. Provisional Patent Application Serial Nos. 62/768,031, filed Nov. 15, 2018, and 62/885,019, filed Aug. 9, 2019. The disclosures of the provisional applications are incorporated by reference in their entireties.

FIELD

The present technology relates generally to medical devices and methods, and more particularly, to aspiration catheter systems and their methods of use.

BACKGROUND

Acute ischemic stroke (AIS) usually occurs when an artery to the brain is occluded, preventing delivery of fresh oxygenated blood from the heart and lungs to the brain. These occlusions are typically caused by a thrombus or an embolus lodging in the artery and blocking the artery that feeds a territory of brain tissue. If an artery is blocked, ischemia injury follows, and brain cells may stop working. Furthermore, if the artery remains blocked for more than a few minutes, the brain cells may die, leading to permanent neurological deficit or death. Therefore, immediate treatment is critical.

Two principal therapies are employed for treating ischemic stroke: thrombolytic therapy and endovascular treatment. The most common treatment used to reestablish flow or re-perfuse the stroke territory is the use of intravenous (IV) thrombolytic therapy. The timeframe to enact thrombolytic therapy is within 3 hours of symptom onset for IV infusion (4.5 hours in selected patients) or within 6 hours for site-directed intra-arterial infusion. Instituting therapy after this window has no proven benefit and may expose the patient to greater risk of bleeding due to the thrombolytic effect. Endovascular treatment most commonly uses a set of tools to mechanically remove the embolus, with or without the use of thrombolytic therapy.

The gamut of endovascular treatments include mechanical embolectomy, which utilizes a retrievable structure, e.g., a coil-tipped retrievable stent (also known as a stent retriever or a STENTRIEVER), a woven wire stent, or a laser cut stent with struts that can be opened within a clot in the cerebral anatomy to engage the clot with the stent struts, create a channel in the emboli to restore a certain amount of blood flow, and to subsequently retrieve the retrievable structure by pulling it out of the anatomy, along with aspiration techniques. Other endovascular techniques to mechanically remove AIS-associated embolus include Manual Aspiration Thrombectomy (MAT) (also known as the "ADAPT" technique). ADAPT/MAT is an endovascular procedure where large bore catheters are inserted through the transfemoral artery and maneuvered through complex anatomy to the level of the embolus, which may be in the extracranial carotids, vertebral arteries, or intracranial arteries. Aspiration techniques may be used to remove the embolus through the large bore catheters. Another endovascular procedure is STENTRIEVER-Mediated Manual Aspiration Thrombectomy (SMAT) (similar to the STENTRIEVER-assisted "Solumbra" technique). SMAT, like MAT, involves accessing the embolus through the transfemoral artery. After access is achieved, however, a retrievable structure is utilized to pull the embolus back into a large bore catheter.

To access the cerebral anatomy, guide catheters or guide sheaths are used to guide interventional devices to the target anatomy from an arterial access site, typically the femoral artery. The length of the guide is determined by the distance between the access site and the desired location of the guide distal tip. Interventional devices such as guidewires, microcatheters, and intermediate catheters used for sub-selective guides and aspiration, are inserted through the guide and advanced to the target site. Often, devices are used in a co-axial fashion, namely, a guidewire inside a microcatheter inside an intermediate catheter is advanced as an assembly to the target site in a stepwise fashion with the inner, most atraumatic elements, advancing distally first and providing support for advancement of the outer elements. The length of each element of the coaxial assemblage takes into account the length of the guide, the length of proximal connectors on the catheters, and the length needed to extend from the distal end.

Typical tri-axial systems such as for aspiration or delivery of stent retrievers and other interventional devices require overlapped series of catheters, each with their own rotating hemostatic valves (RHV) on the proximal end. For example, a guidewire can be inserted through a Penumbra Velocity microcatheter having a first proximal RHV, which can be inserted through a Penumbra ACE68 having a second proximal RHV, which can be inserted through a Penumbra NeuronMAX 088 access catheter having a third proximal RHV positioned in the high carotid via a femoral introducer. Maintaining the coaxial relationships between these catheters can be technically challenging. The three RHVs must be constantly adjusted with two hands or, more commonly, four hands (i.e. two operators). Further, the working area of typical tri-axial systems for aspiration and/or intracranial device delivery can require working area of 3-5 feet at the base of the operating table.

The time required to access the site of the occlusion and restore, even partially, flow to the vessel is crucial in determining a successful outcome of such procedures. Similarly, the occurrence of distal emboli during the procedure and the potentially negative neurologic effect and procedural complications such as perforation and intracerebral hemorrhage are limits to success of the procedure. There is a need for a system of devices and methods that allow for rapid access, optimized catheter aspiration and treatment to fully restore flow to the blocked cerebral vessel.

SUMMARY

In an aspect, describes is a method of performing a medical procedure in a cerebral vessel. The method includes inserting a catheter system into a blood vessel. The catheter system includes a guide sheath having a distal end, a proximal end, a lumen extending between the distal end and the proximal end, and a rotating hemostatic valve disposed on the proximal end. The catheter system includes a catheter having a proximal end, a distal end, and a lumen. An outer diameter of the catheter is sized to be slidably disposed within the lumen of the guide sheath through the rotating hemostatic valve. The catheter system includes a vacuum source configured to be placed in fluid communication with the lumen extending through the catheter; and a valve positioned between the vacuum source and the catheter. The method includes advancing the guide sheath into the internal carotid artery; advancing the catheter within the lumen of the guide sheath until the distal end of the catheter is adjacent to an embolus in the cerebral vessel; activating the vacuum source to create a vacuum in the lumen of the catheter; and cyclically controlling the vacuum applied with the valve. The vacuum is cyclically controlled by opening the valve for between about 40 to 50 ms, closing the valve for between about 100 to 150 ms, opening the valve for between about 5 to 10 ms, then closing the valve for between about 100 to 150 ms, repeating for about 40 to 80 cycles.

The method can further include applying static aspiration forces for between about 5 to 10 seconds to reestablish maximal aspiration pressure after completing the cycles. The pump can include a programmable pump motor controller. The method can further include providing a pressure differential between the vacuum source, the distal end of the catheter, and an external environment using the valve to control patency. The method can further include temporarily closing the valve to the external environment causing the vacuum source to create a vacuum at the distal end of the catheter, and subsequently opening the valve to the external environment diminishing the vacuum applied at the distal end of the catheter. The valve can be a three-way valve. The valve can be pneumatic, electromechanical, or mechanical. The valve can be a pneumatic valve located on a vacuum line near a proximal section bridging a proximal canister and the catheter system. The valve can be located inside, attached to, or near an outlet from the proximal vacuum canister. The valve can be attached to the proximal end of the guide sheath. The valve can be a plurality of valves serially coupled in fluid communication. Each of the serially coupled valves can be controlled or programmed to cycle at different frequencies. The method can further include electronically controlling the valve with a microcontroller relay system to create a cyclic pressure environment at the distal end of the catheter. The microcontroller relay system can alternately open and close a connection between the catheter lumen and a second environment. The second environment can include a controlled pressure chamber or ambient atmosphere.

In an interrelated aspect, disclosed is a method of performing a medical procedure in a cerebral vessel of a patient that includes assembling a first coaxial catheter system. The first coaxial catheter system includes a first catheter; a first delivery element, and a second catheter. The first catheter includes a first catheter portion having a lumen, a proximal opening into the lumen, a distal opening from the lumen, and a distal end. The first catheter also includes a first proximal extension coupled to and extending proximally from the first catheter portion. The first proximal extension is less flexible than the first catheter portion. The first delivery element has a flexible, elongate body and a soft, tapered distal tip portion. At least a portion of the elongate body positioned within the lumen of the first catheter portion and the tapered distal tip portion extends distal to the distal end of the first catheter portion. The second catheter includes a second catheter portion having a lumen, a proximal opening into the lumen, a distal opening from the lumen, and a distal end. The second catheter also includes a second proximal extension coupled to and extending proximally from the second catheter portion. The second proximal extension is less flexible than the second catheter portion. The first delivery element is positioned within the lumen of the first catheter portion and the first catheter is positioned within the single lumen of the second catheter when the first coaxial catheter system is assembled. The method further includes advancing the assembled first coaxial catheter system together towards a location near a proximal face of an embolus within a cerebral blood vessel after the distal end of the first catheter portion is located distal to the petrous portion of the internal carotid artery. The method further includes withdrawing the first delivery element proximally from the lumen of the first catheter portion while the distal end is held in position near the proximal face of the embolus. The method further includes activating a vacuum source configured to be placed in fluid communication with the lumen extending through the first coaxial catheter system to create a vacuum in the lumen of the assembled first coaxial catheter system. A valve is positioned between the vacuum source and the first coaxial catheter system. The method further includes cyclically controlling the vacuum applied. The vacuum is cyclically controlled by opening the valve for between about 40 to 50 ms, closing the valve for between about 100 to 150 ms, opening the valve for between about 5 to 10 ms, then closing the valve for between about 100 to 150 ms, repeating for about 40 to 80 cycles. The method further includes advancing the second catheter over the first catheter while anchoring the distal end of the first catheter portion onto the occlusion via the cyclic aspiration.

In some variations, one or more of the following can optionally be included in any feasible combination in the above methods, apparatus, devices, and systems. More details are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally, the figures are not to scale in absolute terms or comparatively, but are intended to be illustrative. Also, relative placement of features and elements may be modified for the purpose of illustrative clarity.

FIG. 5 is a schematic view of another implementation of a cyclic aspiration system incorporating a standard syringe as the vacuum source;

FIGS. 6A-6D are schematic views of a cyclic aspiration system incorporating a syringe as a vacuum source that is configured to provide cyclic aspiration directly without any valve;

It should be appreciated that the drawings are for example only and are not meant to be to scale. It is to be understood that devices described herein may include features not necessarily depicted in each figure.

DETAILED DESCRIPTION

Figure 1A:
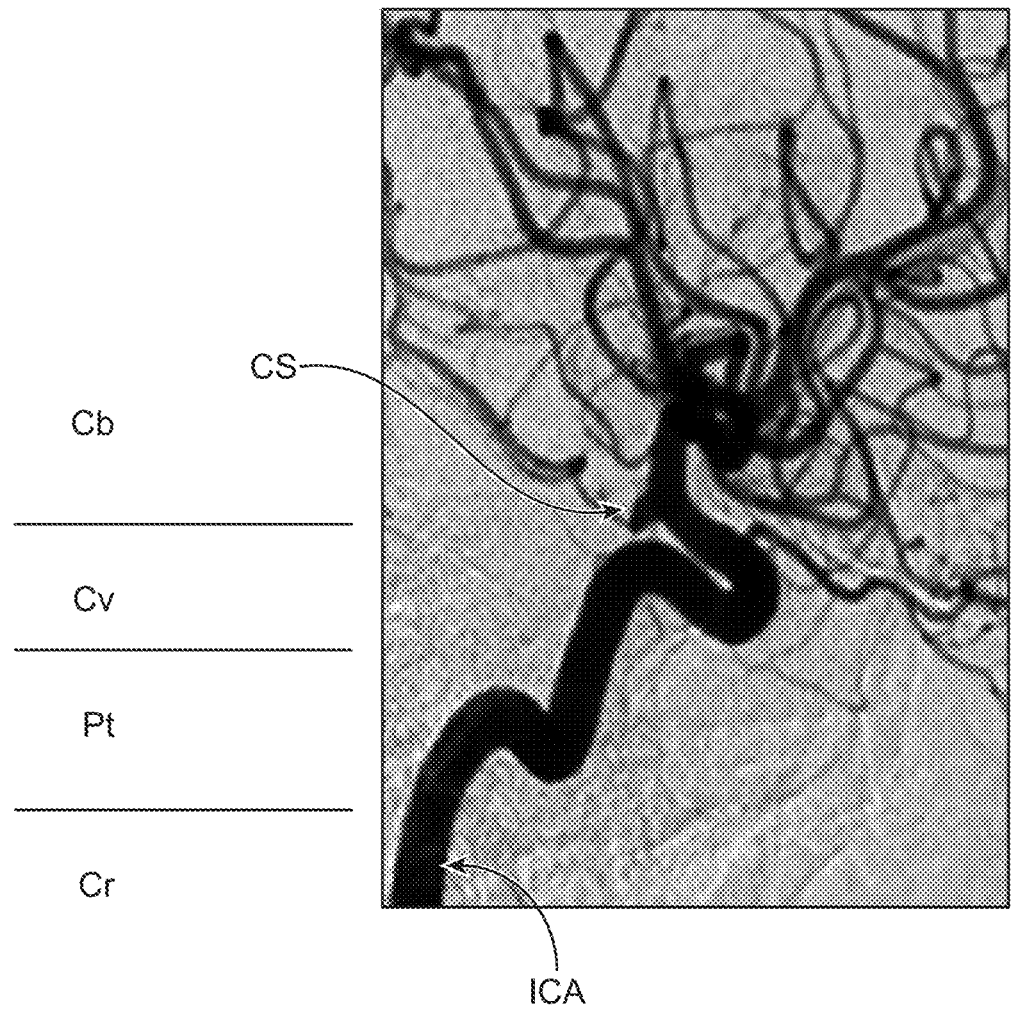
FIGS. 1A-1B illustrate the course of the terminal internal carotid artery through to the cerebral vasculature.

Navigating the carotid anatomy in order to treat various neurovascular pathologies at the level of the cerebral arteries, such as acute ischemic stroke (AIS), requires catheter systems having superior flexibility and deliverability. The internal carotid artery (ICA) arises from the bifurcation of the common carotid artery (CCA) at the level of the intervertebral disc between C3 and C4 vertebrae. As shown in FIG. 1A, the course of the ICA is divided into four parts—cervical Cr, petrous Pt, cavernous Cv and cerebral Cb parts. In the anterior circulation, the consistent tortuous terminal carotid is locked into its position by bony elements. The cervical carotid Cr enters the petrous bone and is locked into a set of turns as it is encased in bone. The cavernous carotid is an artery that passes through a venous bed, the cavernous sinus, and while flexible, is locked as it exits the cavernous sinus by another bony element, which surrounds and fixes the entry into the cranial cavity. Because of these bony points of fixation, the petrous and cavernous carotid (Pt and Cv) and above are relatively consistent in their tortuosity. The carotid siphon CS is an S-shaped part of the terminal ICA. The carotid siphon CS begins at the posterior bend of the cavernous ICA and ends at the ICA bifurcation into the anterior cerebral artery ACA and middle cerebral artery MCA. The ophthalmic artery arises from the cerebral ICA, which represents a common point of catheter hang-up in accessing the anterior circulation. The MCA is initially defined by a single M1 segment and then further bifurcates in two or three M2 segments and then further arborizes to create M3 segments. These points of catheter hang-up can significantly increase the amount of time needed to restore blood perfusion to the brain, which in the treatment of AIS is a disadvantage with severe consequences.

With advancing age, the large vessels often enlarge and lengthen. Fixed proximally and distally, the cervical internal carotid artery often becomes tortuous with age. The common carotid artery CCA is relatively fixed in the thoracic cavity as it exits into the cervical area by the clavicle. The external and internal carotid arteries ECA, ICA are not fixed relative to the common carotid artery CCA, and thus they develop tortuosity with advancing age with lengthening of the entire carotid system. This can cause them to elongate and develop kinks and tortuosity or, in worst case, a complete loop or so-called "cervical loop". If catheters used to cross these kinked or curved areas are too stiff or inflexible, these areas can undergo a straightening that can cause the vessel to wrap around or "barbershop pole" causing focused kinking and folding of the vessel. These sorts of extreme tortuosity also can significantly increase the amount of time needed to restore blood perfusion to the brain, particularly in the aging population. In certain circumstances, the twisting of vessels upon themselves or if the untwisted artery is kinked, normal antegrade flow may be reduced to a standstill creating ischemia. Managing the unkinking or unlooping the vessels such as the cervical ICA can also increase the time it takes to perform a procedure.

A major drawback of current catheter systems for stroke intervention procedures is the amount of time required to restore blood perfusion to the brain, including the time it takes to access the occlusive site or sites in the cerebral artery and the time it takes to completely remove the occlusion in the artery. Because it is often the case that more than one attempt must be made to completely remove the occlusion, reducing the number of attempts as well as reducing the time required to exchange devices for additional attempts is an important factor in minimizing the overall time. Additionally, each attempt is associated with potential procedural risk due to device advancement in the delicate cerebral vasculature. Another limitation is the need for multiple operators to deliver and effectively manipulate long tri-axial systems with multiple RHVs typically used with conventional guide and distal access catheters.

Described herein are catheter systems and methods for treating various neurovascular pathologies, such as acute ischemic stroke (AIS). The systems described herein provide quick and simple single-operator access to distal target anatomy, in particular tortuous anatomy of the cerebral vasculature at a single point of manipulation. The medical methods, devices and systems described herein allow for navigating complex, tortuous anatomy to perform rapid and safe aspiration and removal of cerebral occlusions for the treatment of acute ischemic stroke. The medical methods, devices and systems described herein can also be used to deliver intracranial medical devices, with or without aspiration for the removal of cerebral occlusions in the treatment of acute ischemic stroke. The systems described herein can be particularly useful for the treatment of AIS whether a user intends to perform aspiration alone or as a frontline treatment for AIS. Further, the extreme flexibility and deliverability of the distal access catheter systems described herein allow the catheters to take the shape of the tortuous anatomy rather than exert straightening forces that alter the natural vascular architecture. The distal access catheter systems described herein can pass through tortuous loops while maintaining the natural curves of the anatomy therein decreasing the risk of vessel straightening. The distal access catheter systems described herein can thereby create a safe conduit through the neurovasculature maintaining the natural tortuosity of the anatomy for other catheters to traverse (e.g. larger bore aspiration catheters). The distal access catheter systems described herein can be used to guide the catheters described herein and other commercially available catheters, such as full-length catheters, through the neurovasculature, and in some instances, allow a user to advance a catheter through the anatomy using the distal access catheter where it could not be previously advanced without the distal access catheter.

The devices, systems, and methods of use described herein are related to and can be used in combination and in the alternative with the devices, systems, and methods of use described in U.S. Publication No. 2013/0035628, filed Aug. 3, 2012; U.S. Publication No. 2015/0173782, filed Dec. 19, 2014; and U.S. Publication No. 2016/0220741, filed Feb. 4, 2016. The disclosures of each of these publications are incorporated by reference herein in their entireties.

While some implementations are described herein with specific regard to accessing a neurovascular anatomy for application of aspiration, the systems and methods described herein should not be limited to this and may also be applicable to other uses. For example, the catheter systems described herein may be used to deliver working devices to a target vessel of a coronary anatomy or other vasculature anatomy. Where the phrase "distal access catheter" or "aspiration catheter" is used herein that the catheter can be used for aspiration, the delivery of fluids to a treatment site or as a support catheter, or distal access providing a conduit that facilitates and guides the delivery or exchange of other devices such as a guidewire or interventional devices such as stent retrievers. Alternatively, the access systems described herein may also be useful for access to other parts of the body outside the vasculature. Similarly, where the working device is described as being an expandable cerebral treatment device, such as, but not limited to, a stent retriever or a self-expanding stent, it is contemplated that other interventional devices can be delivered using the access systems described herein.

Figure 2A:
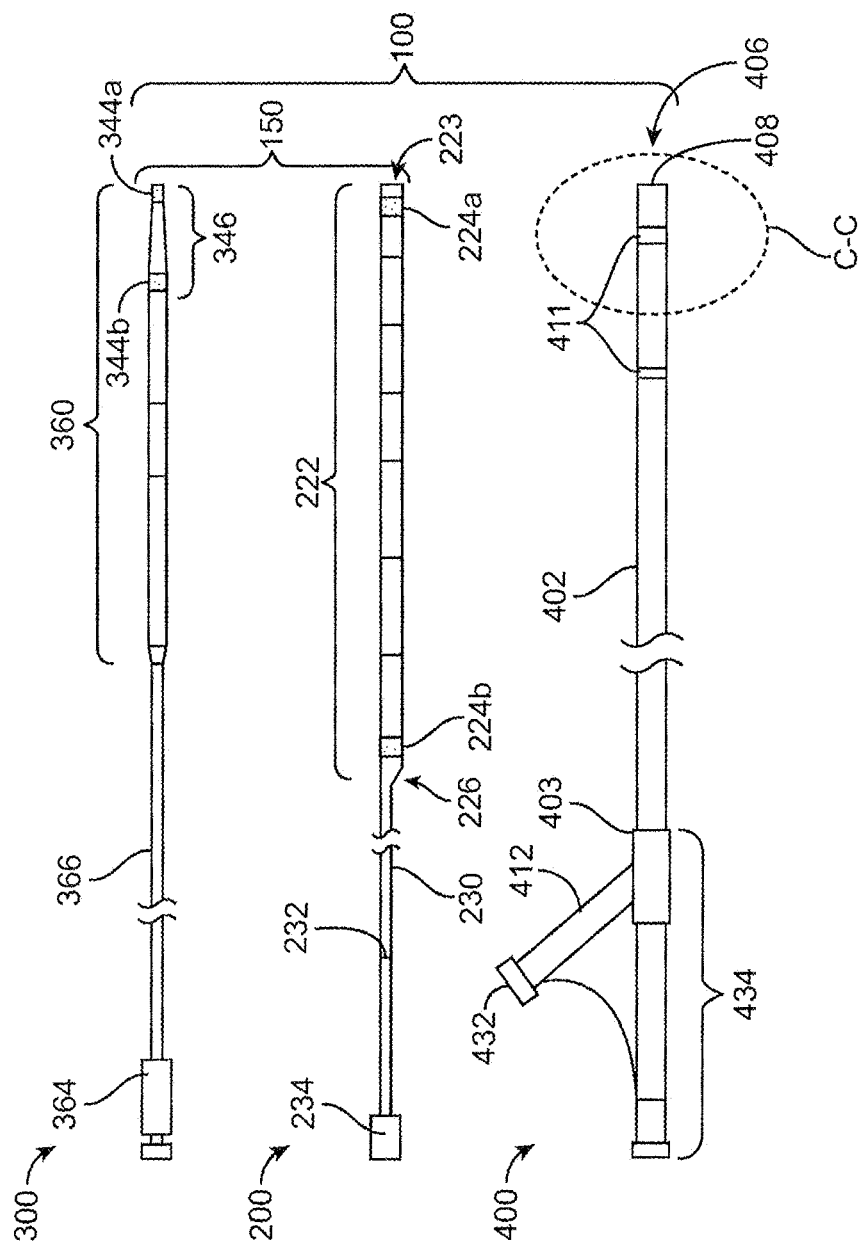
FIG. 2A is an exploded view of an implementation of an aspiration catheter system.
Figure 2B:
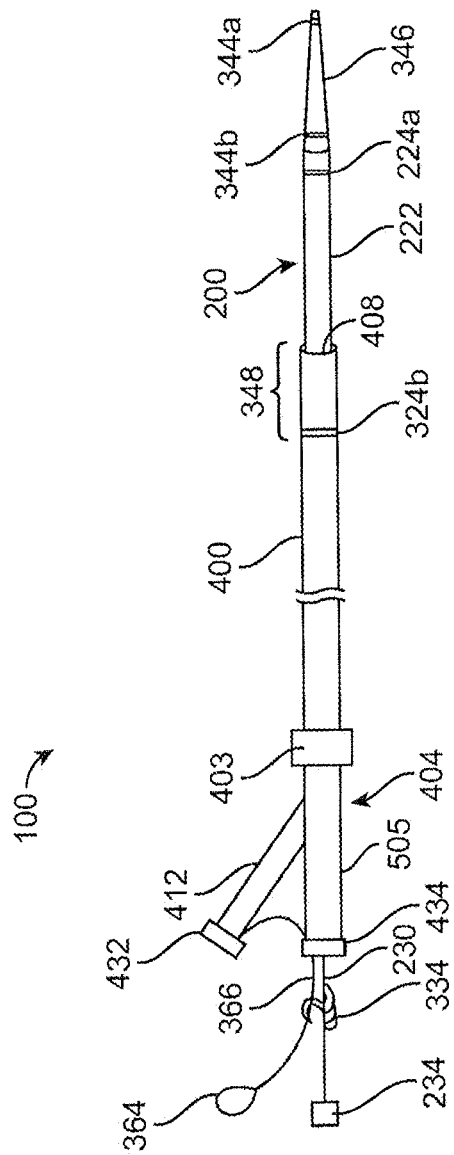
FIG. 2B is an assembled view of the aspiration catheter system of FIG. 2A.

Referring now to the drawings, FIGS. 2A-2B illustrate a system 100 including devices for accessing and removing a cerebral occlusion to treat acute ischemic stroke. The system 100 can be a single operator system such that each of the components and systems can be delivered and used together by one operator through a single point of manipulation requiring minimal hand movements. As will be described in more detail below, all wire and catheter manipulations can occur at or in close proximity to a single rotating hemostatic valve (RHV) 434 or a multi-head RHV or through one or more RHVs co-located on the same device. The system 100 can include one or more catheter delivery systems 150, each having a catheter 200 and a catheter advancement element 300. The catheter delivery system 150 is configured to be advanced through an access guide sheath 400. The catheter 200 is configured to be received through the guide sheath 400 and is designed to have exceptional deliverability. The catheter 200 can be a spined, distal access catheter co-axial with a lumen of the guide sheath 400 thereby providing a step-up in inner diameter within the conduit. The catheter 200 can be delivered using a catheter advancement element 300 inserted through a lumen 223 of the catheter 200. The system 100 can be a distal access system that can create a variable length from point of entry at the percutaneous arteriotomy (e.g. the femoral artery or other point of entry) to the target control point of the distal catheter. Conventional distal access systems for stroke intervention typically include a long guide sheath or guide catheter placed through a shorter "introducer" sheath (e.g. 11-30 cm in length) at the groin. The long guide sheath is typically positioned in the ICA to support neurovascular interventions including stroke embolectomy (sometimes referred to as "thrombectomy"). For added support, these can be advanced up to the bony terminal petrous and rarely into the cavernous or clinoid or supraclinoid terminal ICA when possible. To reach targets in the M1 or M2 distribution for ADAPT/MAT or Solumbra/SMAT approaches, an additional catheter may be inserted through the long guide catheter. These catheters are typically large-bore aspiration catheters that can be, for example 130 cm in length or longer. As will be described in more detail below, the distal access systems 100 described herein can be shorter, for example, only 115 cm in length when taken as a system as measured from the access point, typically the common femoral artery. Additionally, the single operator can use the systems described herein by inserting them through a single rotating hemostatic valve (RHV) 434 on the guide sheath 400 or more than one RHV co-located in the same device such as a dual-headed RHV. Thus, what was once a two-person procedure can be a one-person procedure. Using current commercially available catheters and guide sheaths requires the physician to properly select the appropriate length of both the guide sheath and the catheter such that the guide sheath can be advanced into the ICA a sufficient distance to provide support for the catheter disposed within the lumen of the guide sheath to reach the M1 or M2. However, as described above, anatomy of each person can vary and vessels may lengthen and/or straighten when a guide sheath and/or catheter are disposed within them. In practice, a physician may find that the length of guide sheath that they selected may be too short and cannot be advanced into the ICA sufficiently to provide support. Conversely, the selected guide sheath may be too long, therefore extending outside the patient too much, such that when the catheter is disposed within the lumen of the guide sheath, the hub of the catheter touches the RHV of the guide sheath before the distal end of the catheter can be placed at the M1 or M2. If this occurs, the physician would need to either replace the guide sheath with a shorter guide sheath or use a longer catheter, if a longer catheter is available. Either option adds significant time to the procedure as well as added costs of opened but un-used products. The catheter 200 eliminates the sizing problem described above. The physician does not need to guess what length of catheter to use. Instead, the physician can advance and retract catheter 200 within the guide sheath to reach the M1 or M2. A portion of the luminal portion 222 can remain within the lumen of the guide sheath. Aspiration can be performed or other cerebral treatment devices can be delivered to the desired location. The catheter advancement element 300 may be first advanced past the ophthalmic take-off, and then the catheter may be advanced over the catheter advancement element 300. The tapered tip of the catheter advancement element 300 provides a smooth transition to easily pass beyond the ophthalmic take-off without hanging up at the bifurcation of the ophthalmic and carotid arteries.

Each of the various components of the various systems will now be described in more detail.

Access Guide Sheath

Again, with respect to FIGS. 2A-2D, the distal access system 100 can include an access guide sheath 400 having a body 402 through which a working lumen extends from a proximal hemostasis valve 434 coupled to a proximal end region 403 of the body 402 to a distal opening 408 of a distal end region. The working lumen is configured to receive the catheter 200 therethrough such that a distal end of the catheter 200 can extend beyond a distal end of the sheath 400 through the distal opening 408. The guide sheath 400 can be used to deliver the catheters described herein as well as any of a variety of working devices known in the art. For example, the working devices can be configured to provide thrombotic treatments and can include large-bore catheters, aspiration embolectomy (or thrombectomy), advanced catheters, wires, balloons, retrievable structures such as coil-tipped retrievable stents "stent retriever". The guide sheath 400 in combination with the catheter 200 can be used to apply distal aspiration as will be described in more detail below.

The guide sheath 400 can be any of a variety of commercially available guide sheaths. For example, the guide sheath 400 can have an ID between 0.087"-0.089" such as the Cook SHUTTLE 6F (Cook Medical, Inc., Bloomington, Ind.), Terumo DESTINATION 6F (Terumo Europe NV), Cordis VISTA BRITE TIP (Cordis Corp., Hialeah, Fla.), and Penumbra NEURON MAX 088 (Penumbra, Inc., Alameda, Calif.), Stryker Infinity (Stryker Neurovascular, Fremont, Calif.) or comparable commercially available guiding sheath. Generally, sheath sizes are described herein using the French (F) scale. For example, where a sheath is described as being 6 French, the inner diameter of that sheath is able to receive a catheter having a 6F outer diameter, which is about 1.98 mm or 0.078". A catheter may be described herein as having a particular size in French to refer to the compatibility of its inner diameter to receive an outer diameter of another catheter. A catheter may also be described herein as having a particular size in French to refer to its outer diameter being compatible with another catheter having a particular inner diameter.

The guide sheath 400 can be a variety of sizes to accept various working devices, such as catheter 200, and can be accommodated to the operator's preference. The working lumen of the guide sheath 400 can be sized to receive its respective catheter 200 in a sliding fit. Generally, it is desirable to minimize the overall size of the vessel insertion site by limiting the outer diameter of the guide sheath 400 to under 0.122". It is also desirable to select corresponding outer and inner diameters to provide a good sliding fit between the catheter 200 and the guide sheath 400. The working lumen of the guide sheath may have an inner diameter that is at least 0.001" larger than a maximum outer diameter of any catheter 200 it is intended to receive, particularly if the catheter 200 is to be used for aspiration. The working lumen can have an inner diameter sized to accommodate at least 6 French catheters (1.98 mm or 0.078"), or at least 6.3 French catheters (2.079 mm or 0.082" OD), or at least 7 French (2.31 mm or 0.091" OD) catheters or 8 French (2.64 mm or 0.104" OD) or larger catheters. The inner diameter of the guide sheath 400, however, may be smaller or larger to be compatible with other catheter sizes. Regardless of the length and inner diameter, the guide sheath 400 is resistant to kinking during distal advancement through the vessels.

The aspiration catheters described herein can have an ID of between 0.054" to 0.088". If the catheter 200 has a 0.088" inner diameter and have a maximum outer diameter of between 0.105" and 0.107". The guide sheath 400 can, in turn, have a working lumen with an inner diameter that is between 0.106" and 0.108". Generally, the difference or clearance between the maximum outer diameter of the catheter 200 and the inner diameter of the guide sheath 400 is less than about 0.002", for example between 0.001" up to 0.002". The region of low clearance between the maximum outer diameter of the catheter 200 and the inner diameter of the guide sheath 400 can be limited to a localized region. Meaning, the low clearance fit between the two can extend only a fraction of a cylindrical length of the catheter 200 and the sheath 400. Thus, the OD-ID difference between the catheter 200 and the guide sheath 400 can be greater than or equal to 0.002" along a first cylindrical length of where the two devices overlap during use and below 0.002" along a different cylindrical length of the overlap, thereby providing a localized region of low clearance within the overlap. This allows for a convenient relative slidability and sufficient sealing when placed under aspiration pressure as will be described in more detail below. For example, a distal region of the guide sheath 400 can have a first inner diameter at a distal end region and a second, different inner diameter at a proximal end region such that the low clearance of the sliding fit with the catheter 200 varies along its length. In some implementations, the catheter 200 has a first outer diameter at a distal end region and a second, larger outer diameter at a proximal end region. The second, larger outer diameter can be less than 0.002" the inner diameter of the sheath 400 and the first outer diameter greater than 0.002" the inner diameter of the sheath 400. The provides a tighter overall fit between the guide sheath 400 and the proximal end region of the catheter 200 at the location of this second, larger outer diameter.

Again, with respect to FIGS. 2A-2D, the sheath body 402 can extend from a proximal furcation or rotating hemostatic valve (RHV) 434 at a proximal end region 403 to a tip 406 at a distal end of the body 402. The proximal RHV 434 may include one or more lumens molded into a connector body to connect to the working lumen of the body 402 of the guide sheath 400. The working lumen can receive the catheter 200 and/or any of a variety of working devices for delivery to a target anatomy. The RHV 434 can be constructed of thick-walled polymer tubing or reinforced polymer tubing. The RHV 434 allows for the introduction of devices through the guide sheath 400 into the vasculature, while preventing or minimizing blood loss and preventing air introduction into the guide sheath 400. The RHV 434 can be integral to the guide sheath 400 or the guide sheath 400 can terminate on a proximal end in a female Luer adaptor to which a separate hemostasis valve component, such as a passive seal valve, a Tuohy-Borst valve or RHV may be attached. The RHV 434 can have an adjustable opening that is open large enough to allow removal of devices that have adherent clot on the tip without causing the clot to dislodge at the RHV 434 during removal. Alternately, the RHV 434 can be removable such as when a device is being removed from the sheath 400 to prevent clot dislodgement at the RHV 434. The RHV 434 can be a dual RHV or a multi-head RHV.

The RHV 434 can form a Y-connector on the proximal end 403 of the sheath 400 such that the first port of the RHV 434 can be used for insertion of a working catheter into the working lumen of the sheath 400 and a second port into arm 412 can be used for another purpose. For example, a syringe or other device can be connected at arm 412 via a connector 432 to deliver a forward drip, a flush line for contrast or saline injections through the body 402 toward the tip 406 and into the target anatomy. Arm 412 can also connect to a vacuum source 505 (see FIG. 2B). The vacuum source 505 can be an active source of aspiration such as an aspiration pump, a regular or locking syringe, a hand-held aspirator, hospital suction, or the like, configured to draw suction through the working lumen. In an embodiment, the vacuum source 505 is a locking syringe (for example a VacLok Syringe) attached to a flow controller. The user can pull the plunger on the syringe back into a locked position while the connection to the flow line is closed prior to an embolectomy step of the procedure. Alternatively, the syringe can be aspirated in a way to create a manual cycling to induce fracture and more rapid evacuation of the embolus. During the procedure when the distal tip of the catheter is near or at the face of the occlusion, the user may open the connection to the aspiration syringe. This allows for a maximum communication of aspiration force being applied through the working lumen of the sheath 400 and any catheter extending through the sheath 400 that in turn is in communication with the vessel at its distal end. A single user at the single, shared source can apply the aspiration in a rapid fashion. In another implementation, the arm 412 can be connected to a vacuum source 505 that is a pump configured to apply an aspiration pressure through the working lumen of the guide sheath 400. The single, shared source of aspiration is sufficient to draw aspiration through the entire system 100, even when multiple aspiration catheters 200 are nested within one another through the working lumen of the guide sheath 400. The arm 412 can also allow the guide sheath 400 to be flushed with saline or radiopaque contrast during a procedure. The working lumen can extend from a distal end to a working proximal port of the proximal end region 403 of the sheath body 402.

The vacuum source 505 can increase in aspiration level when the flow rate is slow and decrease when the flow rate is increased. In this manner, the force is greatest when the catheter is clogged or partially clogged, but decreases to a minimal level when there is free flow to ensure protection from distal emboli but limit the volume of aspirated blood. In this manner, the system optimizes the embolus aspiration while limiting the amount of blood aspirated. Alternately, the vacuum source 505 can include a vacuum gauge. When the flow in the catheter 200 is blocked or restricted the pump creates a higher level of vacuum. In this example, the aspiration force may be configured to rise when higher vacuum is detected. Alternatively, the vacuum gauge may be incorporated into the RHV or the Luer or proximal end of the guide sheath 400. Use of the term "embolus" is not intended to be limiting and may be referred to herein as a "clot," a "thrombus," "occlusion" and the like.

In yet another vacuum source implementation, the vacuum source 505 provides a cyclic level of aspiration force, for example, an aspiration force that cycles between a high level of vacuum to a lower level of vacuum at a set frequency or frequencies, or from a high level of vacuum to no vacuum, or from a high level of vacuum to a positive pressure. A cyclic aspiration mode may provide a jackhammer type force on the embolus and increase the ability to aspirate the embolus through the catheter. One effect of these forces is to fatigue and fracture the embolus that is often engulfed in the catheter and recruit a slow progressive movement of the thrombotic material down the length of the catheter, especially when static aspiration is incapable of doing so. Another effect of cyclic forces is to change the friction regime and to challenge connections between the clot and the vessel wall, encouraging the clot to loosen to propel the clot towards the vacuum source. The cyclic aspiration force may be enabled through the use of solenoid valves, electronically controlled valves, manual or mechanical valves, a programmable pump motor controller, or the like. In an implementation, cyclic aspiration is applied only when clogged or restricted flow is detected in the aspiration line, either through low flow or through high vacuum, and at other times, the vacuum source reverts to a low level of flow, or be turned off. This configuration may be controlled by the user, or controlled automatically via a feedback loop to the vacuum source. Cycling aspiration is described in more detail below.

The embolus may be captured by the catheter such that at least a portion of the embolus is contained within the lumen of the catheter while another portion of the embolus remains outside the lumen of the catheter. Capture of the embolus where a portion of the embolus remains outside the catheter lumen can be referred to herein as "corked" or "corking" the catheter. Generally, a corked catheter is one where full evacuation of the embolus into the proximal canister is not possible and instead the catheter is withdrawn carrying the corked embolus with it. The embolus may be captured by the catheter such that a majority of the embolus is contained within the catheter lumen while a small portion or no portion of the embolus remains outside the catheter lumen. Capture of the embolus where a majority of the embolus is contained within the lumen can be referred to herein as being "engulfed" by the catheter. An embolus that is engulfed in the catheter lumen may still progress towards the proximal canister under aspiration pressure or the engulfed embolus may move only minimally within the catheter lumen and ultimately a surgeon withdraw the catheter in order to remove the embolus from the patient.

As will be described in more detail below, the type of aspiration applied through the catheter lumen (e.g. static pressure or cyclic pressure) can vary depending on the stage of the procedure, user preference, and/or whether the embolus is corked, engulfed and progressing, or engulfed and not progressing through the catheter lumen, or whether full evacuation of the embolus to the proximal canister and free-flow ensues. For example, a surgeon can apply cyclic aspiration to fatigue or fracture the embolus. In the situation of the occluded or nearly occluded catheter tip, a cyclic pattern of aspiration may be advantageous. A backflow of free-flowing fluid to fill the potential space in the distal catheter tip as the embolus migrates is helpful for movement of the embolus through the catheter length. Should the aspiration create a "suck-down" effect where there is vessel collapse and no flow of blood antegrade (i.e. from the parent vessel) or retrograde (i.e. from collateral circulation, which is abundant in the cerebral circulation), then movement of the embolus down the catheter length would generally not be facilitated. A constant relentless pressure is more likely to exhaust any potential backfilling flow from embolus movement down the catheter. A negative pressure-cycling pattern may allow intermittent relief to allow antegrade and retrograde flow dependent on the force and frequency of the cyclic pressure applied. Cycling of pressure may also create a greater velocity of embolus movement purely from fatiguing, fracturing, or a frictional effect on the embolus or on the interface of the embolus and the catheter lumen or vessel wall.

Once corking occurs and the surgeon deems it necessary to withdraw the corked catheter, the surgeon can switch to static full pressure aspiration. Generally, an embolus in a corked or restricted flow state where the portion of the embolus external to the lumen may fragment and embolize due to catheter movement is withdrawn with the catheter under static aspiration and preferably under maximum force to compress and hold the embolus during catheter removal. As another example, a surgeon can apply cyclic aspiration to engulf the embolus. Cyclic aspiration can continue for as long as the surgeon desires to aspirate the engulfed embolus through the lumen. In an implementation, it may be preferred that cyclic aspiration be applied during periods of reduced catheter movement. The engulfed embolus may be fully evacuated (i.e. clear to the proximal canister or syringe) under cyclic aspiration. The engulfed embolus may be fully evacuated under static aspiration. The engulfed embolus may be at least partially evacuated using cyclic and at least partially evacuated using static aspiration before ultimately being withdrawn with the catheter. The aspiration forces can be shifted in real-time during a procedure between static aspiration and cyclic aspiration. Different cycling frequencies and amplitudes can be performed depending on the diameter of the catheter being used, the location of the aspiration valve/pressure relief/pressure altering mechanism, and the degree that which pressure is relieved or changed to create a different movement of the embolus. The surgeon can switch from cyclic aspiration to static aspiration at any time if it is observed there is no flow and the catheter is to be withdrawn to remove the corked embolus.

The length of the catheter body 402 is configured to allow the distal tip 406 of the body 402 to be positioned as far distal in the internal carotid artery (ICA), for example, from a transfemoral approach, with additional length providing for adjustments if needed. In some implementations (e.g. femoral or radial percutaneous access), the length of the body 402 can be in the range of 80 to 90 cm or can be longer, for example, up to about 100 cm or up to about 105 cm. In implementations, the body 402 length is suitable for a transcarotid approach to the bifurcation of the carotid artery, in the range of 20-25 cm. In further implementations, the body 402 length is suitable for a percutaneous transcarotid approach to the CCA or proximal ICA, and is in the range of 10-15 cm. The body 402 is configured to assume and navigate the bends of the vasculature without kinking, collapsing, or causing vascular trauma, even, for example, when subjected to high aspiration forces.

Figure 1B:
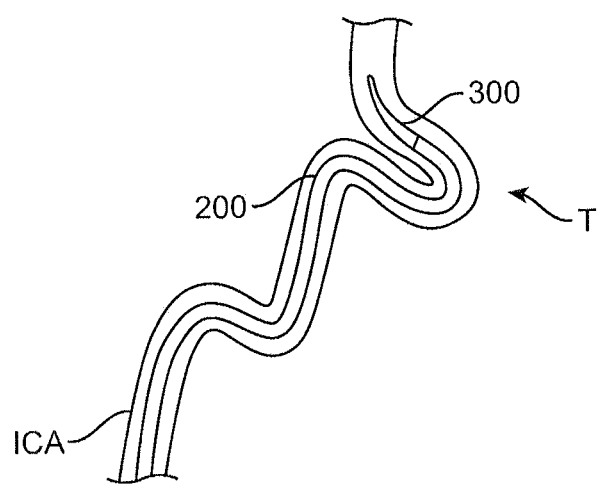
Figure 1C:
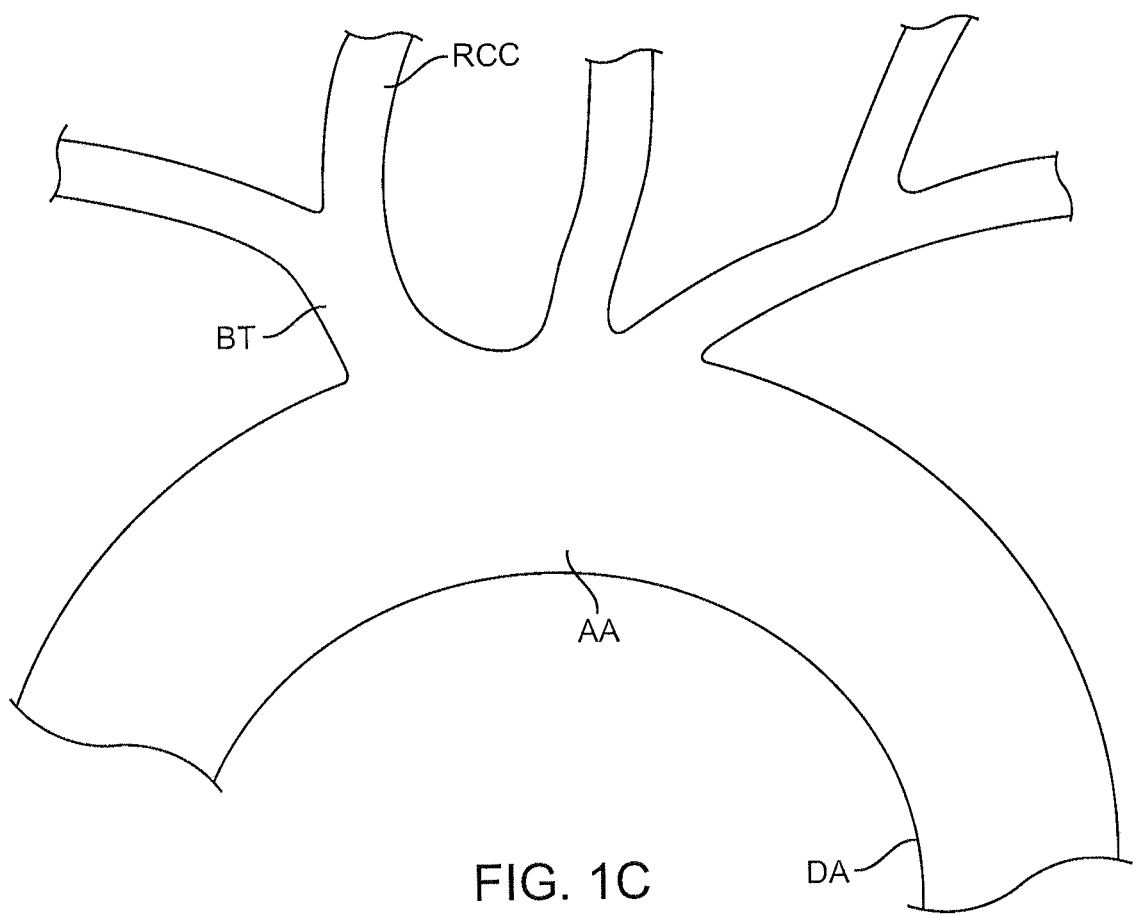
FIG. 1C illustrates the aortic arch including the take-offs of the brachiocephalic BT, left common carotid, and left subclavian arteries from the aortic arch AA.

In some implementations, the system 100 can further include a select tool for advancing the guide sheath 400. The select tool can have an outer diameter configured to be received within the working lumen of the guide sheath 400 such that a distal end region of the select tool extends a distance distal to the distal end of the guide sheath 400. The outer diameter of the select tool sufficiently fills the inner diameter of the working lumen of the guide sheath 400 to minimize the lip at the distal opening 408 of the guide sheath 400. For example, if the working lumen of the guide sheath 400 has an inner diameter that is between about 0.087" to about 0.113", the outer diameter of the select tool can be about 0.006" less than this, or between about 0.081" to about 0.107". The brachiocephalic take-off (BT) is typically a very severe turn off the aortic arch AA for a transfemorally-delivered catheter seeking the right-sided cerebral circulation (shown in FIG. 1C). A catheter traverses from the femoral artery through the iliac circulation into the descending aorta DA. The catheter turns as it approaches the aortic arch AA and reaches across the take-off of other great vessels to reach the brachiocephalic take-off (BT), which is the furthest "reach" of the great vessels of the aortic arch AA. FIG. 1C shows the substantial and obligatory S-turn created by that anatomy. A catheter must traverse this S-turn along a path of insertion from a femoral artery insertion location in order to reach the internal carotid artery (ICA). The left ICA often takes off from the brachiocephalic and thus, has a similar challenge and can create an even tighter S-turn. Should the left ICA have a typical take-off between the brachiocephalic BT and the left subclavian artery LSA take-off, then the reach may be less severe, but an S-turn still develops of lesser severity. The distal end region of the select tool can be tapered and/or shaped to provide support and guidance to advance the sheath 400 around this turn into the ICA. In some implementations, the select tool can have a Bernstein Select-style or a Simmons-style reverse curve catheter tip as is known in the art.

The tip 406 of the guide sheath 400 can have a same or similar outer diameter as a section of the body 402 leading up to the distal end. Accordingly, the tip 406 may have a distal face orthogonal to a longitudinal axis passing through the body 402 and the distal face may have an outer diameter substantially equal to a cross-sectional outer dimension of the body 402. In an implementation, the tip 406 includes a chamfer, fillet, or taper, making the distal face diameter slightly less than the cross-sectional dimension of the body 402. In a further implementation, the tip 406 may be an elongated tubular portion extending distal to a region of the body 402 having a uniform outer diameter such that the elongated tubular portion has a reduced diameter compared to the uniform outer diameter of the body 402. Thus, the tip 406 can be elongated or can be more bluntly shaped. Accordingly, the tip 406 may be configured to smoothly track through a vasculature and/or to dilate vascular restrictions as it tracks through the vasculature. The working lumen may have a distal end forming a distal opening 408.

The guide sheath 400 may include a tip 406 that tapers from a section of the body 402 leading up to the distal end. That is, an outer surface of the body 402 may have a diameter that reduces from a larger dimension to a smaller dimension at a distal end. For example, the tip 406 can taper from an outer diameter of approximately 0.114" to about 0.035" or from about 0.110" to about 0.035" or from about 0.106" to about 0.035". The angle of the taper of the tip 406 can vary depending on the length of the tapered tip 406. For example, in some implementations, the tip 406 tapers from 0.110" to 0.035" over a length of approximately 50 mm.

In an implementation, the guide sheath 400 includes one or more radiopaque markers 411. The radiopaque markers 411 can be disposed near the distal tip 406. For example, a pair of radiopaque bands may be swaged, painted, embedded, or otherwise disposed in or on the body 402. In some implementations, the radiopaque markers 411 include a barium polymer, tungsten polymer blend, tungsten-filled or platinum-filled marker that maintains flexibility of the distal end of the device and improves transition along the length of the guide sheath 400 and its resistance to kinking. In some implementations, the radiopaque marker 411 is a tungsten-loaded PEBAX or polyurethane that is heat welded to the body 402. The markers 411 are shown in the figures as rings around a circumference of one or more regions of the body 402. However, the markers 411 can have other shapes or create a variety of patterns that provide orientation to an operator regarding the position of the distal opening 408 within the vessel. Accordingly, an operator may visualize a location of the distal opening 408 under fluoroscopy to confirm that the distal opening 408 is directed toward a target anatomy where a catheter 200 is to be delivered. For example, radiopaque marker(s) 411 allow an operator to rotate the body 402 of the guide sheath 400 at an anatomical access point, e.g., a groin of a patient, such that the distal opening provides access to an ICA by subsequent working device(s), e.g., catheters and wires advanced to the ICA. In some implementations, the radiopaque marker(s) 411 include platinum, gold, tantalum, tungsten or any other substance visible under an x-ray fluoroscope. Any of the various components of the systems described herein can incorporate radiopaque markers.

In some implementations, the guide sheath 400 can have performance characteristics similar to other sheaths used in carotid access and AIS procedures in terms of kinkability, radiopacity, column strength, and flexibility. The inner liners can be constructed from a low friction polymer such as PTFE (polytetrafluoroethylene) or FEP (fluorinated ethylene propylene) to provide a smooth surface for the advancement of devices through the inner lumen. An outer jacket material can provide mechanical integrity to the inner liners and can be constructed from materials such as PEBAX, thermoplastic polyurethane, polyethylene, nylon, or the like. The body 402 can include a hydrophilic coating. A third layer can be incorporated that can provide reinforcement between the inner liner and the outer jacket. The reinforcement layer can prevent flattening or kinking of the inner lumen of the body 402 to allow unimpeded device navigation through bends in the vasculature as well as aspiration or reverse flow. The body 402 can be circumferentially reinforced. The reinforcement layer can be made from metal such as stainless steel, Nitinol, Nitinol braid, helical ribbon, helical wire, cut stainless steel, or the like, or stiff polymer such as PEEK. The reinforcement layer can be a structure such as a coil or braid, or tubing that has been laser-cut or machine-cut to be flexible. In another implementation, the reinforcement layer can be a cut hypotube such as a Nitinol hypotube or cut rigid polymer, or the like. The outer jacket of the body 402 can be formed of increasingly softer materials towards the distal end. The flexibility of the body 402 can vary over its length, with increasing flexibility towards the distal portion of the body 402. The variability in flexibility may be achieved in various ways. For example, the outer jacket may change in durometer and/or material at various sections. A lower durometer outer jacket material can be used in a distal section of the guide sheath compared to other sections of the guide sheath. Alternately, the wall thickness of the jacket material may be reduced, and/or the density of the reinforcement layer may be varied to increase the flexibility. For example, the pitch of the coil or braid may be stretched out, or the cut pattern in the tubing may be varied to be more flexible. Alternately, the reinforcement structure or the materials may change over the length of the sheath body 402. In another implementation, there is a transition section between the distal-most flexible section and the proximal section, with one or more sections of varying flexibilities between the distal-most section and the remainder of the sheath body 402. In this implementation, the distal-most section is about 2 cm to about 5 cm, the transition section is about 2 cm to about 10 cm and the proximal section takes up the remainder of the sheath length. In some implementations, the proximal region of the body 402 can be formed of a material such as Nylon, a region of the body 402 distal to the proximal region of the body 402 can have a material hardness of 72D whereas areas more distal can be increasingly more flexible and formed of materials having a material hardness of 55D, 45D, 35D extending towards the distal tip 406, which can be formed of a material having a material hardness of 35D, for example.

The working lumen of the guide sheath 400 can have different inner diameters configured to receive different outer diameter catheters 200. In some implementations, the working lumen of a first guide sheath 400 can have an inner diameter sized to receive a 6F catheter and the working lumen of a second guide sheath 400 can have an inner diameter sized to receive an 8F catheter. The guide sheaths 400 can receive catheters having an outer diameter along at least a length that is snug to the inner diameter dimension of the guide sheath 400. The guide sheath 400 (as well as any of the variety of components used in combination with the sheath 400) can be an over-the-wire (OTW) or rapid exchange type device, which will be described in more detail below.

The sheath 400 can include a body 402 formed of generally three layers, including a lubricious inner liner, a reinforcement layer, and an outer jacket layer. The reinforcement layer can include a braid to provide good torqueability optionally overlaid by a coil to provide good kink resistance. In sheaths where the reinforcement layer is a braid alone, the polymers of the outer jacket layer can be generally higher durometer and thicker to avoid issues with kinking. The wall thickness of such sheaths that are braid alone with thicker polymer can be about 0.011". The wall thickness of the sheaths 400 described herein having a braid with a coil overlay provide both torqueability and kink resistance and can have a generally thinner wall, for example, a wall thickness of about 0.0085". The proximal end outer diameter can thereby be reduced to less than 0.112", for example, about 0.107" outer diameter. It is generally beneficial to limit the overall OD of the guide sheath 400 such that the entry wound into the patient (e.g. at the femoral artery) can be kept to a minimum size. Thus, the sheath 400 is a high-performance sheath 400 that has good torque and kink resistance with a thinner wall providing an overall lower profile to the system. The thinner wall and lower profile allows for a smaller insertion hole through the vessel without affecting overall lumen size. In some implementations, the wall thickness of the guide sheath 400 can slowly step down to be thinner towards a distal end of the sheath compared to a proximal end.

The system can include localized points of low clearance between the guide sheath 400 and the catheter 200 extending through it. The localized points of low clearance can provide localized sealing between the structures. In some implementations, the localized sealing can be near the distal end region of the guide sheath 400 and in others, the localized sealing can be a distance away from the distal end of the guide sheath 400. The catheter 200 can have an increase in OD near a proximal end region creating a cylindrical region of the catheter that forms a snug fit (e.g. less than about 0.002" clearance) with the ID of the guide sheath 400. The length of this low clearance sealing region can vary and depend on the overall clearance between the ID and OD. Greater differences in ID/OD (i.e. higher clearance) can provide sufficient sealing at aspirational pressures by increasing the length of the cylindrical sealing region. Smaller differences in ID/OD (i.e. lower clearance) can provide sufficient sealing at aspirational pressures while having a shorter cylindrical length. In other words, a shorter sealing zone may have a closer fit or lower clearance whereas a longer sealing zone need not have such a close fit and can have a higher clearance.

The guide sheath 400 can also include additional localized sealing points with the catheter extending through its working lumen. In some implementations, the localized sealing can occur a distance away from the distal end 406 of the sheath 400. In some implementations, a localized sealing can occur at the distal end 406 of the sheath 400. For example, the guide sheath 400 may include a distal tip 406 that is designed to seal well with an outer diameter of a catheter extending through its working lumen. The distal tip 406 can be formed of soft material that is devoid of both liner and reinforcement layers. The lubricious liner layer and also the reinforcement layer can extend through a majority of the body 402 except for a length of the distal tip 406 (see FIG. 2C). The length of this unlined, unreinforced portion of the distal tip 406 of the sheath 400 can vary. In some implementations, the length is between about 3 mm to about 6 mm of the distal end region of the sheath 400. Thus, the liner 409 of the sheath 400 can terminate at least about 3 mm away from the distal-most terminus of the sheath 400 leaving the last 3 mm unlined soft material forming the distal tip 406. In some implementations, the coil and braid of the reinforcement layer can have their ends held in place by a radiopaque markers 411, such as a marker band positioned near a distal-most terminus of the sheath 400. The liner layer 409 can extend at least a length distal to the marker band 411 before terminating, for example, a length of about 1 mm. The staggered termination of the wall layers can aid in the transition from the marker band 411 to the soft polymer material 407 of the distal tip 406. The soft polymer material 407 can extend a length beyond the liner layer 409. The unlined, soft material 407 forming the distal tip 406 can be a PEBAX material having a durometer of no more than about 40D, no more than about 35D, no more than about 62A, or no more than about 25D. The softness of the material and the length of this unlined distal tip 406 of the sheath 400 can vary. Generally, the material is soft enough to be compressed down onto the outer diameter of the catheter 200 extending through the lumen of the sheath 400, such as upon application of a negative pressure through the lumen. The length of this unlined, unreinforced region 407 of the distal tip 406 is long enough to provide a good seal, but not so long as to cause problems with according or folding over during relative sliding between the sheath 400 and the catheter 200 that might blocking the sheath lumen or negatively impacting slidability of the catheter 200 within the sheath lumen.

The distal tip 406 can have an inner diameter that approaches the outer diameter of the catheter 200 that extends through the sheath 400. In some implementations, the inner diameter of the distal tip 406 can vary depending on what size catheter is to be used. For example, the inner diameter of the sheath at the distal tip 406 can be about 0.106" when the outer diameter of the catheter near the proximal end is about 0.101" such that the difference in diameters is about 0.005". Upon application of a vacuum, the soft unlined and unreinforced distal tip 406 can move to eliminate this 0.005" gap and compress down onto the outer diameter of the catheter 200 near its proximal end region upon extension of the catheter 200 out its distal opening 408. The difference between the inner diameter of the distal tip 406 and the outer diameter of the catheter can be between about 0.002"-0.006". The inner diameter of the distal tip 406 can also be tapered such the inner diameter at the distal-most terminus of the opening 408 is only 0.001" to 0.002" larger than the outer diameter of the proximal end of the catheter 200 extending through the working lumen. In some implementations, the distal tip 406 is shaped such that the walls are beveled at an angle relative to a central axis of the sheath 400, such as about 60 degrees.

In some instances, it is desirable for the sheath body 402 to also be able to occlude the artery in which it is positioned, for example, during procedures that may create distal emboli. Occluding the artery stops antegrade blood flow and thereby reduces the risk of distal emboli that may lead to neurologic symptoms such as TIA or stroke. FIG. 2D shows an arterial access device or sheath 400 that has a distal occlusion balloon 440 that upon inflation occludes the artery at the position of the sheath distal tip 406. At any point in a procedure, for example, during removal of an occlusion by aspiration and/or delivery of a stent retriever or other interventional device, the occlusion balloon 440 can be inflated to occlude the vessel to reduce the risk of distal emboli to cerebral vessels. The sheath 400 can include an inflation lumen configured to deliver a fluid for inflation of the occlusion balloon 440 in addition to the working lumen of the sheath 400. The inflation lumen can fluidly connect the balloon 440, for example, to arm 412 on the proximal adaptor. This arm 412 can be attached to an inflation device such as a syringe to inflate the balloon 440 with a fluid when vascular occlusion is desired. The arm 412 may be connected to a passive or active vacuum source to further reduce the risk of distal emboli.

According to some implementations, the length of the guide sheath 400 is long enough to access the target anatomy and exit the arterial access site with extra length outside of a patient's body for adjustments. For example, the guide sheath 400 (whether having a distal occlusion balloon 440 or not) can be long enough to access the petrous ICA from the femoral artery such that an extra length is still available for adjustment.

The sealing clearance between the guide sheath 400 and the catheter 200 can be a function of localized low clearance regions in ID/OD. The size of the clearance can change depending on whether aspiration pressure is applied through the system. For example, the catheter 200 can also include a slit in the luminal portion 222 configured to widen slightly upon application of suction from a vacuum source and improve sealing between the catheter 200 and the guide sheath 400. Additionally, or alternatively, the distal tip 406 of the sheath 400 can be designed to move downward onto the outer diameter of the catheter 200 to improve sealing. The strength of the localized seal(s) achieved allows for a continuous aspiration lumen from the distal tip of the catheter 200 to a proximal end 403 of the guide sheath 400 where it is connected to the vacuum source, even in the presence of lower suction forces, with minimal to no leakage. Generally, when there is enough overlap between the catheter 200 and the guide sheath 400 there is no substantial leakage. However, when trying to reach distal anatomy, the catheter 200 may be advanced to its limit and the overlap between the catheter 200 and the guide sheath 400 is minimal. Thus, additional sealing can be desirable to prevent leakage around the catheter 200 into the sheath 400. The sealing between the catheter 200 and the guide sheath 400 can prevent this leakage upon maximal extension of catheter 200 relative to sheath 400.

Distal Access Catheters

Figure 3:
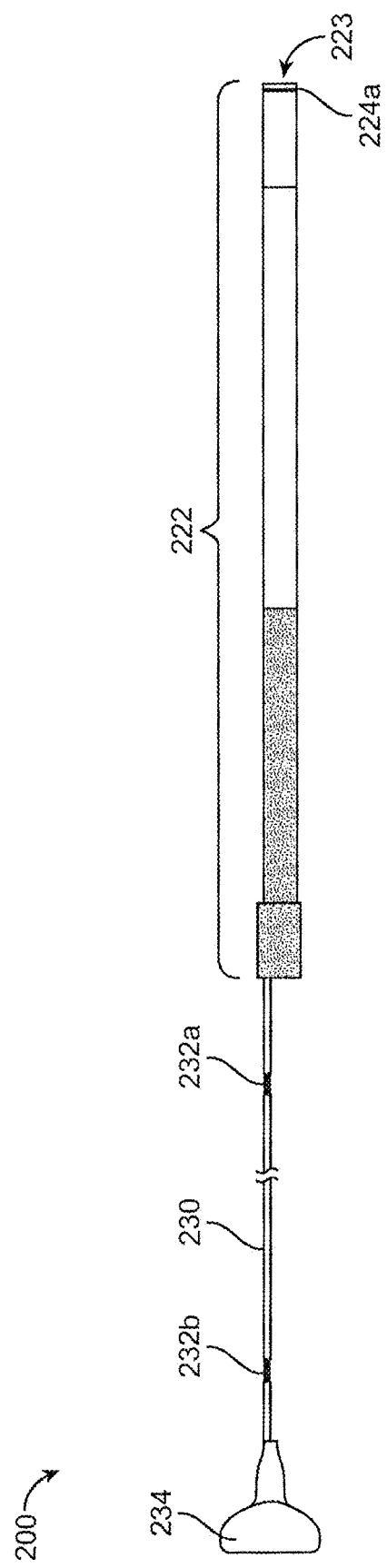
FIG. 3 is a side view of an implementation of a spined distal access catheter.

Again, with respect to FIGS. 2A-2B, the distal access system 100 can include one or more catheters 200 configured to extend through and out the distal end of the guide sheath 400. The catheter 200 can be a distal access, support, or aspiration catheter depending on the method being performed. FIG. 3 illustrates a side elevational view of an implementation of the catheter 200. The catheter 200 can include a relatively flexible, distal luminal portion 222 coupled to a stiffer, kink-resistant proximal extension or proximal control element 230. The term "control element" as used herein can refer to a proximal region configured for a user to cause pushing movement in a distal direction as well as pulling movement in a proximal direction. The control elements described herein may also be referred to as spines, tethers, push wires, push tubes, or other elements having any of a variety of configurations. The proximal control element can be a hollow or tubular element. The proximal control element can also be solid and have no inner lumen, such as a solid rod, ribbon or other solid wire type element. Generally, the proximal control elements described herein are configured to move its respective component (to which it may be attached or integral) in a bidirectional manner through a lumen.

The catheter 200 provides a quick way to access stroke locations with simplicity even through the extreme tortuosity of the cerebral vasculature. The catheters described herein have a degree of flexibility and deliverability that makes them optimally suitable to be advanced through the cerebral vascular anatomy without kinking or ovalizing even when navigating hairpin turns. For example, the distal luminal portion 222 can perform a 180 degree turn (see turn T shown in FIG. 1B near the carotid siphon) and maintain a folded width across of 4.0 mm without kinking or ovalizing. Further, the distal luminal portion 222 has a degree of flexibility that maintains the natural tortuosity of the vessels through which it is advanced without applying straightening forces such that the natural shape and curvature of the anatomy is maintained during use. The catheter 200, particularly in combination with a catheter advancement element 300, which will be described in more detail below, provides an extended conduit beyond the guide sheath 400 having exceptional deliverability through convoluted anatomy that allows for delivering aspirational forces to a target stroke site as well as for the delivery of stroke interventional devices such as another aspiration catheter, or a device such as a stent retriever, stent, flow diverter or other working devices.

A single, inner lumen 223 extends through the luminal portion 222 between a proximal end and a distal end of the luminal portion 222. The inner lumen 223 of the catheter 200 can have a first inner diameter and the working lumen of the guide sheath 400 can have a second, larger inner diameter. Upon insertion of the catheter 200 through the working lumen of the sheath 400, the lumen 223 of the catheter 200 can be configured to be fluidly connected and contiguous with the working lumen of the sheath 400 such that fluid flow into and/or out of the system 100 is possible, such as by applying suction from a vacuum source coupled to the system 100 at a proximal end. The combination of sheath 400 and catheter 200 can be continuously in communication with the bloodstream during aspiration at the proximal end with advancement and withdrawal of catheter 200.

The spined catheter system can create advantages for distal access over conventional, full-length catheters particularly in terms of aspiration. The step change in the internal diameter of the catheter (i.e. from the inner lumen 223 of the catheter to the working lumen of the sheath 400) creates a great advantage in aspiration flow and force that can be generated by the spined catheter 200 in combination with the conventional guide catheter. For example, where a spined catheter 200 with a 0.070" internal diameter is paired with a standard 6F outer diameter/0.088" internal diameter guide catheter (e.g. Penumbra Neuron MAX 088) can create aspiration physics where the 0.088" catheter diameter will predominate and create a 0.080" equivalent flow in the entire system. This improvement can be mathematically approximated using the Hagen-Poiseulle equation where the pressure drop between the catheter tip and its connection to the vacuum system (dP) is equal to $8uLQ/piR^4$ where L is the catheter length, u is the dynamic viscosity of the liquid, Q is the volumetric flow rate, and R is the catheter radius. Rearranging the equation to solve for volumetric flow rate (an analog for catheter effectiveness) is $Q=dPpiR^4/8 uL$. Different catheter designs having different effective radii can be compared within the same system by holding all other variables constant (e.g. vacuum pressure, fluid, length). Volumetric flow is directly proportional to the radius of the catheter to the fourth power. Thus, increasing the effective catheter radius has significant benefits in terms of volumetric flow rate and catheter performance.

In addition to aspiration procedures, the catheter 200 and distal access system 100 can be used for delivery of tools and interventional working devices. For example, a typical stent retriever to be delivered through the catheter 200 can have a long push wire control element (e.g. 180 cm long). The distal access system 100 having a spined support catheter 200 allows for reaching distal stroke sites using much shorter lengths (e.g. 120 cm-150 cm). The overall length can be as important as diameter and radius on aspiration through the catheter. The shorter lengths in combination with the elimination of the multiple RHVs typical in tri-axial systems allows for a single-operator use.

Where the catheter is described herein as an aspiration catheter, it should not be limited to only aspiration. Similarly, where the catheter is described herein as a way to deliver a stent retriever or other working device it should not be limited as such. The systems described herein can be used to perform procedures that incorporate a combination of treatments. For example, the catheter 200 can be used for the delivery of a stent retriever delivery system, optionally in the presence of aspiration through the catheter 200. As another example, a user may start out performing a first interventional procedure using the systems described herein, such as aspiration embolectomy (sometimes referred to as "thrombectomy"), and switch to another interventional procedure, such as delivery of a stent retriever or implant.

The terms "support catheter," "spined catheter," "tethered catheter," "distal access catheter," "aspiration catheter," and "intermediate catheter" may be used interchangeably herein.

It is desirable to have a catheter 200 having an inner diameter that is as large as possible that can be navigated safely to the site of the occlusion, in order to optimize the aspiration force in the case of aspiration and/or provide ample clearance for delivery of a working device. A suitable size for the inner diameter of the distal luminal portion 222 may range between 0.040" and 0.100", or more preferably between 0.054" and 0.088", depending on the patient anatomy and the clot size and composition. The outer diameter of the distal luminal portion 222 can be sized for navigation into cerebral arteries, for example, at the level of the M1 segment or M2 segment of the cerebral vessels. The outer diameter (OD) should be as small as possible while still maintaining the mechanical integrity of the catheter 200. In an implementation, the difference between the OD of distal luminal portion 222 of the catheter 200 and the inner diameter of the working lumen of the guide sheath 400 is between 0.001" and 0.002". In another implementation, the difference is between 0.001" and 0.004". The clearance between inner diameter of the guide sheath 400 and the outer diameter of the catheter 200 can vary throughout the length of the catheter 200. For example, the distal luminal portion 222 of the catheter 200 can have localized regions of enlarged outer diameter creating localized low clearance regions (e.g. about 0.001" difference) configured for localized sealing upon application of aspiration pressure through the system.

In some implementations, the distal luminal portion 222 of the catheter 200 has a maximum outer diameter (OD) configured to fit through a 6F introducer sheath (0.070"-0.071") and the lumen 223 has an inner diameter (ID) that is sized to receive a 0.054" catheter. In some implementations, the distal luminal portion 222 has a lumen and a distal end having an opening from the lumen, the lumen can have an inner diameter (ID) at the distal end that is at least about 0.052". In some implementations, the distal luminal portion 222 of the catheter 200 has a maximum OD configured to fit through an 8F introducer sheath (0.088") and the lumen 223 has an ID that is sized to receive a 0.070" or 0.071" catheter. In some implementations, the maximum OD of the distal luminal portion 222 is 2.1 mm and the lumen 223 has an ID that is 0.071". In some implementations, the lumen 223 has an ID that is 0.070" to 0.073". The outer diameter of the guide sheath 400 can be suitable for insertion into at least the carotid artery, with a working lumen suitably sized for providing a passageway for the catheter 200 to treat an occlusion distal to the carotid artery towards the brain. In some implementations, the ID of the working lumen can be about 0.074" and the OD of the body of the guide sheath 400 can be about 0.090", corresponding to a 5 French sheath size. In some implementations, the ID of the working lumen can be about 0.087" and the OD of the body of the guide sheath 400 can be about 0.104", corresponding to a 6 French sheath size. In some implementations, the ID of the working lumen can be about 0.100" and the OD of the body of the guide sheath 400 can be about 0.117", corresponding to a 7 French sheath size. In some implementations, the guide sheath 400 ID is between 0.087" and 0.088" and the OD of the distal luminal portion 222 of the catheter 200 is approximately 0.082" and 0.086" such that the difference in diameters is between 0.001" and 0.005". Smaller or larger sheath sizes are considered. For example, in some implementations the ID of the lumen 223 is about 0.088" and the OD of the distal luminal portion is between 0.101"-0.102". However, a conventional 7 French sheath has an ID that is only about 0.100" and a conventional 8 French sheath has an ID that is about 0.113" such that it would not provide a suitable sealing fit with the OD of the distal luminal portion of the catheter for aspiration embolectomy (i.e. 0.011" clearance). Thus, the guide sheath 400 can be designed to have an inner diameter that is better suited for the 0.088" catheter, namely between 0.106"-0.107". Additionally, the 0.088" catheter can have a step-up in OD from 0.101"-0.102" to about 0.105"-0.107" OD near a proximal end region to provide a localized area optimized for sealing with the guide sheath during application of high pressure.

In an implementation, the luminal portion 222 of the catheter 200 has a uniform diameter from a proximal end to a distal end. In other implementations, the luminal portion 222 of the catheter 200 is tapered and/or has a step-down towards the distal end of the distal luminal portion 222 such that the distal-most end of the catheter 200 has a smaller outer diameter compared to a more proximal region of the catheter 200, for example, near where the distal luminal portion 222 seals with the guide sheath 400. In another implementation, the luminal portion 222 of the catheter OD steps up at or near an overlap portion to more closely match the sheath inner diameter as will be described in more detail below. This step-up in outer diameter can be due to varying the wall thickness of the catheter 200. For example, the catheter 200 can have a wall thickness that is slightly thicker near the proximal end to provide better sealing with the sheath compared to a wall thickness of the catheter 200 near the distal end. The catheter 200 can have a thicker wall at this location while maintaining a uniform inner diameter. This implementation is especially useful in a system with more than one catheter suitable for use with a single access sheath size. In some implementations, a thicker wall can be created by embedding a radiopaque material (e.g. tungsten) such that the localized step-up in OD can be visualized during a procedure. The catheter 200 may have a step-up in outer diameter near the proximal end region that does not result from a thicker wall. For example, the inner diameter of the lumen may also step-up such that the wall thickness remains uniform, but the lumen size increases thereby increasing the overall OD at this location.

The length of the luminal portion 222 can be shorter than a length of the working lumen of the guide sheath 400 such that upon advancement of the luminal portion 222 towards the target location results in an overlap region 348 between the luminal portion 222 and the working lumen (see FIG. 2B). The length of the overlap region 348 can vary depending on the length of the distal luminal portion 222 and the distance to the target location relative to the distal end of the guide sheath 400. Taking into account the variation in occlusion sites and sites where the guide sheath 400 distal tip 406 may be positioned, the length of the luminal portion 222 may range from about 10 cm to about 80 cm, or between 35 cm to about 75 cm, or between about 45 cm to about 60 cm. In some implementations, the distal luminal portion 222 of the catheter 200 can be between 45 cm-70 cm and the control element 230 of the catheter 200 can be between about 90 cm to about 100 cm. In some implementations, the catheter 200 can have a total working length that is approximately 115 cm. In other implementations, the working length of the catheter 200 between a proximal end of the catheter to a distal end of the catheter can be greater than 115 cm up to about 130 cm. In some implementations, the catheter 200 can have a working length greater than 130 cm between a proximal tab 234 (or proximal hub) and the distal tip, for example, 133 cm. The distal luminal portion 222 can have a shaft length of about 40 cm±3 cm. The distal luminal portion 222 can have a shaft length that is at least about 45 cm up to a length that is shorter than the working length of the sheath 400. The body 402 of the guide sheath 400 can be between about 80 cm to about 90 cm.

The length of the luminal portion 222 can be less than the length of the body 402 of the guide sheath 400 such that as the catheter 200 is extended from the working lumen there remains an overlap region 348 of the catheter 200 and the inner diameter of the working lumen. A seal can be formed within a region of the overlap region 348. In some implementations, the length of the luminal portion 222 is sufficient to reach a region of the M1 segment of the middle cerebral artery (MCA) and other major vessels from a region of the internal carotid artery while the proximal end region of the luminal portion 222 of the catheter 200 is still maintained proximal to certain tortuous anatomies (e.g. brachiocephalic take-off BT, the aortic arch AA, or within the descending aorta DA). In an implementation, the luminal portion 222 of the catheter has a length sufficient to position its distal end within the M1 segment of the MCA and a proximal end within the aortic arch proximal to take-offs from the arch. In an implementation, the luminal portion 222 of the catheter has a length sufficient to position its distal end within the M1 segment of the MCA and a proximal end within the descending aorta DA proximal to the aortic arch AA. Used in conjunction with a guide sheath 400 having a sheath body 402 and a working lumen, in an implementation where the catheter 200 reaches the ICA and the distance to embolus can be less than 20 cm.

The distal luminal portion 222 having a length that is less than 80 cm, for example approximately 45 cm up to about 70 cm. The distal luminal portion 222, can allow for an overlap region 348 with the body 402 within which a seal forms with the sheath while still providing sufficient reach to intracranial vessels. The carotid siphon CS is an S-shaped part of the terminal ICA beginning at the posterior bend of the cavernous ICA and ending at the ICA bifurcation into the anterior cerebral artery ACA and middle cerebral artery MCA. In some implementations, the distal luminal portion 222 can be between about 35 cm-80 cm, or between 40 cm-75 cm, or between 45 cm-60 cm long to allow for the distal end of the catheter 200 to extend into at least the middle cerebral arteries while the proximal control element 230 and/or the sealing element on the proximal end region of the distal luminal portion 222 remains proximal to the carotid siphon, and preferably within the aorta as will be described in more detail below.

The distal luminal portion 222 can have a length measured from its point of attachment to the proximal control element 230 to its distal end that is long enough to extend from a region of the internal carotid artery (ICA) that is proximal to the carotid siphon to a region of the ICA that is distal to the carotid siphon, including at least the M1 region of the brain. There exists an overlap region 348 between the luminal portion 222 of the catheter 200 and the working lumen of the guide sheath 400 upon extension of the luminal portion 222 into the target anatomy. A seal to fluid being injected or aspirated can be achieved within the overlap region 348 where the OD of the catheter 200 along at least a portion of the distal luminal portion 222 substantially matches the inner diameter of the guide sheath 400 or the difference can be between 0.001"-0.002". The difference between the catheter OD and the inner diameter of the guide sheath 400 can vary, for example, between 1-2 thousandths of an inch, or between 1-4 thousandths of an inch, or between 1-12 thousandths of an inch. This difference in OD/ID between the sheath and the catheter can be along the entire length of the distal luminal portion 222 or can be a difference in a discrete region of the distal luminal portion 222, for example, a cylindrical, proximal end region of the distal luminal portion 222. In some implementations, a seal to fluid being injected or aspirated between the catheter and the sheath can be achieved within the overlap 348 between their substantially similar dimensions without incorporating any separate sealing structure or seal feature. In some implementations, an additional sealing structure located near the proximal end region of the distal luminal portion 222 provides sealing between the inner diameter of the sheath and the outer diameter of the catheter.

The length of the overlap region 348 between the sheath and the distal luminal portion varies depending on the distance between the distal end of the sheath and the embolus as well as the length of the luminal portion 222 between its proximal and distal ends. The overlap region 348 can be sized and configured to create a seal that allows for a continuous aspiration lumen from the distal tip region of the catheter 200 to a proximal end region 403 of the guide sheath 400 where it can be connected to a vacuum source. In some implementations, the strength of the seal achieved can be a function of the difference between the outer diameter of the catheter 200 and the inner diameter of the working lumen as well as the length of the overlap region 348, the force of the suction applied, and the materials of the components. For example, the sealing can be improved by increasing the length of the overlap region 348. However, increasing the length of the overlap region 348 can result in a greater length through which aspiration is pulled through the smaller diameter of the luminal portion 222 rather than the larger diameter of the working lumen. As another example, higher suction forces applied by the vacuum source can create a stronger seal between the luminal portion 222 and the working lumen even in the presence of a shorter overlap region 348. Further, a relatively softer material forming the luminal portion and/or the body 402 can still provide a sufficient seal even if the suction forces are less and the overlap region 348 is shorter. In an implementation, the clearance of the overlap region 348 can enable sealing against a vacuum of up to approximately 28 inHg with minimal to no leakage. The clearance of the overlap region can enable sealing against a vacuum of up to about 730 mmHg with minimal to no leakage.

In other implementations, the overlap region 348 itself does not provide the sealing between the body 402 and the luminal portion 222. Rather, an additional sealing element positioned within the overlap region 348, for example, a discreet location along a region of the luminal portion 222 narrows the gap between their respective ID and ODs such that sealing is provided by the sealing element within the overlap region 348. In this implementation, the location of the seal between the luminal portion 222 and the body 402 can be positioned more proximally relative to certain tortuous regions of the anatomy. For example, the proximal end region of the luminal portion 222 can have a discreet step-up in outer diameter that narrows the gap between the OD of the luminal portion 222 and the ID of the body 402. This step-up in outer diameter of the luminal portion 222 can be positioned relative to the overall length of the luminal portion 222 such that the sealing region between the two components avoids making sharp turns. For example, the sealing region can include the proximal end region of the luminal portion 222 a certain distance away from the distal tip of the catheter and this sealing region can be designed to remain within the descending aorta DA when the distal end region of the luminal portion 222 is advanced through the aortic arch, into the brachiocephalic trunk BT, the right common carotid RCC, up to the level of the petrous portion of the internal carotid artery and beyond. Maintaining the sealing region below the level of the aortic arch while the distal end of the catheter is positioned within, for example, the M1 region of the MCA is a function of the length of the luminal portion 222 as well as the length and position of the sealing portion on the catheter. The sealing region on the luminal portion 222 can be located a distance from the distal tip of the catheter that is at least about 40 cm, 45 cm, 50 cm, 55 cm, 60 cm, 65 cm, 70 cm, up to about 75 cm from the distal tip of the catheter.

Use of the term "seal" in the context of the catheter and the guide sheath refers to a condition where upon application of an aspiration force fluid is prevented from substantially passing from one side of the seal to the other. For example, the low clearance between the OD of the catheter and the ID of the sheath at the seal can prevent, upon application of aspiration pressure through the system, substantial passage of blood between outer surface of the catheter and the inner surface of the sheath and thereby create a seal. The seal does not necessarily mean the entire catheter system is sealed. For example, even when the catheter is "sealed" with the sheath, blood can still be aspirated into the lumen of the catheter and through the guide sheath (at least until "corking" of the distal end of the catheter 200 where a full seal of the entire system may occur).

The catheter 200 can telescope relative to the sheath (and/or relative to another catheter 200) such that the distal end of the distal luminal portion 222 can reach cerebrovascular targets within, for example, the M1, M2 regions while the proximal end of the distal luminal portion 222 remains proximal to or below the level of severe turns along the path of insertion. For example, the entry location of the catheter system can be in the femoral artery and the target embolus can be distal to the right common carotid artery (RCC), such as within the M1 segment of the middle cerebral artery on the right side. The proximal end region of the distal luminal portion 222 (e.g. where the sealing element is located and/or where the material transition to the proximal control element 230 occurs) can remain within a vessel that is proximal to severely tortuous anatomy: the carotid siphon, the right common carotid RCC, the brachiocephalic trunk BT, the take-off of the brachiocephalic artery from the aortic arch, the aortic arch AA as it transitions from the descending aorta DA. The descending aorta DA is a consistently straight segment in most anatomies. FIG. 1C illustrates the aortic arch AA, which separates the ascending aorta AscA and descending aorta DA. The distal-most carotid from a femoral access point is the right common carotid RCC artery, which takes off from the brachiocephalic trunk BT (or the left common carotid, which takes off from the same brachiocephalic trunk BT in some patients—the so-called "bovine anatomy"). The distal luminal portion 222 may have a length that, when inserted into the RCC, is configured to extend from a target location in the M1 or M2 regions down to the brachiocephalic trunk BT, or down to the level of the aortic arch AA, or down to the descending aorta DA, which is sometimes referred to herein as being "below the takeoff" of the brachiocephalic trunk BT. This avoids inserting the stiffer proximal control element 230, or the material transition between the stiffer proximal control element 230 and the distal luminal portion 222, from taking the turn of the aortic arch or the turn of the brachiocephalic take-off, which can often be very severe. The turn of the aortic arch and the takeoff of the brachiocephalic are often the first severe turns catheters are likely to traverse as they ascend to the brain via the RCC artery. The less flexible portions of the catheter segment are able to avoid the regions of increased tortuosity near the level of the internal carotid artery. The distal luminal portion 222 can transition in flexibility towards the proximal region to approach the flexibility of the stiffer proximal control element 230. The distal end of the catheter can be used to target the left cerebral circulation while the proximal control element 230 of the catheter 200 as well as the material transitions of the distal luminal portion 222 near the proximal control element 230 remain below the level of tortuosity of the brachiocephalic turn (e.g., within the aorta, proximal to the take-off of the left common carotid artery, and preferably within the descending aorta DA). Similarly, the sealing region or a majority of the sealing region between the distal luminal portion 222 and the sheath preferably remains proximal to these severe turns.

In some implementations, the distal luminal portion 222 can have a length that allows the distal end of the distal luminal portion 222 to reach distal to the carotid siphon into the cerebral portion of the internal carotid artery while at the same time the proximal end of the distal luminal portion 222 (e.g. where it transitions to the proximal control element 230 as will be described in more detail below) remains within the aorta proximal to the take-off of the brachiocephalic trunk BT, for example within the descending aorta DA (see FIG. 2C). In this implementation, the distal luminal portion can be between about 35 cm and 75 cm in length, for example, between 45 cm-70 cm, or 65 cm long.

The attachment region between the more rigid, proximal control element 230 and the more flexible, distal luminal portion 222 creates a transition in material and flexibility that can be prone to kinking. Thus, it is preferable to avoid advancing the attachment region into extreme curvatures. For example, the distal luminal portion 222 can have a length that allows the point of attachment to be advanced no further than the first turn of the carotid siphon, or no further than the brachiocephalic artery take-off 610, or nor further than the aortic arch AA, or no further than the descending aorta DA when the catheter is advanced from a femoral access site. In some implementations, the distal luminal portion 222 has a length sufficient to allow the point of attachment to remain within the descending aorta DA while still accessing M1 or M2 regions of the neurovasculature. Locating the material transition within the extreme turn of the brachiocephalic take-off BT from the aortic arch AA is generally avoided when the distal luminal portion 222 has a length that is between about 35 cm to about 75 cm, or 45 cm-70 cm, or 65 cm.

A seal can be created at and/or within the overlap region 348 between the distal luminal portion 222 and the sheath body 402. It can be generally desirable to position the sealing between the distal luminal portion 222 and the sheath body 402 outside of extreme curvatures of the neurovasculature. In some implementations, the distal luminal portion 222 can have a length that allows for the distal end of the distal luminal portion 222 to extend distal to the carotid siphon into the cerebral portion of the internal carotid artery while at the same time the sealing region with the sheath body 402 remains proximal to the brachiocephalic takeoff BT, the aortic arch AA, or within the descending aorta DA. In this implementation, the length can be between about 35 cm to about 75 cm, about 40 cm to about 65 cm, or greater than 40 cm up to a length that is less than the working length of the sheath body 402.

Figure 2C:
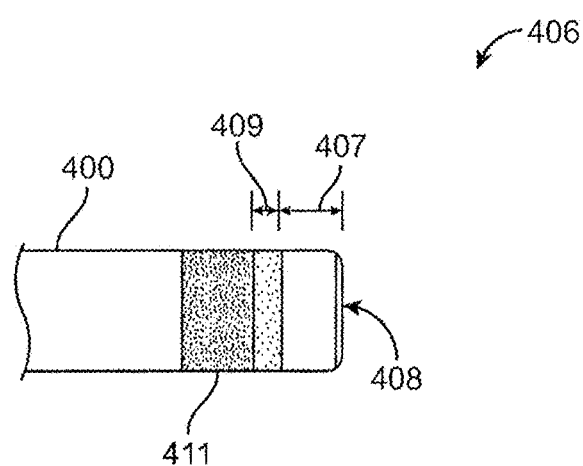
FIG. 2C is a detail view of FIG. 2A taken at circle C-C.
Figure 2D:
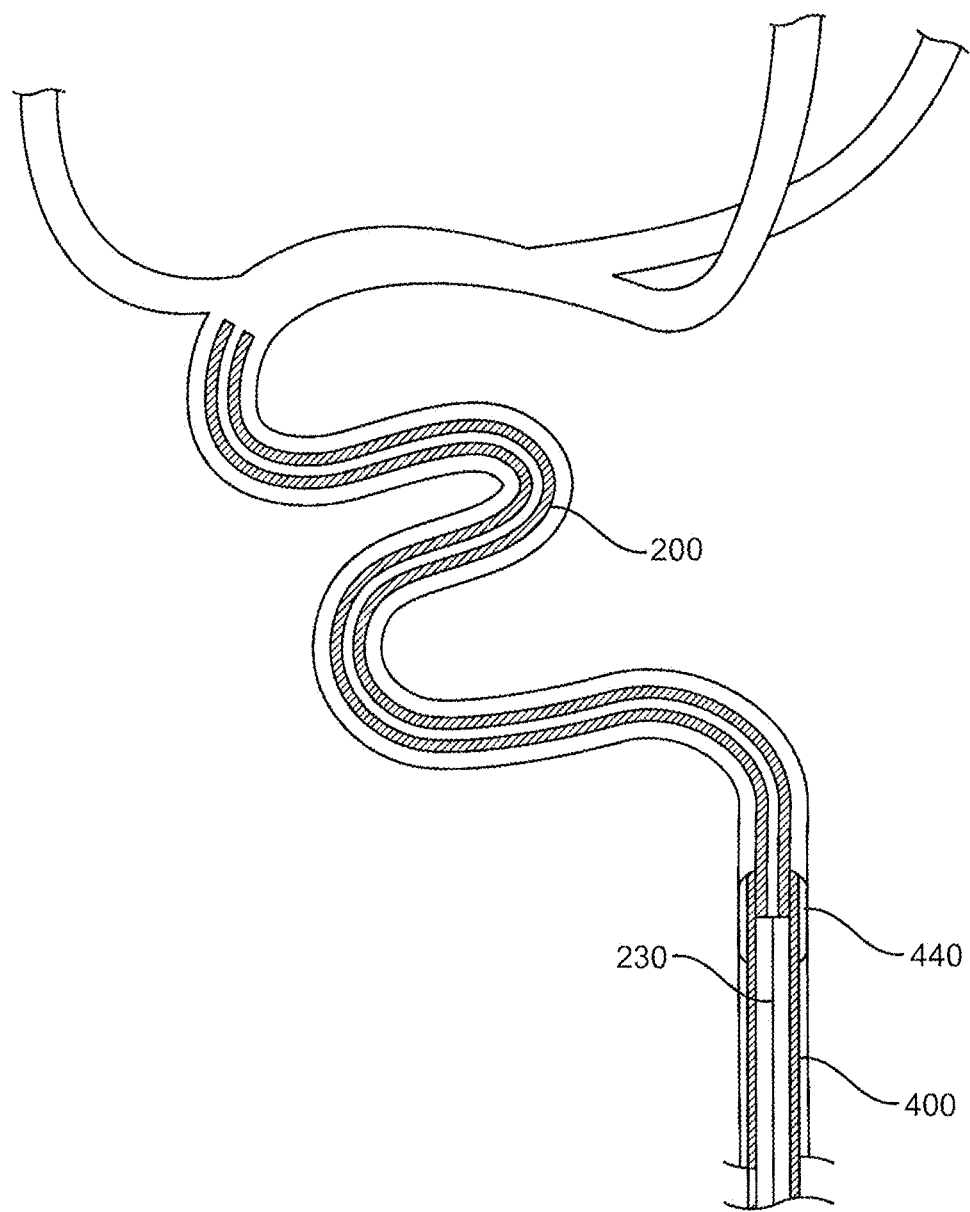
FIG. 2D illustrates an implementation of an arterial access device having a distal occlusion balloon.

With respect to FIG. 2C, the unreinforced region 407 of the distal tip 406 of the sheath 400 can have a length that allows it to provide sufficient sealing force onto the outer surface of the catheter 200 upon application of a negative pressure. The distal luminal portion 222 of the catheter 200 used with this implementation of sheath 400 can have a length that is shorter than 60 cm, shorter than 50 cm, shorter than 40 cm, shorter than 35 cm, shorter than 30 cm to about 10 cm. For example, the distal luminal portion 222 of the catheter 200 when used with a sheath 400 having an unreinforced region 407 configured for sealing against the outer diameter of the catheter 200 can be less than about 30 cm, for example, between about 10 cm and about 30 cm.

Sealing within the overlap region 348 can be due to the small difference in inner and outer diameters. The proximal end region of the distal luminal portion 222 can have a step-up in outer diameter (e.g. increased wall thickness) providing a region of localized sealing with the inner diameter of the guide sheath. Additionally, or alternatively, the localized sealing can be due to an additional sealing element positioned on an external surface of the distal luminal portion or an inner surface of the sheath body. A sealing element can include a stepped-up diameter or protruding feature in the overlap region. The sealing element can include one or more external ridge features. The one or more ridge features can be compressible when the luminal portion is inserted into the lumen of the sheath body. The ridge geometry can be such that the sealing element behaves as an O-ring, quad ring, or other piston seal design. The sealing element can include one or more inclined surfaces biased against an inner surface of the sheath body lumen. The sealing element can include one or more expandable members actuated to seal. The inflatable or expandable member can be a balloon or covered braid structure that can be inflated or expanded and provide sealing between the two devices at any time, including after the catheter is positioned at the desired site. Thus, no sealing force need be exerted on the catheter during positioning, but rather applied or actuated to seal after the catheter is positioned. The sealing element can be positioned on the external surface of the distal luminal portion, for example, near the proximal end region of the distal luminal portion and may be located within the overlap region. More than a single sealing element can be positioned on a length of the catheter.

Figure 15A:
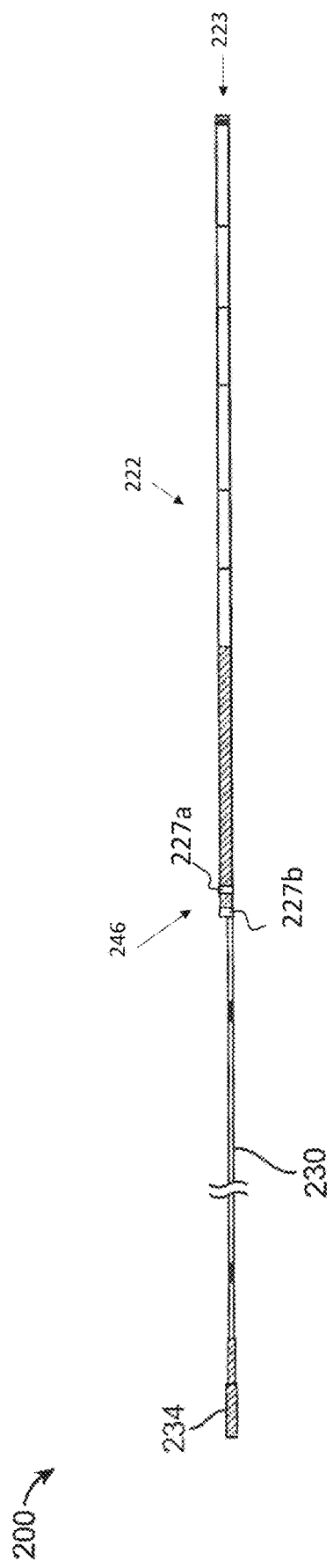
FIG. 15A illustrates a side view of an implementation of a catheter having non-circular regions.
Figure 15B:
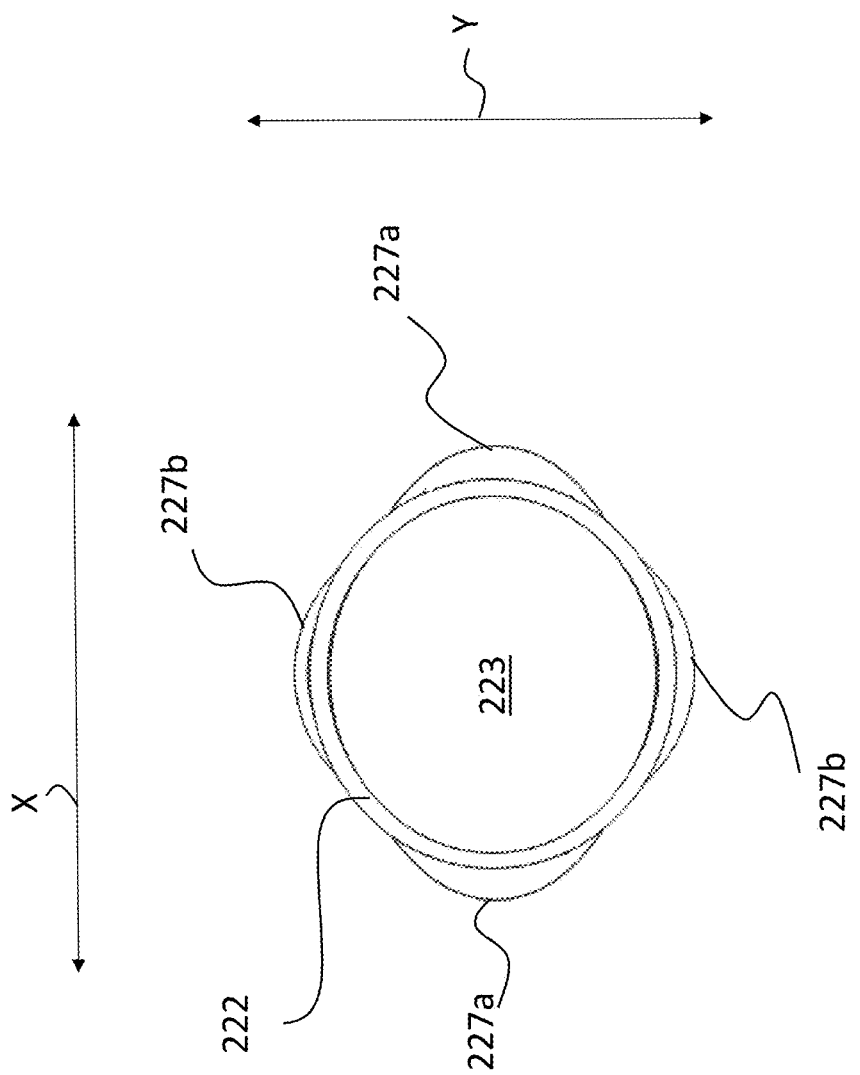
FIG. 15B shows a distal end view of the catheter of FIG. 15A.

It is further contemplated that the overlap region 348 may be embodied as different shapes. For example, the outer diameter of the distal luminal portion 222 within the overlap region 348 (e.g., a proximal region of the distal luminal portion 222) may be non-circular in shape, such that one axis of the distal luminal portion 222 is longer than another axis of the distal luminal portion 222. The lumen 223 of the distal luminal portion 222 within this region may have a circular cross-section or may have a non-circular cross-section where one axis is longer than the other axis. FIG. 15A shows a side view of an implementation of a catheter 200 having a distal luminal portion 222. FIG. 15B is a schematic distal end view of the catheter 200 of FIG. 15A. A proximal tubular region 246 of the distal luminal portion 222 may include two or more non-circular regions 227*a*, 227*b*. The non-circular regions 227*a*, 227*b* can be separated from one another along a longitudinal axis of the catheter 200 as shown in FIG. 15A or can abut against one another along the longitudinal axis of the catheter 200. Each non-circular region 227*a*, 227*b* has a short axis and a long axis. The long axes of the non-circular regions 227*a*, 227*b* can be offset from the other. FIG. 15B shows non-circular region 227*a* has a short axis along axis Y and a long axis along axis X whereas non-circular region 227*b* is offset 90 degrees around the circumference of the luminal portion 222 and has a short axis along axis X and a long axis along axis Y. The offset creates a continuous seal within the lumen of the guide sheath.

The additional sealing element of the distal luminal portion 222 can be a cup seal, a balloon seal, or a disc seal formed of a soft polymer positioned around the exterior of the distal luminal portion near the overlap region to provide additional sealing. The sealing element can be a thin-wall tubing with an outer diameter that substantially matches the inner diameter of the sheath body lumen. The tubing can be sealed on one end to create a cup seal or on both ends to create a disc or balloon seal. The balloon seal can include trapped air that creates a collapsible space. One or more slits can be formed through the wall tubing such that the balloon seal can be collapsible and more easily passed through an RHV. The balloon seal need not include slits for a less collapsible sealing element that maintains the trapped air. The sealing element can be tunable for sheath fit and collapse achieved.

In some implementations, the system can include one or more features that restrict extension of the catheter 200 relative to the sheath 400 to a particular distance such that the overlap region 348 achieved is optimum and/or the catheter 200 is prevented from being over-inserted. For example, a tab can be positioned on a region of the catheter 200 such that upon insertion of the catheter 200 through the sheath 400 a selected distance, the tab has a size configured to abut against the port through which the catheter 200 is inserted to prevent further distal extension of the catheter 200 through the sheath 400. A tab can also be positioned on a region of the catheter advancement element 300 to ensure optimum extension of the catheter advancement element 300 relative to the distal end of the catheter 200 to aid in advancement of the catheter 200 into the intracranial vessels.

Again, with respect to FIG. 3, the proximal control element 230 is configured to move the distal luminal portion 222 in a bidirectional manner through the working lumen of the guide sheath 400 such that the distal luminal portion 222 can be advanced out of the guide sheath 400 into a target location for treatment within the target vessel. In some implementations and as shown in FIG. 3, the proximal control element 230 of the catheter 200 can have a smaller outer diameter than the outer diameter of the distal luminal portion 222 forming a proximal spine or tether to the catheter 200. A smaller outer diameter for the proximal control element 230 than the outer diameter of the distal luminal portion 222 allows for the larger diameter working lumen of the sheath 400 to maintain greater aspiration forces than would otherwise be provided by the smaller diameter luminal portion 222 of the catheter 200 or allow for the delivery of working devices through the lumen with less frictional forces. The markedly shorter length of the luminal portion 222 results in a step-up in luminal diameter between the luminal portion 222 contiguous with the working lumen providing a markedly increased radius and luminal area for delivery of a working device and/or aspiration of the clot, particularly in comparison to other systems where the aspiration lumen runs along the entire inner diameter of the aspiration catheter. More particularly, the combined volume of the luminal area of the catheter 200 and the luminal area of the working lumen proximal to the distal luminal portion 222 is greater than the luminal area of the large bore catheter along the entire length of the system. Thus, the likelihood of removing the embolus during a single aspiration attempt may be increased. More particularly, the stepped-up luminal diameter along the proximal control element 230 may enable a greater aspiration force to be achieved resulting in improved aspiration of the embolus. Further, this configuration of the catheter 200 and proximal control element 230 greatly speeds up the time required to retract and re-advance the catheter 200 and/or working devices through the working lumen out the distal opening 408. The proximal control element 230 of the catheter 200 has a length and structure that extends through the working lumen of the sheath-guide 400 to a proximal end of the system 100 such that the proximal control element 230 can be used to advance and retract the catheter 200 through the working lumen. The proximal control element 230 of the catheter 200, however, takes up only a fraction of the luminal space of the system 100 resulting in increased luminal area for aspiration and/or delivery of working devices. The stepped-up luminal diameter also increases the annular area available for forward flushing of contrast, saline, or other solutions while devices such as microcatheters or other devices may be coaxially positioned in the luminal portion 222 of the catheter 200 and/or the working lumen. This can increase the ease and ability to perform angiograms during device navigation.

In an implementation, the distal luminal portion 222 of the catheter 200 is constructed to be flexible and lubricious, to be able to safely navigate to the target location. The distal luminal portion 222 can be kink resistant and collapse resistant when subjected to high aspiration forces to be able to effectively aspirate a clot. The luminal portion 222 can have increasing flexibility towards the distal end with smooth material transitions along its length to prevent any kinks, angulations or sharp bends in its structure, for example, during navigation of severe angulations such as those having 90° or greater to 180° turns, for example at the aorto-iliac junction, the left subclavian artery LSA take-off from the aorta AA, the takeoff of the brachiocephalic (innominate) artery BT from the ascending aorta AscA and many other peripheral locations just as in the carotid siphon. The distal luminal portion 222 can transition from being less flexible near its junction with the proximal control element 230 to being more flexible at the distal-most end. For example, a first portion of the distal luminal portion 222 can be formed of a material having a material hardness of 72D along a first length, a second portion can be formed of a material having a material hardness of 55D along a second length, a third portion can be formed of a material such as Pebax or MX1205 having a material hardness of 40D along a third length, a fourth portion can be formed of a material having a material hardness of 35D along a fourth length, a fifth portion can be formed of a material having a material hardness of 25D along a fifth length, a sixth portion can be formed of a material such as Tecoflex having a material hardness of 85A along a sixth length, and a final distal portion of the catheter can be formed of a material such as Tecoflex having a material hardness of 80A. In some implementations, the final distal portion of the distal luminal portion 222 of the catheter 200 can be formed of a material such as Tecothane having a material hardness of 62A. Thus, the distal luminal portion 222 transitions from being less flexible near its junction with the proximal control element 230 to being more flexible at the distal-most end where, for example, a distal tip of the catheter advancement element 300 can extend from the distal end of the catheter 200. Other procedural catheters described herein can have a similar construction providing a variable relative stiffness that transitions from the proximal end towards the distal end of the catheter as will be described elsewhere herein. The change in flexibility from proximal to distal end of the distal luminal portion 222 can be achieved by any of a variety of methods.

The distal luminal portion 222 can include two or more layers. In some implementations, the distal luminal portion 222 includes an inner lubricious liner, a reinforcement layer, and an outer jacket layer, each of which will be described in more detail.

The lubricious inner liner can be a PTFE liner, with one or more thicknesses along variable sections of flexibility. The PTFE liner can be a tubular liner formed by dip coating or film-casting a removable mandrel, such as a silver-plated copper wire as is known in the art. Various layers can be applied having different thicknesses. For example, a base layer of etched PTFE can be formed having a thickness of about 0.005". A second, middle layer can be formed over the base layer that is Tecoflex bSG-80A having a thickness of about 0.0004". A third, top layer can be formed over the middle layer that is Tecoflex SG-93A having a thickness of about 0.0001" or less. A reinforcement layer and/or reinforcement fiber can be applied to the inner liner, followed by the outer jacket layer and/or additional outer coating prior to removing the mandrel by axial elongation.

The reinforcement layer is a generally tubular structure formed of, for example, a wound ribbon or wire coil or braid. The material for the reinforcement structure may be stainless steel, for example 304 stainless steel, Nitinol, cobalt chromium alloy, or other metal alloy that provides the desired combination of strengths, flexibility, and resistance to crush. In some implementations, the distal luminal portion 222 has a reinforcement structure that is a Nitinol ribbon wrapped into a coil. For example, the coil reinforcement can be a tapered ribbon of Nitinol set to a particular inner diameter (e.g. 0.078" to 0.085" inner diameter) and having a pitch (e.g. between 0.012" and 0.016"). The ribbon can be 304 stainless steel (e.g. about 0.012"×0.020"). The coil can be heat-set prior to transferring the coil onto the catheter. The pitch of the coil can increase from proximal end towards distal end of the distal luminal portion 222. For example, the ribbon coils can have gaps in between them and the size of the gaps can increase moving towards the distal end of the distal luminal portion 222. For example, the size of the gap between the ribbon coils can be approximately 0.016" gap near the proximal end of the distal luminal portion 222 and the size of the gap between the ribbon coils near the distal end can be larger such as 0.036" gap. This change in pitch provides for increasing flexibility near the distal-most end of the distal luminal portion 222. The distal luminal portion 222 can additionally incorporate one or more reinforcement fibers (see FIGS. 8B-8C) configured to prevent elongation of the coils, as will be described in more detail below. The reinforcement structure can include multiple materials and/or designs, again to vary the flexibility along the length of the distal luminal portion 222.

The outer jacket layer may be composed of discreet sections of polymer with different durometers, composition, and/or thickness to vary the flexibility along the length of the distal luminal portion 222.

At least a portion of the outer surface of the catheter 200 can be coated with a lubricious coating such as a hydrophilic coating. In some implementations, the coating may be on an inner surface and/or an outer surface to reduce friction during tracking. The coating may include a variety of materials as is known in the art. The proximal control element 230 may also be coated to improve tracking through the working lumen. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, HYDAK coatings (e.g. B-23K, HydroSleek), and the like, and mixtures and combinations thereof. Hydrophilic polymers may be blended among themselves or with formulated amounts of water insoluble compounds (including some polymers) to yield coatings with suitable lubricity, bonding, and solubility.

In some implementations, the distal luminal portion 222 includes two or more layers. In some implementations, the distal luminal portion 222 includes an inner lubricious liner, a reinforcement layer, and an outer jacket layer. The outer jacket layer may be composed of discreet sections of polymer with different durometers, composition, and/or thickness to vary the flexibility along the length of the distal luminal portion 222. In an implementation, the lubricious inner liner is a PTFE liner, with one or more thicknesses along variable sections of flexibility. In an implementation, the reinforcement layer is a generally tubular structure formed of, for example, a wound ribbon or wire coil or braid. The material for the reinforcement structure may be stainless steel, for example 304 stainless steel, nitinol, cobalt chromium alloy, or other metal alloy that provides the desired combination of strengths, flexibility, and resistance to crush. In an implementation, the reinforcement structure includes multiple materials and/or designs, again to vary the flexibility along the length of the distal luminal portion 222. In an implementation, the outer surface of the catheter 200 is coated with a lubricious coating such as a hydrophilic coating. The proximal control element 230 may also be coated to improve tracking through the working lumen. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof.

Again, with respect to FIGS. 2A-2B, the distal luminal portion 222 of the catheter 200 can have a plurality of radiopaque markings. A first radiopaque marker 224*a* can be located near the distal tip region to aid in navigation and proper positioning of the tip under fluoroscopy. Additionally, a proximal region of the catheter 200 may have one or more proximal radiopaque markers 224*b* so that the overlap region 348 can be visualized as the relationship between a radiopaque marker 411 on the guide sheath 400 and the radiopaque marker 224*b* on the catheter 200. The proximal region of the catheter 200 may also have one or more radiopaque markings providing visualization, for example, of the proximal opening into the single lumen of the catheter as will be described in more detail below. In an implementation, the two radiopaque markers (marker 224*a* at distal tip and a more proximal marker 224*b*) are distinct so as to minimize confusion of the fluoroscopic image, for example the catheter proximal marker 224*b* may be a single band and the marker 411 on the guide sheath 400 may be a double band and any markers on a working device delivered through the distal access system can have another type of band or mark. The radiopaque markers 224 of the distal luminal portion 222, particularly those near the distal tip region navigating extremely tortuous anatomy, can be relatively flexible such that they do not affect the overall flexibility of the distal luminal portion 222 near the distal tip region. The radiopaque markers 224 can be tungsten-loaded or platinum-loaded markers that are relatively flexible compared to other types of radiopaque markers used in devices where flexibility is not paramount. In some implementations, the radiopaque marker can be a band of tungsten-loaded PEBAX having a durometer of 35D.

Figure 8A:
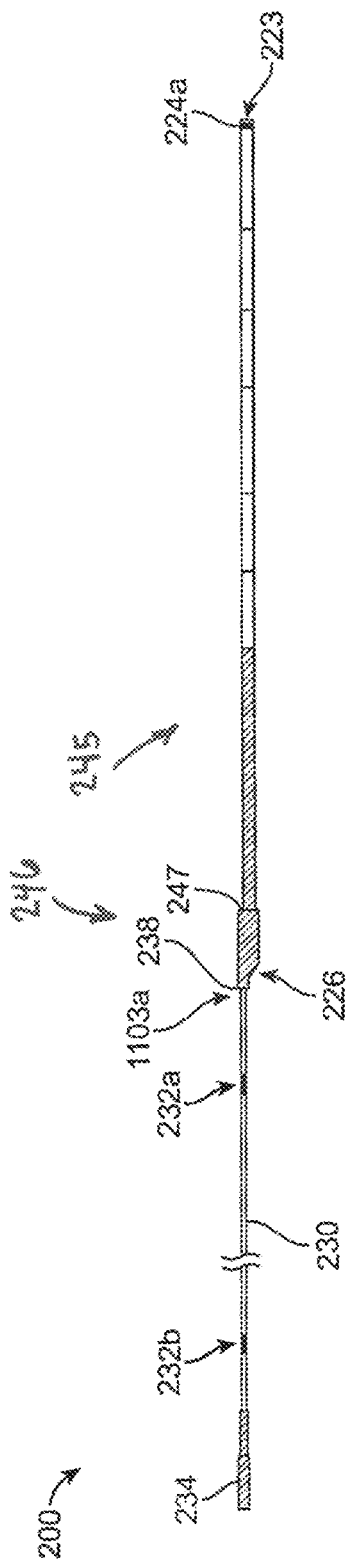
FIG. 8A is a side view of an implementation of a catheter.
Figure 8B:
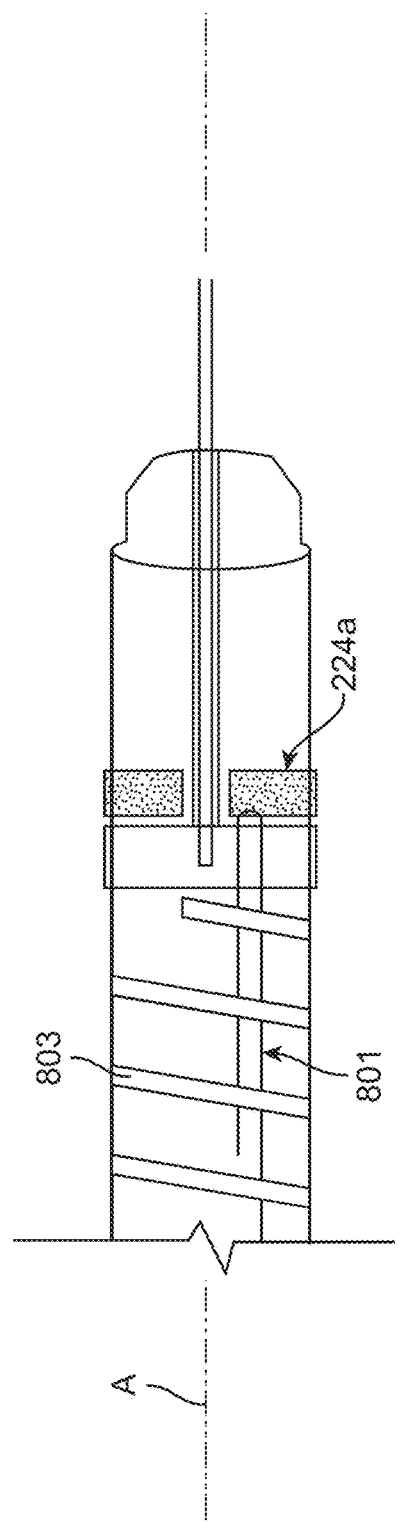
FIG. 8B is a schematic cut-away view of the distal end region of the catheter of FIG. 8A.
Figure 8C:
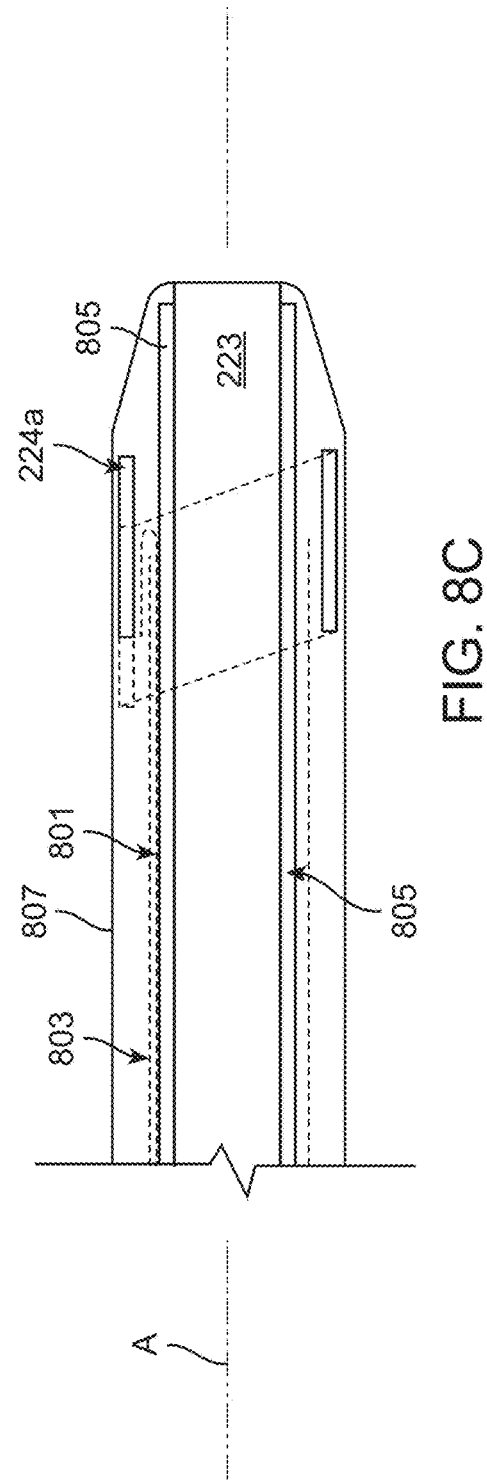
FIG. 8C is a schematic cross-sectional view of the distal end region of the catheter of FIG. 8A.

As best shown in FIGS. 8B-8C, at least one reinforcement fiber 801 can be incorporated within a wall of the distal luminal portion 222 to prevent elongation of a coiled reinforcement layer 803. The fiber 801 can be positioned between the liner layer 805 and the reinforcement layer 803. The fiber 801 can extend along the longitudinal axis A of the catheter 200 from a proximal end region of the distal luminal portion 222 to a distal end region of the portion 222. The proximal end of the fiber 801 can be coupled to a region of the distal luminal portion 222 near where it couples to the proximal control element 230. A distal end of the fiber 801 can terminate near the distal end of the distal luminal portion 222. The distal end of the fiber 801 can be captured between the distal marker band 224*a* and an end of the reinforcement layer 803. The distal marker band 224*a* can be fully encapsulated between the inner liner 805 and the outer jacket 807. In some implementations, the distal end of the fiber 801 extends distal to the last coil of the reinforcement layer 803 running under the marker band 224*a* and then looping around the band 224*a* back in a proximal direction. The free end of the fiber 801 is thereby captured under the reinforcement layer 803 and the marker band 224*a*. The reinforcement fiber 801 thus terminates at the location the reinforcement layer 803 terminates thereby leaving a length of between about 10 cm-12 cm of the unreinforced distal-most tip region. The catheter 200 can include a plurality of reinforcement fibers 801 extending longitudinally along the distal luminal portion 222, such as two, three, four, or more fibers 801 distributed around the circumference of the portion 222 and aligned parallel with one another and with the longitudinal axis A of the catheter 200. The reinforcement fiber 801 may also terminate at a more distal location or at a more proximal location than the location of the distal terminal marker 224*a*. The material of the reinforcement fiber 801 can vary, including but not limited to various high tenacity polymers like polyester, PEEK, and other similar materials.

Figure 9A:
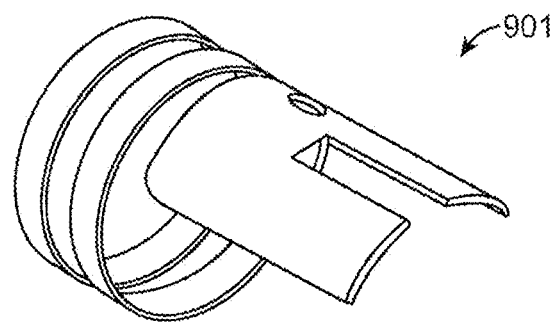
FIGS. 9A-9C are various views of a proximal extension connector.
Figure 9B:
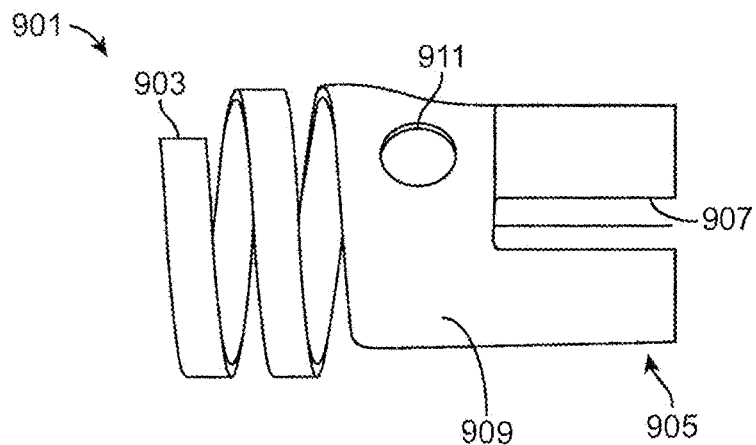
Figure 9C:
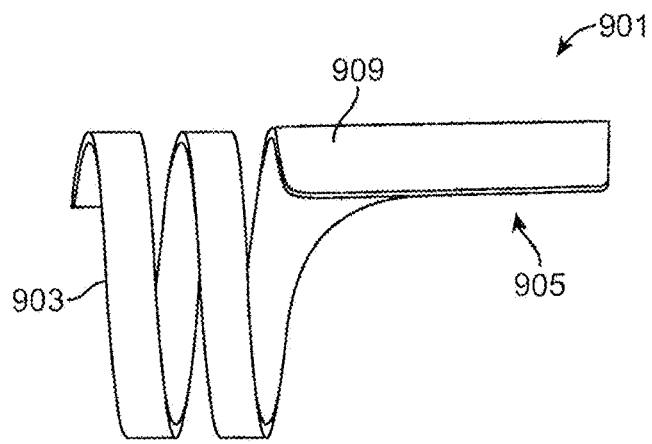

The distal luminal portion 222 of the catheter 200 can have a proximal control element 230 coupled near a proximal opening into the single lumen of the distal luminal portion 222. The distal luminal portion 222 and the proximal control element 230 can be attached to one another by a coupling band 901 (see FIGS. 9A-9C). A proximal end 905 of the coupling band 901 can attach to a distal end of the proximal control element 230 and a distal end of the coupling band 901 can attach to the distal luminal portion 222. The proximal end 905 of the coupling band 901 includes a slot 907 configured to be welded with the proximal control element 230 of the catheter 200. The distal end of the coupling band 901 can be cut to form a plurality of spirals 903. These spirals 903 are configured to intersperse with the coils of the reinforcement layer 803 at the proximal end region of the distal luminal portion 222. The size of the gap between the spirals 903 of the coupling band 901 can be substantially similar to the size of the gap between the coils of the reinforcement layer 803 such that they can neatly intersperse with one another without creating any localized areas of increased wall thickness due to overlap. The thickness of the spirals 903 can, but need not, be similar to the thickness of the ribbon forming the reinforcement layer 803. For example, the coiled reinforcement layer 803 can be formed of a Nitinol ribbon having a thickness of about 0.003". The coupling band 901 can have a wall thickness that is about 0.003" such that the spirals 903 and the coils of the reinforcement layer 803 can be similar in material thickness. This similarity in material thickness between the coils and the spirals 903 contribute to a generally uniform outer profile that can be kept to a minimum and avoid creating a substantially increased wall thickness in this coupling region. A low-profile proximal end of the distal luminal portion 222 aids in maximizing the inner diameter while keeping the outer diameter as small as possible, for example, such that the inner diameter of the guide sheath to a minimum (e.g. less than about 0.113" or about 0.107"). The coupling band 901 can include an aperture 911 through middle region 909 that is configured to receive a proximal end of the reinforcement fiber 801 extending longitudinally through the distal luminal portion 222. The region of overlap between the distal end of the proximal control element and the distal luminal portion 222 can vary, but can be at least about 5 mm, at least about 7 mm, at least about 10 mm to provide a smooth and even transition. The overlap between the proximal control element and the distal luminal portion 222 may be about 5 mm up to about 15 mm.

As mentioned, the distal end of the proximal control element 230 can be welded to the proximal end 905 of the coupling band 901. In some implementations, the distal end region of the proximal control element 230 is skived in places and is flat in other places. The proximal control element 230 can be a stainless steel ribbon (e.g. 0.012"× 0.020" or 0.014"×0.020" along a majority of its length). A distal end region of the proximal control element 230 can have a discontinuous taper that allows for the thickness of the ribbon to transition from the thickness of 0.012" or 0.014" down to a thickness that matches or is not significantly different from a thickness of the spirals 903 on the coupling band 901 that is attached to a proximal end region of the distal luminal portion 222. The discontinuous taper can include a flat length bound on proximal and distal ends by a tapered length. The flat length allows for a more uniform, minimum material thickness between the distal luminal portion 222 and the proximal control element 230 that avoids introducing weak points that are more prone to kinking. For example, the distal end region of the proximal control element 230 can have a first tapered length that transitions in thickness from 0.012" to a thickness of 0.008" and a second tapered length that transitions from the flat length thickness down to about 0.003". In other implementations, the distal end region of the proximal control element 230 can have a first tapered length that transitions in thickness from 0.014" to a thickness of 0.010" and a second tapered length that transitions from the flat length thickness down to about 0.003". The spirals 903 of the coupling band 901 can have a thickness matches this terminal thickness of the proximal control element 230. The lengths of the tapered and flat portions can vary. In some implementations, the first tapered length can be approximately 0.12 cm, the flat length can be approximately 0.2 cm, and the second tapered length can be approximately 0.15 cm. The uniform thickness along this flat length provides for a useful target in terms of manufacturing the catheter. The catheter need not incorporate a ribbon proximal control element 230 and can have any of a variety of configuration as described elsewhere herein.

As mentioned previously, the proximal control element 230 is configured to allow distal advancement and proximal retraction of the catheter 200 through the working lumen of the guide sheath 400 including passage out the distal opening 408. In an implementation, the length of the proximal control element 230 is longer than the entire length of the guide sheath 400 (from distal tip to proximal valve), such as by about 5 cm to 15 cm. The length of the body 402 can be in the range of 80 to 90 cm or up to about 100 cm or up to about 105 cm and the length of the proximal control element 230 can be between 90-100 cm.

Again with respect to FIG. 3, the proximal control element 230 can include one or more markers 232 to indicate the overlap between the distal luminal portion 222 of the catheter 200 and the sheath body 402 as well as the overlap between the distal luminal portion 222 of the catheter 200 and other interventional devices that may extend through the distal luminal portion 222. At least a first mark 232a can be an RHV proximity marker positioned so that when the mark 232a is aligned with the sheath proximal hemostasis valve 434 during insertion of the catheter 200 through the guide sheath 400, the catheter 200 is positioned at the distal-most position with the minimal overlap length needed to create the seal between the catheter 200 and the working lumen. At least a second mark 232b can be a Fluoro-saver marker that can be positioned on the control element 230 and located a distance away from the distal tip of the distal luminal portion 222. In some implementations, a mark 232 can be positioned about 100 cm away from the distal tip of the distal luminal portion 222.

The proximal control element 230 can include a gripping feature such as a tab 234 on the proximal end to make the proximal control element 230 easy to grasp and advance or retract. The tab 234 can couple with one or more other components of the system as will be described in more detail below. The proximal tab 234 can be designed to be easily identifiable amongst any other devices that may be inserted in the sheath proximal valve 434, such as guidewires or retrievable stent device wires. A portion of the proximal control element 230 and/or tab 234 can be colored a bright color, or marked with a bright color, to make it easily distinguishable from guidewire, retrievable stent tethers, or the like. Where multiple catheters 200 are used together in a nesting fashion to reach more distal locations within the brain, each proximal control element 230 and/or tab 234 can be color-coded or otherwise labeled to clearly show to an operator which proximal control element 230 of which catheter 200 it is coupled to. The proximal portion 366 of the catheter advancement element 300 can also include a color to distinguish it from the proximal control element 230 of the catheter 200.

The tab 234 can be integrated with or in addition to a proximal hub coupled to a proximal end of the control element 230. For example, as will be described in more detail below, the proximal control element 230 can be a hypotube having a lumen. The lumen of the hypotube can be in fluid communication with the proximal hub at a proximal end of the control element 230 such that aspiration forces and/or fluids can be delivered through the hypotube via the proximal hub. The proximal control element 230 can also be a solid element and need not include a lumen to direct aspiration forces to the distal end of the catheter 200.

The proximal control element 230 can be configured with sufficient stiffness to allow advancement and retraction of the distal luminal portion 222 of the catheter 200, yet also be flexible enough to navigate through the cerebral anatomy as needed without kinking. The configuration of the proximal control element 230 can vary. In some implementations, the proximal control element 230 can be a tubular element having an outer diameter that is substantially identical to the outer diameter of the distal luminal portion 222 similar to a typical catheter device. In other implementations, the outer diameter of the proximal control element 230 is sized to avoid taking up too much luminal area in the lumen of the guide sheath 400 to provide a step-up in inner diameter for aspiration.

The proximal control element 230 can be a solid metal wire that is round, rectangular, trapezoid, D-shape, or oval cross-sectional shape. The proximal control element 230 can be a flattened ribbon of wire having a rectangular cross-sectional shape. The flattened ribbon of wire can also have square, rectangular, or other cross-sectional shape. The ribbon of wire can be curved into a circular, oval, c-shape, or quarter circle or other cross-sectional area along an arc. As such, an inner-facing surface of the ribbon can be substantially flat and an outer-facing surface of the ribbon (i.e. the surface configured to abut against an inner diameter of the access sheath through which it extends) can be substantially curved. The curvature of the surface can substantially match the curvature of the inner surface of the access sheath. The resulting cross-sectional shape of such a ribbon can be generally trapezoidal. The overall dimensions of the ribbon can vary depending on its cross-sectional shape and the size of the distal luminal portion. The 0.054" sized catheter 200 can have a proximal control element 230 that is trapezoidal or D-shaped in cross-section. The inner-facing, flat surface can have a width that is approximately 0.020" wide and in the case of the trapezoidal-shaped implementation, the outer-facing, curved surface can extend along an arc that is approximately 0.030" long. The 0.070" sized catheter 200 can have a proximal extension that is trapezoidal or D-shaped in cross-section, and the width of the inner-facing, flat surface is slightly greater, for example, approximately 0.025" and in the case of the trapezoidal-shaped implementation, the outer-facing, curved surface can extend along an arc that is approximately 0.040" long. The 0.088" sized catheter 200 can have a proximal extension that is trapezoidal or D-shaped in cross-section, and the width of the inner-facing, flat surface is approximately 0.035" and the outer-facing, curved surface of the trapezoidal-shaped implementation can extend along an arc that is approximately 0.050" long.

The proximal control element 230 can be a hollow wire having a lumen extending through it, such as a hypotube. The hypotube can have an oval or circular shape. In an implementation, the proximal control element 230 is a ribbon of stainless steel having dimensions of about 0.012"× 0.020". In an implementation, the proximal control element 230 is a ribbon of stainless steel having dimensions of about 0.014"×0.020". In an implementation, the proximal control element 230 is a round wire, with dimensions from 0.014" to 0.018". In another implementation, the proximal control element 230 is a ribbon with dimensions ranging from 0.010" to 0.015" thick, and 0.015" thick to 0.025" thick. In an implementation, the proximal control element 230 is a hypotube formed from a flattened ribbon of stiff material rolled into a tubular shape to have a lumen. In some implementations, the proximal control element 230 can be formed of a flattened ribbon of stainless steel and rolled into a hypotube such that the proximal control element 230 has a wall thickness of about 0.007", an inner diameter of about 0.004" and an outer diameter of about 0.018" before the hypotube is modified into an oval cross-sectional shape. The ovalized hypotube can maintain an inner diameter that is at least 0.001" along at least a first dimension and an outer diameter that is at least 0.015" along at least a first dimension. In an implementation, the proximal control element 230 material is a metal such as a stainless steel or nitinol as well as a plastic such as any of a variety of polymers.

In an implementation, the proximal control element 230 is a stainless steel hypotube having an oval cross-sectional shape. The oval tubular shape can increase the column strength, pushability and kink resistance of the proximal control element 230 for improved advancement through tortuous anatomy. The cross-sectional area of an oval hypotube minimizes the impact of the catheter 200 on movement of other tools through the working lumen of the sheath 400. The proximal control element 230 can have a rectangular cross-sectional shape without a lumen or the proximal control element 230 can be an ovalized hypotube proximal control element 230. The oval hypotube has less surface area compared to the rectangular-shaped ribbon allowing for a greater flow rate through the working lumen, for example, during application of aspirating forces. The materials, dimensions, and shape of the proximal control element 230 can be selected based on the materials, dimensions, and shape of the distal luminal portion 222. For example, the proximal control element 230 can be a rectangular ribbon of 340 stainless steel that is 0.012"×0.020" and the distal luminal portion 222 can have an inner diameter of about 0.054" to about 0.072". In a further implementation, the proximal control element 230 can be a rectangular ribbon of 340 stainless steel that is 0.014"×0.020" and the distal luminal portion 222 can have an inner diameter of about 0.088". The additional heft of the stainless steel ribbon 230 can be useful in advancing a larger inner diameter catheter without kinking.

The junction between the distal luminal portion 222 of the catheter 200 and the proximal control element 230 can be configured to allow a smooth transition of flexibility between the two portions so as not to create a kink or weak point. The smooth transition at the joint between the distal luminal portion 222 and the proximal control element 230 also allows for smooth passage of devices through the contiguous inner lumen created by the working lumen of the guide sheath 400 and the lumen 223 of the luminal portion 222 of the catheter 200. In an implementation, the distal luminal portion 222 has a transition section 226 near the proximal opening into the single lumen and where the luminal portion 222 couples to the proximal control element 230 near location 1103a (see FIG. 8A). The transition section 226 can have an angled cut such that there is no abrupt step transition from the working lumen of the guide sheath 400 to the inner lumen 223 of the catheter 200. The angled cut can be generally planer. In an alternate implementation, the angled cut is curved or stepped to provide a more gradual transition zone. The proximal end region of the distal luminal portion 222 can be angled in an oblique manner relative to a longitudinal axis of the catheter 200 such that the proximal end and proximal opening into the lumen are at an angle other than 90° to the longitudinal axis of the catheter 200, for example between approximately 0°, 5°, 10°, 15°, 20°, 25°, 30°, 35°, 40°, or 45° up to less than 90°. The proximal end region of the distal luminal portion 222 can also be aligned substantially perpendicular to the longitudinal axis of the catheter 200 such that the proximal end and proximal opening into the lumen are substantially 90° to the longitudinal axis of the catheter 200. Similarly, the distal end region of the distal luminal portion 222 can be angled in an oblique manner relative to a longitudinal axis of the catheter 200 such that the distal end and distal opening from the lumen 223 are at an angle other than 90° to the longitudinal axis of the catheter 200, for example between approximately 0°, 5°, 10°, 15°, 20°, 25°, 30°, 35°, 40°, or 45° up to less than 90°. The distal end region of the distal luminal portion 222 can also be aligned substantially perpendicular to the longitudinal axis of the catheter 200 such that the distal end and distal opening into the lumen are substantially 90° to the longitudinal axis of the catheter 200.

The proximal control element 230 can be coupled to a proximal end region of the catheter 200 and/or may extend along at least a portion of the distal luminal portion 222 such that the proximal control element 230 couples to the distal luminal portion 222 a distance away from the proximal end defining the proximal opening into the lumen, for example via the coupling band 901. The proximal control element 230 can be coupled to the distal luminal portion 222 by a variety of mechanisms including bonding, welding, gluing, sandwiching, stringing, tethering, or tying one or more components making up the proximal control element 230 and/or portion 222. The distal luminal portion 222 and the proximal control element 230 may be joined by a weld bond, a mechanical bond, an adhesive bond, or some combination thereof. In some implementations, the proximal control element 230 and luminal portion 222 are coupled together by sandwiching the proximal control element 230 between layers of the distal luminal portion 222. For example, the proximal control element 230 can be a hypotube or rod having a distal end that is skived, ground or cut such that the distal end can be laminated or otherwise attached to the layers of the catheter portion 222 near a proximal end region. The skive length of the proximal control element 230 can be about 7 mm and can incorporate a tungsten loaded Pebax strain relief along the length. The region of overlap between the distal end of the proximal control element 230 and the portion 222 can be at least about 1 cm. This type of coupling allows for a smooth and even transition from the proximal control element 230 to the luminal portion 222.

The transition section 226 of the distal luminal portion 222 can open up into a proximal tail 238 extending a length proximal to the transition section 226. In some implementations, the proximal tail 238 has a cross-sectional geometry that is substantially curved. For example, the proximal tail 238 can extend along an arc of the longitudinal axis of the catheter 200 between about 20 to about 90 degrees. In some implementations, the proximal tail 238 is curved to create a funnel-shape and aids in loading and reloading a catheter advancement element 300 into the lumen of the catheter 200. In other implementations, the edges of the proximal tail 238 curve such that the proximal tail 238 is not substantially flat. The curved shape can vary including a tear-drop shape that allows for a smooth transition and better loading/reloading of the catheter advancement element 300 into the lumen and avoids flat edges that can abut and catch the component as it is inserted. In other implementations, the proximal tail 238 is substantially flat. The proximal tail 238 can provide a smooth transition between distal luminal portion 222 and proximal control element 230 when the device is forced to bend. This can reduce the likelihood of kinking and facilitate pushing against resistance.

The dimensions of the proximal tail 238 can vary. The proximal tail 238 can be relatively wide compared to the width of the proximal control element 230 and, in turn, can have a greater length without negatively impacting the ability of other devices to insert through the proximal opening into the lumen at the transition region 226. In other implementations, the proximal tail 238, defined by a region that is unsupported by the coils of the reinforcement layer 803 and located proximal to the coupling band 901, can have a shorter length. The width of this proximal tail 238 can taper along this shorter length to a width of the proximal control element 230. The tapered shorter proximal tail 238 can mitigate issues with insertion of tools into the proximal opening. Generally speaking, wide proximal tails 238 can be longer than proximal tails 238 that taper down to the width of the proximal control element 230.

A proximal region of the distal luminal portion 222 can incorporate one or more markers to provide visualization under fluoro during loading/reloading of the catheter advancement element 300. For example, the proximal end region can include a region of Pebax (e.g. 35D) loaded with tungsten (80%) for radiopacity. In some implementations, the proximal tail 228 and/or the transition section 226 defining the proximal opening into the lumen of the luminal portion 222 can be coated or embedded with a radiopaque material such that the opening into the lumen can be fully visualized during use. The radiopaque material embedded in this proximal end region can create a step-up in outer diameter.

The distal end of the proximal control element 230 and/or the distal luminal portion 222 may have features that facilitate a mechanical joint during a weld, such as a textured surface, protruding features, or cut-out features. During a heat weld process, the features would facilitate a mechanical bond between the polymer distal luminal portion 222 and the proximal control element 230. For example, the proximal end of the distal luminal portion 222 can include a short mating sleeve 240 coupled to a proximal edge of the distal luminal portion 222. The sleeve 240 can include an inner lumen extending between a proximal opening 242 and a distal opening 241. The distal end of the proximal control element 230 can insert through the proximal opening 242 and within the inner lumen of the sleeve 240 to couple the proximal control element 230 to the distal luminal portion 222. In some implementations, the proximal control element 230 can couple with the distal luminal portion 222 such that a distal opening 231 of the hypotube forming the proximal control element 230 can communicate with the lumen 223 of the distal luminal portion 222, for example, through the distal opening 241 of the sleeve 240. The sleeve 240 can also provide transition between distal luminal portion 222 and proximal control element 230 similar to the proximal tail 238. The distal luminal portion 222 need not include a mating sleeve 240 to couple with the proximal control element 230. For example, the distal end of the proximal control element 230 can insert through a wall of the proximal tail 238 at the proximal end of the distal luminal portion 222. The distal end of the proximal control element 230 can extend along the length of the proximal tail 238 and along at least a length of the wall of the distal luminal portion 222.

The luminal portion 222 of the catheter 200 can have a uniform diameter or wall thickness from a proximal end to a distal end or the luminal portion 222 can have different outer diameters or wall thicknesses along its length. For example, the distal-most end of the distal luminal portion 222 can have a smaller outer diameter compared to a more proximal region of the distal luminal portion 222. FIG. 8A shows a distal luminal portion 222 having a distal tubular region or distal tube 245 having a smaller outer diameter and a proximal tubular region or proximal tube 246 have a larger outer diameter. The distal tube 245 transitions via a step-up 247 to the proximal tube 246. The inner diameters of distal tube 245 and the proximal tube 246 are substantially the same providing a smooth inner wall surface for the lumen 223. The outer diameter of the distal tube 245 may be smaller than the outer diameter of the proximal tube 246. The step-up 247 is formed by a transition in wall thickness between the distal tube 245 and the proximal tube 246. In some implementations, the outer diameter of the distal tube 245 can be about 0.080" to about 0.084" and the outer diameter of the proximal tube 246 can be about 0.087" to about 0.088". In other implementations, the outer diameter of the proximal tube 246 can be 0.106" to about 0.107". The relative lengths of the proximal and distal tubes 245, 246 may vary as described elsewhere herein. For example, the proximal tube 246 can create a proximal sealing zone that is a cylindrical segment having a length that is about 1 mm, 2 mm, 3 mm, 4 mm, 5 mm, up to about 10 mm, or 15 mm. The proximal sealing zone of the proximal tube 246 may have a larger OD compared to the OD of the distal tube. In some implementations, the distal tube may have an OD that is about 0.082", the proximal tube 246 at the proximal sealing zone may have an OD that is about 0.087". In other implementations, where the distal tube may have an OD that is about 0.102", and the proximal tube 246 at the proximal sealing zone may have an OD that is about 0.105".

At least a portion of the wall of the larger outer diameter proximal tube 246 can be discontinuous such that it includes a slit. The slit can extend a distance along the length of the proximal tube 246. The slit can extend from an edge of the proximal tube 246 at least about 2 cm of a length of the proximal tube 246. The slit can, but need not, extend along the entire length of the proximal tube 246 to the location of the step-up 247. Additionally, the proximal tube 246 can include more than one slit. The slit can be positioned in the larger diameter proximal tube 246 at a location opposite from where the distal end of the proximal control element 230 couples with the wall of the distal luminal portion 222. As such that distal end of the proximal control element 230 embedded within the wall of the proximal tube 246 lies opposite the slit. The slit can be positioned around the proximal tube 246 at another location.

The slit can allow for the proximal tube 246 to expand slightly such that the ends of the wall forming the slit separate forming a gap therebetween. For example, upon insertion of the catheter 200 through the working lumen of the sheath 400, the outer diameter can be received in a sliding fit such that at least an overlap region 348 remains. Upon application of an aspirational force through the working lumen, for example, by applying suction from a vacuum source coupled to the proximal end 403 of the guide sheath 400, the sealing provided at the overlap region 348 can be enhanced by a slight widening of the gap formed by the slit.

This slight expansion provides for better sealing between the outer diameter of the proximal tube 246 and the inner diameter of the working lumen of the sheath 400 because the outer surface of the walls of the catheter 200 can press against the inner surface of the working lumen creating a tight fit between the catheter 200 and the sheath 400. This improved sealing between the outer surface of the catheter 200 and the inner surface of the working lumen minimizes the seepage of blood from the vessel into the working lumen directly through the distal opening 408. Thus, the larger outer diameter of the proximal tube 246 in combination with the slit 236 can enhance sealing between the catheter 200 and the sheath 400 by accommodating for variations of sheath inner diameters. The slit can effectively increase the outer diameter of the proximal tube 246 depending on whether the walls forming the slit are separated a distance. The walls forming the slit can separate away from one another and increase a width of slit. The outer diameter of the proximal tube 246 including the increased width upon separation of the walls forming the slit can be the same size or larger than the inner diameter of the sheath through which the proximal tube 246 is inserted. This allows for a single catheter to be compatible with a larger range of inner diameters. In some implementations, the outer diameter of the proximal tube 246 can be 0.081" or about 0.100" when the walls forming the slit abut one another and no gap is present. The outer diameter of the proximal tube 246 can increase up to about 0.087" or up to about 0.106" when the walls forming the slit are separated a maximum distance away from one another. Additionally, the increased wall thickness of the proximal tube 246 allows for creating a more robust joint between the distal luminal portion 222 and the proximal control element 230 of the catheter.

Additionally, or alternatively, the distal tip 406 of the sheath 400 can include one or more features that improve sealing between the inner diameter of the working lumen of the sheath 400 and the outer diameter of the proximal end region of the catheter 200.

Catheter Advancement Element

The distal access system 100 can, but need not, include a catheter advancement element 300 for delivery of the catheter 200 to the distal anatomy. Similarly, the catheter advancement element 300 can be used together to advance other catheters besides the catheter 200 described herein. For example, the catheter advancement element 300 can be used to deliver commercially available catheters such as, but not limited to: Sofia, Sofia Flow Plus and Sofia Plus (MicroVention Terumo, Aliso Viejo, Calif.), AXS Vectra (Stryker Neurovascular, Fremont, Calif.), React Catheters (Medtronic, Minneapolis, Minn.), Mivi Q Distal Access Catheter (Mivi Neuroscience, Eden Prairie, Minn.), Zoom Aspiration Catheters (Imperative Care, Campbell, Calif.), and the Jet, Ace and MAX Reperfusion Catheters (Penumbra, Inc., Alameda, Calif.) for clot removal in patients with acute ischemic stroke or other reperfusion catheters known in the art. Although the catheter advancement element 300 is described herein in reference to catheter 200 it can be used to advance other catheters and it is not intended to be limiting to its use only with the catheters described herein.

The distal access system 100 is capable of providing quick and simple access to distal target anatomy, particularly the tortuous anatomy of the cerebral vasculature. The flexibility and deliverability of the distal access catheter 200 allow the catheter 200 to take the shape of the tortuous anatomy and avoids exerting straightening forces creating new anatomy. The distal access catheter 200 is capable of this even in the presence of the catheter advancement element 300 extending through its lumen. Thus, the flexibility and deliverability of the catheter advancement element 300 is on par or better than the flexibility and deliverability of the distal luminal portion 222 of the distal access catheter 200 in that both are configured to reach the middle cerebral artery (MCA) circulation without straightening out the curves of the anatomy along the way.

The catheter advancement element 300 may be used instead of a guidewire to provide catheter access to cerebrovascular targets. In this implementation, the catheter advancement element 300 may be advanced independently without being disposed within the lumen of a catheter to provide guidewire access. In another implementation, the catheter advancement element 300 may be inserted into a lumen of a catheter and "locked" in a position relative to the catheter with an RHV. In the locked embodiment, the catheter advancement element 300 and the catheter are advanced together as a unit to the desired location. Should the operator encounter tortuous anatomy while in the locked configuration, the RHV can be opened allowing the catheter advancement element 300 to be advanced independently of the catheter. After advancing the catheter advancement element 300 to a desired position, the catheter can then be advanced over the catheter advancement element 300, using the catheter advancement element 300 as a guide.

The catheter advancement element 300 can include a non-expandable, flexible elongate body 360 coupled to a proximal portion 366. The catheter advancement element 300 and the catheter 200 described herein may be configured for rapid exchange or over-the-wire methods. For example, the flexible elongate body 360 can be a tubular portion extending the entire length of the catheter advancement element 300 and can have a proximal opening from the lumen of the flexible elongate body 360 that is configured to extend outside the patient's body during use. Alternatively, the tubular portion can have a proximal opening positioned such that the proximal opening remains inside the patient's body during use. The proximal portion 366 can be a proximal element coupled to a distal tubular portion and extending proximally therefrom. A proximal opening from the tubular portion can be positioned near where the proximal element couples to the tubular portion. Alternatively, the proximal portion 366 can be a proximal extension of the tubular portion having a length that extends to a proximal opening near a proximal terminus of the catheter advancement element 300 (i.e. outside a patient's body).

The configuration of the proximal portion 366 can vary. In some implementations, the proximal portion 366 is simply a proximal extension of the flexible elongate body 360 that does not change significantly in structure but in flexibility. For example, the proximal portion 366 transitions from the very flexible distal regions of the catheter advancement element 300 towards less flexible proximal regions of the catheter advancement element 300. The proximal portion 366 provides a relatively stiff proximal end suitable for manipulating and torqueing the more distal regions of the catheter advancement element 300. In other implementations, the proximal portion 366 is a hypotube. The hypotube may be exposed or may be coated by a polymer. In still further implementations, the proximal portion 366 may be a polymer portion reinforced by a coiled ribbon. The proximal portion 366 can have the same outer diameter as the flexible elongate body or can have a smaller outer diameter as the flexible elongate body.

The proximal portion 366 need not include a lumen. For example, the proximal portion 366 can be a solid rod, ribbon, or wire have no lumen extending through it that couples to the tubular elongate body 360. Where the proximal portion 366 is described herein as having a lumen, it should be appreciated that the proximal portion 366 can also be solid and have no lumen. The proximal portion 366 is generally less flexible than the elongate body 360 and can transition to be even more stiff towards the proximal-most end of the proximal portion 366. Thus, the catheter advancement element 300 can have an extremely soft and flexible distal-most tip that transitions proximally to a stiff proximal portion 366 well suited for torqueing and pushing the distal elongate body 360. The transition in flexibility of the catheter advancement element 300 and the system as a whole is described in more detail below and in the Examples.

The elongate body 360 can be received within and extended through the internal lumen 223 of the distal luminal portion 222 of the catheter 200 (see FIG. 2B). The elongate body 360 or tubular portion can have an outer diameter. The outer diameter of the tubular portion can have at least one snug point, a difference between the inner diameter of the catheter 200 and the outer diameter of the tubular portion at the snug point can be no more than about 0.010", for example, from 0.003" up to about 0.010", preferably about 0.006" to about 0.008". As will be described in more detail below, the catheter advancement element 300 can also include a tip portion or distal tip 346 located distal to the at least one snug point of the tubular portion. The tip portion can have a length and taper along at least a portion of the length. The distal tip 346 of the catheter advancement element 300 can be extended beyond the distal end of the catheter 200 as shown in FIG. 2B. The proximal portion 366 of the catheter advancement element 300 or proximal extension is coupled to a proximal end region of the elongate body 360 and extends proximally therefrom. The proximal portion 366 can be less flexible than the elongate body 360 and configured for bi-directional movement of the elongate body 360 of the catheter advancement element 300 within the luminal portion 222 of the catheter 200, as well as for movement of the catheter system 100 as a whole. The elongate body 360 can be inserted in a coaxial fashion through the internal lumen 223 of the luminal portion 222. The outer diameter of at least a region of the elongate body 360 can be sized to substantially fill at least a portion of the internal lumen 223 of the luminal portion 222.

The overall length of the catheter advancement element 300 (e.g. between the proximal end through to the distal-most tip) can vary, but generally is long enough to extend through the support catheter 200 plus at least a distance beyond the distal end of the support catheter 200 while at least a length of the proximal portion 366 remains outside the proximal end of the guide sheath 400 and outside the body of the patient. In some implementations, the overall length of the catheter advancement element 300 is about 145 to about 150 cm and has a working length of about 140 cm to about 145 cm from a proximal tab or hub to the distal-most tip. The elongate body 360 can have a length that is at least as long as the luminal portion 222 of the catheter 200 although the elongate body 360 can be shorter than the luminal portion 222 so long as at least a minimum length remains inside the luminal portion 222 when a distal portion of the elongate body 360 is extended distal to the distal end of the luminal portion 222 to form a snug point or snug region with the catheter. In some implementations, this minimum length of the elongate body 360 that remains inside the luminal portion 222 when the distal tip 346 is positioned at its optimal advancement configuration is at least about 5 cm, at least about 6 cm, at least about 7 cm, at least about 8 cm, at least about 9 cm, at least about 10 cm, at least about 11 cm, or at least about 12 cm up to about 50 cm. In some implementations, the shaft length of the distal luminal portion 222 can be about 35 cm up to about 75 cm and shorter than a working length of the guide sheath and the insert length of the elongate body 360 can be at least about 45 cm, 46 cm, 47 cm, 48 cm, 48.5 cm, 49 cm, 49.5 cm up to about 85 cm.

The length of the elongate body 360 can allow for the distal end of the elongate body 360 to reach cerebrovascular targets within, for example, the M1 or M2 regions while the proximal end region of the elongate body 360 remains proximal to or below the level of severe turns along the path of insertion. For example, the entry location of the catheter system can be in the femoral artery and the target embolus can be distal to the right common carotid RCC artery, such as within the M1 segment of the middle cerebral artery on the right side. The proximal end region of the elongate body 360 where it transitions to the proximal portion 366 can remain within a vessel that is proximal to severely tortuous anatomy such as the carotid siphon, the right common carotid RCC artery, the brachiocephalic trunk BT, the take-off into the brachiocephalic artery from the aortic arch, the aortic arch AA as it transitions from the descending aorta DA. This avoids inserting the stiffer proximal portion 366, or the material transition between the stiffer proximal portion 366 and the elongate body 360, from taking the turn of the aortic arch or the turn of the brachiocephalic take-off from the aortic arch, which both can be very severe. The lengths described herein for the distal luminal portion 222 also can apply to the elongate body 360 of the catheter advancement element.

The proximal portion 366 can have a length that varies as well. In some implementations, the proximal portion 366 is about 90 cm up to about 95 cm. The distal portion extending distal to the distal end of the luminal portion 222 can include distal tip 346 that protrudes a length beyond the distal end of the luminal portion 222 during use of the catheter advancement element 300. The distal tip 346 of the elongate body 360 that is configured to protrude distally from the distal end of the luminal portion 222 during advancement of the catheter 200 through the tortuous anatomy of the cerebral vessels, as will be described in more detail below. The proximal portion 366 coupled to and extending proximally from the elongate body 360 can align generally side-by-side with the proximal control element 230 of the catheter 200. The arrangement between the elongate body 360 and the luminal portion 222 can be maintained during advancement of the catheter 200 through the tortuous anatomy to reach the target location for treatment in the distal vessels and aids in preventing the distal end of the catheter 200 from catching on tortuous branching vessels, as will be described in more detail below.

In some implementations, the elongate body 360 can have a region of relatively uniform outer diameter extending along at least a portion of its length and the distal tip 346 tapers down from the uniform outer diameter. The outer diameter of the elongate body 360 can include a step-down at a location along its length, for example, a step-down in outer diameter at a proximal end region where the elongate body 360 couples to the proximal portion 366. Depending upon the inner diameter of the catheter 200, the clearance between the catheter 200 and the outer diameter of the elongate body 360 along at least a portion of its length can be no more than about 0.010", such as within a range of about 0.003"-0.010" or between 0.006"-0.008".

The elongate body 360 can have an overall shape profile from proximal end to distal end that transitions from a first outer diameter having a first length to a tapering outer diameter having a second length. The first length of this first outer diameter region (i.e. the snug-fitting region between the distal luminal portion 222 and the elongate body 360) can be at least about 5 cm, or 10 cm, up to about 50 cm. The length of the tapering outer diameter can be between 1 cm and 4 cm. When the catheter advancement element 300 is inserted through the catheter 200, this tapered distal tip 346 is configured to extend beyond and protrude out through the distal end of the luminal portion 222 whereas the more proximal region of the body 360 (i.e. the first length described above) remains within the luminal portion 222.

As mentioned, the distal end of the luminal portion 222 can be blunt and have no change in the dimension of the outer diameter whereas the distal tip 346 can be tapered providing an overall elongated tapered geometry of the catheter system. The outer diameter of the elongate body 360 also approaches the inner diameter of the luminal portion 222 such that the step-up from the elongate body 360 to the outer diameter of the luminal portion 222 is minimized. Minimizing this step-up prevents issues with the lip formed by the distal end of the luminal portion 222 catching on the tortuous neurovasculature, such as around the carotid siphon near the ophthalmic artery branch, when the distal tip 346 in combination with the distal end region of the catheter 200 bends and curves along within the vascular anatomy. In some implementations, the inner diameter of the luminal portion 222 can be at least about 0.052", about 0.054" and the maximum outer diameter of the elongate body 360 can be about 0.048" such that the difference between them is about 0.006". In some implementations, the inner diameter of the luminal portion 222 can be about 0.070" and the maximum outer diameter of the elongate body 360 can be about 0.062" such that the difference between them is about 0.008". In some implementations, the inner diameter of the luminal portion 222 can be about 0.088" and the maximum outer diameter of the elongate body 360 can be about 0.080" such that the difference between them is about 0.008". In some implementations, the inner diameter of the luminal portion 222 can be about 0.072" and the maximum outer diameter of the elongate body 360 is about 0.070" such that the difference between them is only 2 thousandths of an inch (0.002"). In other implementations, the maximum outer diameter of the elongate body 360 is about 0.062" such that the difference between them is about 0.010". Despite the outer diameter of the elongate body 360 extending through the lumen of the luminal portion 222, the luminal portion 222 and the elongate body 360 extending through it in co-axial fashion are flexible enough to navigate the tortuous anatomy leading to the level of M1 or M2 arteries without kinking and without damaging the vessel.

The dimensions provided herein are approximate and each dimension may have an engineering tolerance or a permissible limit of variation. Use of the term "about" or "approximately" are intended to provide such permissible tolerance to the dimension being referred to. Where "about" or "approximately" is not used with a particular dimension herein that dimension need not be exact.

The length of the distal tip 346 (e.g. the region of the catheter advancement element 300 configured to extend distal to the distal end of the catheter 200 during use to obtain the optimum advancement configuration) can vary. In some implementations, the length of the distal tip 346 can be in a range of between about 0.50 cm to about 4.0 cm from the distal-most terminus of the elongate body 360 or between about 1.0 cm to about 3.0 cm. In other implementations, the length of the distal tip 346 is between 2.0 cm to about 2.5 cm. In some implementations, the length of the distal tip 346 varies depending on the inner diameter of the catheter 200 with which the catheter advancement element 300 is to be used. For example, the length of the distal tip 346 can be as shorter (e.g. 1.2 cm) for a catheter advancement element 300 sized to be used with a catheter 200 having an inner diameter of about 0.054" and can be longer (e.g. 2.5 cm) for a catheter advancement element 300 sized to be used with a catheter 200 having an inner diameter of about 0.088". The distal tip 346 can be a constant taper from the outer diameter of the elongate body 360 (e.g. the distal end of the marker 344b) down to a second smaller outer diameter at the distal-most terminus (e.g. the proximal end of the marker 344a) as shown in FIG. 7C. In some implementations, the constant taper of the distal tip 346 can be from about 0.048" outer diameter down to about 0.031" outer diameter over a length of about 1 cm. In some implementations, the constant taper of the distal tip 346 can be from 0.062" outer diameter to about 0.031" outer diameter over a length of about 2 cm. In still further implementations, the constant taper of the distal tip 346 can be from 0.080" outer diameter to about 0.031" outer diameter over a length of about 2.5 cm. The length of the constant taper of the distal tip 346 can vary, for example, between 0.8 cm to about 2.5 cm, or between 1 cm and 3 cm, or between 2.0 cm and 2.5 cm. The angle of the taper can vary depending on the outer diameter of the elongate body 360. For example, the angle of the taper can be between 0.9 to 1.6 degrees relative to horizontal. The angle of the taper can be between 2-3 degrees from a center line of the elongate body 360.

The catheter advancement element 300 can include a distal tip 346 that tapers over a length. The elongate body 360 of the catheter advancement element 300 can have an inner diameter that does not change over its length even in the presence of the tapering of the distal tip 346. Thus, the inner diameter of the lumen extending through the tubular portion of the catheter advancement element 300 can remain uniform and the wall thickness of the distal tip 346 can decrease to provide the taper. The wall thickness can thin distally along the length of the taper. Thus, the material properties in combination with wall thickness, angle, length of the taper can all contribute to the overall maximum flexibility of the distal-most end of the distal tip 346. The catheter advancement element 300 undergoes a transition in flexibility from the distal-most end towards the snug point where it achieves an outer diameter that is no more than about 0.010" different from the inner diameter of the catheter 200.

The distal tip 346 need not taper and can achieve its soft, atraumatic and flexible characteristic due to a material property other than due to a change in outer dimension to facilitate endovascular navigation to an embolus in tortuous anatomy. Additionally, or alternatively, the distal tip 346 of the elongate body 360 can have a transition in flexibility along its length. The most flexible region of the distal tip 346 can be its distal terminus. Moving along the length of the distal tip 346 from the distal terminus towards a region proximal to the distal terminus. For example, the distal tip 346 can be formed of a material having a material hardness of no more than 35D or about 62A and transitions proximally to be less flexible near where it is formed of a material having a material hardness of no more than 55D and 72D up to the proximal portion 366, which can be a stainless steel hypotube, or a combination of a material property and tapered shape. The materials used to form the regions of the elongate body 360 can include PEBAX (such as PEBAX 25D, 35D, 55D, 72D) or a blend of PEBAX (such as a mix of 25D and 35D, 25D and 55D, 25D and 72D, 35D and 55D, 35D and 72D, 55D and 72D, where the blend ratios may range from 0.1% up to 50% for each PEBAX durometer), with a lubricious additive compound, such as Mobilize (Compounding Solutions, Lewiston, Me.). In some implementations, the material used to form a region of the elongate body 360 can be Tecothane 62A. Incorporation of a lubricious additive directly into the polymer elongate body means incorporation of a separate lubricious liner, such as a Teflon liner, is unnecessary. This allows for a more flexible element that can navigate the distal cerebral anatomy and is less likely to kink. Similar materials can be used for forming the distal luminal portion 222 of the catheter 200 providing similar advantages. The flexibility of the distal tip 346 can be achieved by a combination of flexible lubricious materials and tapered shapes. For example, the length of the tip 346 can be kept shorter than 2 cm-3 cm, but maintain optimum deliverability due to a change in flexible material from distal-most tip towards a more proximal region a distance away from the distal-most tip. In an implementation, the elongate body 360 is formed of PEBAX (polyether block amide) embedded silicone designed to maintain the highest degree of flexibility. The wall thickness of the distal end of the luminal portion 222 can also be made thin enough such that the lip formed by the distal end of the luminal portion 222 relative to the elongate body 360 is minimized.

The elongate body 360 has a benefit over a microcatheter in that it can have a relatively large outer diameter that is just 0.003"-0.010" smaller than the inner diameter of the distal luminal portion 222 of the catheter 200 and still maintaining a high degree of flexibility for navigating tortuous anatomy. When the gap between the two components is too tight (e.g. less than about 0.003"), the force needed to slide the catheter advancement element 300 relative to the catheter 200 can result in damage to one or both of the components and increases risk to the patient during the procedure. The gap results in too tight of a fit to provide optimum relative sliding. When the gap between the two components is too loose (e.g. greater than about 0.010"), the distal end of the catheter 200 forms a lip that is prone to catch on branching vessels during advancement through tortuous neurovasculature, such as around the carotid siphon where the ophthalmic artery branches off.

The gap in ID/OD between the elongate body 360 and the distal luminal portion 222 can be in this size range (e.g. 0.003"-0.010") along a majority of their lengths. For example, the elongate body 360 can have a relatively uniform outer diameter that is between about 0.048" to about 0.080" from a proximal end region to a distal end region up to a point where the taper of the distal tip 346 begins. Similarly, the distal luminal portion 222 of the catheter 200 can have a relatively uniform inner diameter that is between about 0.054" to about 0.088" from a proximal end region to a distal end region. As such, the difference between their respective inner and outer diameters along a majority of their lengths can be within this gap size range of 0.003" to 0.010". The distal tip 346 of the elongate body 360 that is tapered will have a larger gap size relative to the inner diameter of the distal luminal portion 222. During use, however, this tapered distal tip 346 is configured to extend distal to the distal end of the catheter 200 such that the region of the elongate body 360 having an outer diameter sized to match the inner diameter of the distal luminal portion 222 is positioned within the lumen of the catheter 200 such that it can minimize the lip at the distal end of the catheter 200.

The elongate body 360 can be formed of various materials that provide a suitable flexibility and lubricity. Example materials include high density polyethylene, 72D PEBAX, 90D PEBAX, or equivalent stiffness and lubricity material. At least a portion of the elongate body 360 can be reinforced to improve navigation and torqueing (e.g. braided reinforcement layer). The flexibility of the elongate body 360 can increase towards the distal tip 346 such that the distal region of the elongate body 360 is softer, more flexible, and articulates and bends more easily than a more proximal region. For example, a more proximal region of the elongate body can have a bending stiffness that is flexible enough to navigate tortuous anatomy such as the carotid siphon without kinking. If the elongate body 360 has a braid reinforcement layer along at least a portion of its length, the braid reinforcement layer can terminate a distance proximal to the distal tip 346. For example, the distance from the end of the braid to the distal tip can be about 10 cm to about 15 cm or from about 4 cm to about 10 cm or from about 4 cm up to about 15 cm.

Figure 7A:
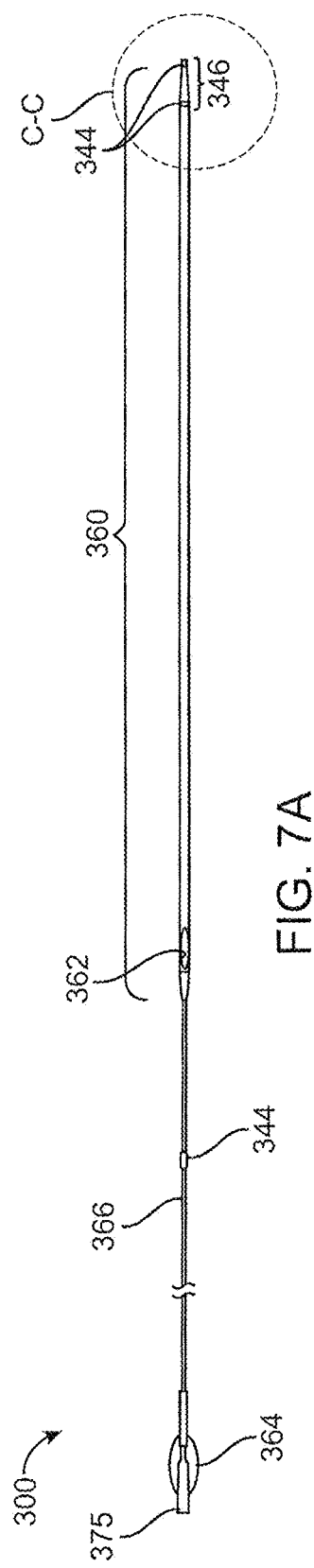
FIG. 7A is a side view of an implementation of a catheter advancement element.
Figure 7B:
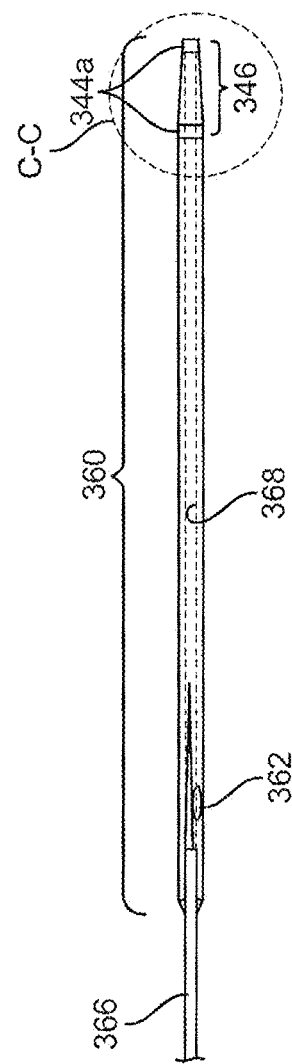
FIG. 7B is a cross-sectional view of the catheter advancement element of FIG. 7A.
Figure 7C:
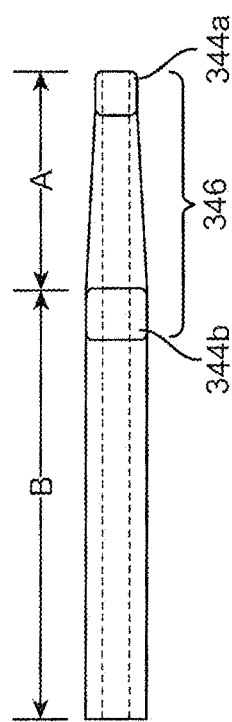
FIG. 7C is a detail view of FIG. 7B taken along circle C-C.
Figure 10A:
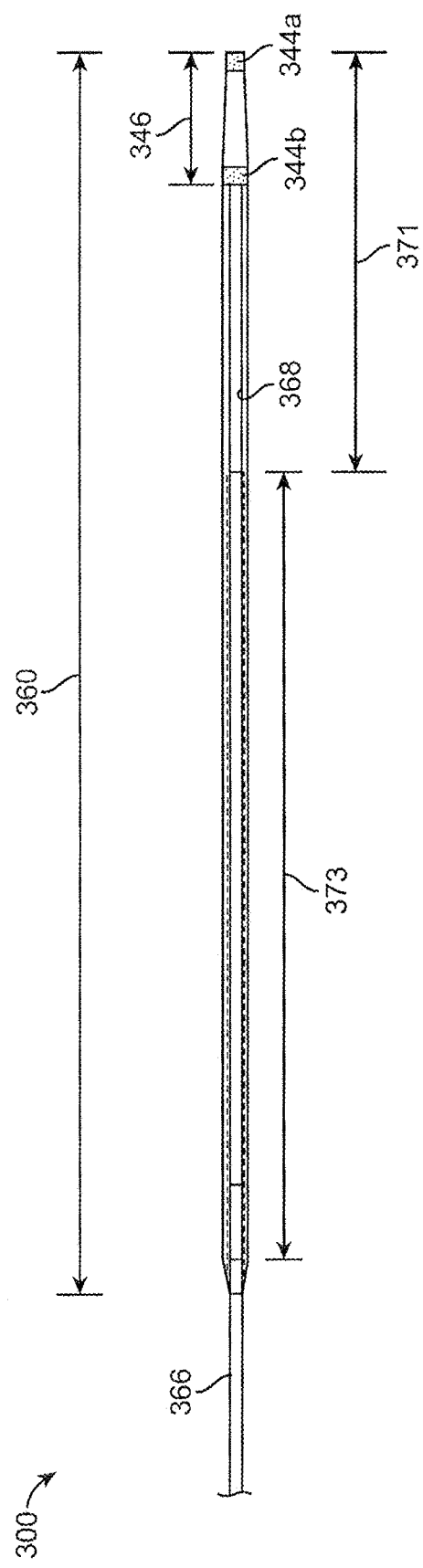
FIG. 10A is a schematic cross-sectional view of an implementation of a catheter advancement element.
Figure 10B:
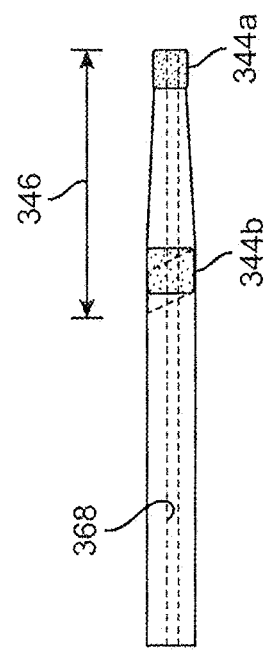
FIG. 10B is a schematic cross-sectional view of a distal end region of the catheter advancement element of FIG. 10A.
Figure 10C:
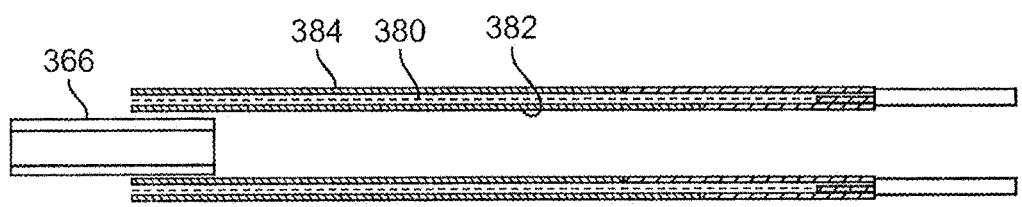
FIG. 10C is a schematic cross-sectional view of a middle region of the catheter advancement element of FIG. 10A.

In some implementations, the elongate body 360 can be generally tubular along at least a portion of its length such that it has a single lumen 368 extending parallel to a longitudinal axis of the catheter advancement element 300 (see FIG. 7A-7C and also FIG. 10A-10C). In an implementation, the single lumen 368 of the elongate body 360 is sized to accommodate a guidewire, however use of the catheter advancement element 300 generally eliminates the need for a guidewire lead. Methods of using the catheter advancement element 300 without a guidewire to deliver a catheter to distal regions of the brain are described in more detail below.

A guidewire can extend through the single lumen 368 generally concentrically from a proximal opening to a distal opening through which the guidewire can extend. In some implementations, the proximal opening is at the proximal end of the catheter advancement element 300 such that the catheter advancement element 300 is configured for over-the-wire (OTW) methodologies. In other implementations, the proximal opening is a rapid exchange opening 362 through a wall of the catheter advancement element 300 such that the catheter advancement element 300 is configured for rapid exchange rather than or in addition to OTW. In this implementation, the proximal opening 362 extends through the sidewall of the elongate body and is located a distance away from a proximal tab 364 and distal to the proximal portion 366 (see FIGS. 7A-7B and 7D). The proximal opening 362 can be located a distance of about 10 cm from the distal tip 346 up to about 20 cm from the distal tip 346. In some implementations, the proximal opening 362 can be located near a region where the elongate body 360 is joined to the proximal portion 366, for example, just distal to an end of the hypotube (see FIG. 7B). In other implementations, the proximal opening 362 is located more distally such as about 10 cm to about 18 cm from the distal-most end of the elongate body 360 (see FIG. 7D). A proximal opening 362 that is located closer to the distal tip 346 allows for easier removal of the catheter advancement element 300 from the catheter 200 leaving the guidewire in place for a "rapid exchange" type of procedure. Rapid exchanges can rely on only a single person to perform the exchange. The catheter advancement element 300 can be readily substituted for another device using the same guidewire that remains in position. The single lumen 368 of the elongate body 360 can be configured to receive a guidewire in the range of 0.014" and 0.018" diameter, or in the range of between 0.014" and 0.022". In this implementation, the inner luminal diameter of the elongate body 360 can be between 0.020" and 0.024". The guidewire, the catheter advancement element 300, and the catheter 200 can all be assembled co-axially for insertion through the working lumen of the guide sheath 400. The inner diameter of the lumen 368 of the elongate body 360 can be 0.019" to about 0.021".

Figure 7D:
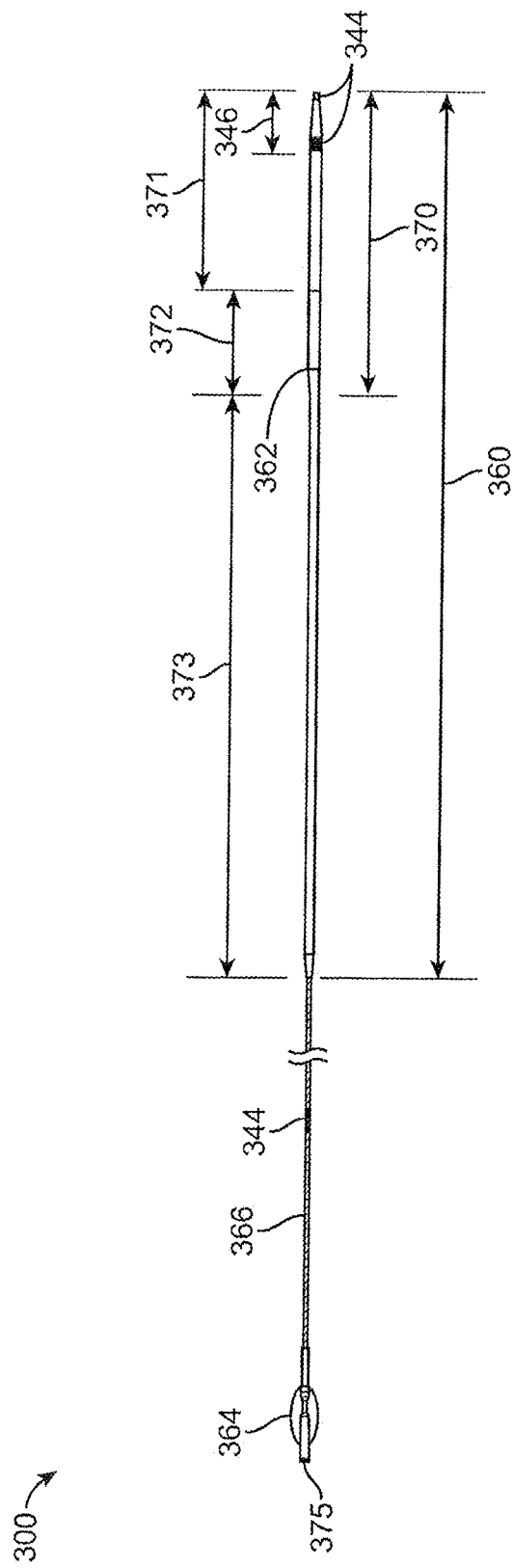
FIG. 7D is a side view of another implementation of a catheter advancement element.

FIG. 7D shows another implementation of the catheter advancement element 300 configured for rapid exchange. Rapid exchange configurations can dramatically shorten device length, decreases staffing requirements, and reduces fluoroscopy. As with other implementations described herein, the catheter advancement element 300 can include a non-expandable, flexible elongate body 360 coupled to a proximal portion 366 coupled to a proximal tab 364 or hub 375. The region near the distal tip 346 can be tapered such that the outer diameter tapers over a length of about 1 cm to about 4 cm. In some implementations, the distal taper length is 2.5 cm. In some implementations, the distal tip 346 tapers from about 0.080" to about 0.031". Also, the distal tip 346 can be formed of a material having a material hardness (e.g. 62A and 35D) that transitions proximally towards increasingly harder materials having (e.g. 55D and 72D) up to the proximal portion 366. For example, FIG. 7D illustrates segment 371 of the elongate body 360 including the distal tip 346 formed of a material having a material hardness of 35D and a length of about 10 cm to about 12.5 cm. Segment 371 of the elongate body 360 including the distal tip 346 formed of a material having a material hardness of 62A and a length of about 10 cm to about 12.5 cm. Segment 372 of the elongate body 360 formed of a material having a material hardness of 55D and have a length of about 5 cm to about 8 cm. Segment 373 of the elongate body 360 formed of a material having a material hardness of 72D can be about 25 cm to about 35 cm in length. The three segments 371, 372, 373 combined can form an insert length of the elongate body 360 from where the proximal portion 366 couples to the elongate body 360 to the terminus of the distal tip 346 that can be about 49 cm in length.

FIGS. 10A-10C illustrate an implementation of a catheter advancement element 300 incorporating a reinforcement layer 380. The reinforcement layer 380 can be a braid or other type of reinforcement to improve the torqueability of the catheter advancement element 300 and help to bridge the components of the catheter advancement element 300 having such differences in flexibility. The reinforcement layer 380 can bridge the transition from the rigid, proximal portion 366 to the flexible elongate body 360. In some implementations, the reinforcement layer 380 can be a braid positioned between inner and outer layers of Pebax 382, 384 (see FIG. 10C). The reinforcement layer 380 can terminate a distance proximal to the distal tip portion 346. For example, FIG. 10A illustrates the elongate body 360 having segment 371 and segment 373 located proximal to segment 371. Segment 371 can include the distal tip 346 formed of a material having a material hardness of at most about 35D. Segment 371 is unreinforced polymer having a length of about 4 cm up to about 12.5 cm. Segment 373 of the elongate body 360 located proximal to segment 371 can include the reinforcement layer 380 and can extend a total of about 37 cm up to the unreinforced distal segment 371. A proximal end region of the reinforcement layer 380 can overlap with a distal end region of the proximal portion 366 such that a small overlap of hypotube and reinforcement exists near the transition between the proximal portion 366 and the elongate body 360.

Again, with respect to FIG. 7D, an entry port 362 for a procedural guidewire can be positioned a distance away from the distal-most end of the elongate body 360. In some implementations, the entry/exit port 362 can be about 18 cm from the distal-most end creating a rapid exchange wire entry/exit segment 370. The outer diameter of the elongate body 360 within segment 370 (segments 371 and 372) can be about 0.080"-0.082" whereas segment 373 proximal to this rapid exchange wire entry/exit segment 370 can have a step-down in outer diameter such as about 0.062"-0.064".

The tubular portion of the catheter advancement element can have an outer diameter that has at least one snug point. A difference between the outer diameter at the snug point and the inner diameter of the lumen at the distal end of the distal, catheter portion can be no more than about 0.010". The at least one snug point of this tubular portion can be a point along the length of the tubular portion. The at least one snug point of this tubular portion can have a length that is at least about 5 cm up to about 50 cm, including for example, at least about 6 cm, at least about 7 cm, at least about 8 cm, at least about 9 cm, at least about 10 cm, at least about 11 cm, or at least about 12 cm up to about 50 cm. This length need not be uniform such that the length need not be snug alone its entire length. For example, the snug point region can include ridges, grooves, slits, or other surface features.

Figure 7E:
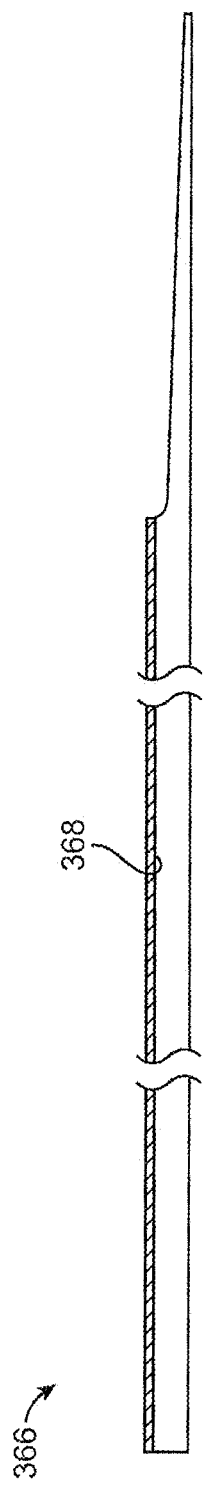
FIG. 7E is cross-sectional view of an implementation of a proximal portion the catheter advancement element of FIG. 7D.

In other implementations, the entire catheter advancement element 300 can be a tubular element configured to receive a guidewire through both the proximal portion 366 as well as the elongate body 360. For example, the proximal portion 366 can be a hypotube or tubular element having a lumen that communicates with the lumen 368 extending through the elongate body 360 (shown in FIG. 3). In some implementations, the proximal portion 366 can be a skived hypotube of stainless steel coated with PTFE having an outer diameter of 0.026". In other implementations, the outer diameter can be between 0.024" and 0.030". In some implementations, such as an over-the-wire version, the proximal portion 366 can be a skived hypotube coupled to a proximal hub 375. The proximal portion 366 can extend eccentric or concentric to the distal luminal portion 222. As best shown in FIG. 7E, the proximal portion 366 can be a stainless steel hypotube. The proximal portion 366 can be a solid metal wire that is round or oval cross-sectional shape. The proximal portion 366 can be a flattened ribbon of wire having a rectangular cross-sectional shape. The ribbon of wire can be curved into a circular, oval, c-shape, or quarter circle, or other cross-sectional shape along an arc. The proximal portion 366 can have any of variety of cross-sectional shapes whether or not a lumen extends therethrough, including a circular, oval, C-shaped, D-shape, or other shape. In some implementations, the proximal portion 366 is a hypotube having a D-shape such that an inner-facing side is flat and an outer-facing side is rounded. The rounded side of the proximal portion 366 can be shaped to engage with a correspondingly rounded inner surface of the sheath 400. The hypotube can have a lubricious coating such as PTFE. The hypotube can have an inner diameter of about 0.021", an outer diameter of about 0.0275", and an overall length of about 94 cm providing a working length for the catheter advancement element 300 that is about 143 cm. Including the proximal hub 375, the catheter advancement element 300 can have an overall length of about 149 cm. In some implementations, the hypotube can be a tapered part with a length of about 100 mm, starting proximal with a thickness of 0.3 mm and ending with a thickness of 0.10 mm to 0.15 mm. In still further implementations, the elongate body 360 can be a solid element coupled to the proximal portion 366 having no guidewire lumen.

The proximal portion 366 is shown in FIGS. 2A, 7A-7D, and 10A as having a smaller outer diameter compared to the outer diameter of the elongate body 360. The proximal portion 366 need not step down in outer diameter and can also have the same outer diameter as the outer diameter as the elongate body 360. For example, the proximal portion 366 can incorporate a hypotube or other stiffening element that is coated by one or more layers of polymer resulting in a proximal portion 366 having substantially the same outer diameter as the elongate body 360.

The proximal end of the proximal portion 366 can be coupled to a proximal hub 375. The proximal hub 375 can be an over-molded component having a luer thread and a luer taper formed on an inside of the proximal hub 375. The proximal hub 375 can incorporate a tab 364 providing for easier gripping by a user. The proximal hub 375 prevents advancement of the catheter advancement element 300 and the catheter 200 beyond the distal tip of the base sheath 400 or guide catheter by limiting insertion into the proximal RHV 434 providing critical functional and safety features for proper operation of the system 10.

At least a portion of the solid elongate body 360, such as the elongate distal tip 346, can be formed of or embedded with or attached to a malleable material that skives down to a smaller dimension at a distal end. The distal tip 346 can be shaped to a desired angle or shape similar to how a guidewire may be used. The malleable length of the elongate body 360 can be at least about 1 cm, 3 cm, 5 cm, and up to about 10 cm, 15 cm, or longer. In some implementations, the malleable length can be about 1%, 2%, 5%, 10%, 20%, 25%, 50% or more of the total length of the elongate body 360. In some implementations, the catheter advancement element 300 can have a working length of about 140 cm to about 143 cm and the elongate body 360 can have an insert length of about 49 cm. The insert length can be the PEBAX portion of the elongate body 360 that is about 49.5 cm. As such, the malleable length of the elongate body 360 can be between about 0.5 cm to about 25 cm or more. The shape change can be a function of a user manually shaping the malleable length prior to insertion or the tip can be pre-shaped at the time of manufacturing into a particular angle or curve. Alternatively, the shape change can be a reversible and actuatable shape change such that the tip forms the shape upon activation by a user such that the tip can be used in a straight format until a shape change is desired by the user. The catheter advancement element 300 can also include a forming mandrel extending through the lumen of the elongate body 360 such that a physician at the time of use can mold the distal tip 346 into a desired shape. As such, the moldable distal tip 346 can be incorporated onto an elongate body 360 that has a guidewire lumen.

The elongate body 360 can extend along the entire length of the catheter 200, including the distal luminal portion 222 and the proximal control element 230 or the elongate body 360 can incorporate the proximal portion 366 that aligns generally side-by-side with the proximal control element 230 of the catheter 200. The proximal portion 366 of the elongate body 360 can be positioned co-axial with or eccentric to the elongate body 360. The proximal portion 366 of the elongate body 360 can have a lumen extending through it. Alternatively, the portion 366 can be a solid rod or ribbon having no lumen.

Again, with respect to FIGS. 7A-7D, like the distal luminal portion 222 of the catheter 200, the elongate body 360 can have one or more radiopaque markers 344 along its length. The one or more markers 344 can vary in size, shape, and location. One or more markers 344 can be incorporated along one or more parts of the catheter advancement element 300, such as a tip-to-tip marker, a tip-to-taper marker, an RHV proximity marker, a Fluoro-saver marker, or other markers providing various information regarding the relative position of the catheter advancement element 300 and its components. In some implementations and as best shown in FIG. 7C, a distal end region can have a first radiopaque marker 344a and a second radiopaque marker 344b can be located to indicate the border between the tapering of the distal tip 346 and the more proximal region of the elongate body 360 having a uniform or maximum outer diameter. This provides a user with information regarding an optimal extension of the distal tip 346 relative to the distal end of the luminal portion 222 to minimize the lip at this distal end of the luminal portion 222 for advancement through tortuous anatomy. In other implementations, for example where the distal tip 346 is not necessarily tapered, but instead has a change in overall flexibility along its length, the second radiopaque marker 344b can be located to indicate the region where the relative flexibilities of the elongate body 360 (or the distal tip 346 of the elongate body 360) and the distal end of the luminal portion 222 are substantially the same. The marker material may be a platinum/iridium band, a tungsten, platinum, or tantalum-impregnated polymer, or other radiopaque marker that does not impact the flexibility of the distal tip 346 and elongate body 360. In some implementations, the radiopaque markers are extruded PEBAX loaded with tungsten for radiopacity. In some implementations, the proximal marker band can be about 2.0 mm wide and the distal marker band can be about 2.5 mm wide to provide discernable information about the distal tip 346.

The proximal control element 230 of the catheter 200 can include a proximal tab 234 on the proximal end of the proximal control element 230. Similarly, the proximal portion 366 coupled to the elongate body 360 can include a tab 364. The tabs 234, 364 can be configured to removably and adjustable connect to one another and/or connect to their corresponding proximal portions. The coupling allows the catheter advancement element 300 to reversibly couple with the catheter 200 to lock (and unlock) the relative extension of the distal luminal portion 222 and the elongate body 360. This allows the catheter 200 and the catheter advancement element 300 to be advanced as a single unit. In the locked configuration, the tab 364 or proximal portion 366 can be engaged with the catheter tab 234. In the unlocked configuration, the tab 364 may be disengaged from the catheter tab 234. The tab 364 or proximal portion 366 may attach, e.g., click or lock into, the catheter tab 234 in a fashion as to maintain the relationships of corresponding section of the elongate body 360 and the catheter 200 in the locked configuration. The tab 364 can be a feature on the proximal hub 375 such as the hub 375.

Such locking may be achieved by, e.g., using a detent on the tab 364 that snaps into place within a recess formed in the catheter tab 234, or vice versa. For example, the tab 234 of the catheter 200 can form a ring having a central opening extending therethrough. The tab 364 of the body 360 can have an annular detent with a central post sized to insert through the central opening of the tab 234 such that such that the ring of the tab 234 is received within the annular detent of tab 364 forming a singular grasping element for a user to advance and/or withdraw the catheter system through the access sheath. The tabs 234, 364 may be affixed or may be slideable to accommodate different relative positions between the elongate body 360 and the luminal portion 222 of the catheter 200. In some implementations, a proximal end of the proximal control element 230 of the catheter 200 can include a coupling feature 334, such as clip, clamp, c-shaped element or other connector configured to receive the proximal portion 366 of the catheter advancement element 300 (see FIG. 2A). The coupling feature 334 can be configured to snap together with the proximal portion 366 through an interference fit such that a first level of force is needed in order to insert the proximal portion 366 into the clip of the tab 234 and a second, greater level of force is needed to remove the proximal portion 366 from the clip of the tab 234. However, upon inserting the proximal portion 366 into the coupling feature 334 the catheter advancement element 300 and the catheter 200 can still be slideably adjusted relative to one another along a longitudinal axis of the system. The amount of force needed to slideably adjust the relative position of the two components can be such that inadvertent adjustment is avoided and the relative position can be maintained during use, but can be adjusted upon conscious modification. The configuration of the coupling between the proximal portion 366 of the catheter advancement element 300 and the proximal control element 230 of the catheter 200 can vary. Generally, however, the coupling is configured to be reversible and adjustable while still providing adequate holding power between the two elements in a manner that is relatively user-friendly (e.g. allows for one-handed use) and organizes the proximal ends of the components (e.g. prevents the proximal control element 230 and proximal portion 366 from becoming twisted and entangled with one another). The coupling feature 334 configured to prevent entanglement and aid in the organization of the proximal portions can be integrated with the tabs or can be a separate feature located along their proximal end region.

The catheter advancement element 300 can be placed in a locked configuration with the catheter 200 configured for improved tracking through a tortuous and often diseased vasculature in acute ischemic stroke. Other configurations are considered herein. For example, the elongate body 360 can include one or more detents on an outer surface. The detents can be located near a proximal end region and/or a distal end region of the elongate body 360. The detents are configured to lock with correspondingly-shaped surface features on the inner surface of the luminal portion 222 through which the elongate body 360 extends. The catheter advancement element 300 and the catheter 200 can have incorporate more than a single point of locking connection between them. For example, a coupling feature 334, such as clip, clamp, c-shaped element or other connector configured to hold together the catheter advancement element 300 and proximal control element 230 or tab 234 of the catheter 200.

In some implementations, the proximal control element 230 of the catheter 200 can run alongside or within a specialized channel of the proximal portion 366. The channel can be located along a length of the proximal portion 366 and have a cross-sectional shape that matches a cross-sectional shape of the catheter proximal control element 230 such that the proximal control element 230 of the catheter 200 can be received within the channel and slide smoothly along the channel bi-directionally. Once the catheter 200 and elongate body 360 are fixed, the combined system, i.e., the catheter 200-catheter advancement element 300 may be delivered to a target site, for example through the working lumen of the guide sheath 400 described elsewhere herein.

The catheter advancement element 300 (whether incorporating the reinforcement layer or not) loaded within the lumen of the catheter 200 may be used to advance the catheter 200 to distal regions of the brain (e.g. level of the MCA). The traditional approach to the Circle of Willis is to use a triaxial system including a guidewire placed within a conventional microcatheter placed within an intermediate catheter. The entire coaxial system can extend through a base catheter or sheath. The sheath is typically positioned such that the distal tip of the sheath is placed in a high cervical carotid artery. The coaxial systems are often advanced in unison up to about the terminal carotid artery where the conventional coaxial systems must then be advanced in a step-wise fashion in separate throws. This is due to the two sequential 180 degree or greater turns (see FIGS. 1A-1C). The first 180 degree turn is at the level of the petrous to the cavernous internal carotid artery. The second 180 degree turn is at the terminal cavernous carotid artery as it passes through the bony elements and reaches the bifurcation into the anterior cerebral artery ACA and middle cerebral artery MCA. This S-shape region is referred to herein as the "siphon" or "carotid siphon". The ophthalmic artery arises from the cerebral ICA, which represents a common point of catheter hang-up in accessing the anterior circulation.

Conventional microcatheter systems can be advanced through to the anterior circulation over a guidewire. The inner diameter of the conventional microcatheter is significantly larger than the outer diameter of the guidewire over which it is advanced thereby forming a lip on a distal end region of the system that can catch on these side branches during passage through the siphon. Conventional microcatheter systems (i.e. guidewire, microcatheter, and intermediate catheter) are advanced through the bends of the carotid siphon sequentially to distal target sites rather than in a single, smooth pass. The bends of the carotid siphon are taken one at a time in a step-wise advancement technique. For example, to pass through the carotid siphon, the conventional microcatheter is held fixed while the guidewire is advanced alone a first distance (i.e. through the first turn of the siphon). Then, the guidewire is held fixed while the conventional microcatheter is advanced alone through the first turn over the guidewire. Then, the conventional microcatheter and guidewire are held fixed while the intermediate catheter is advanced alone through the first turn over the microcatheter and guidewire. The process repeats in order to pass through the second turn of the siphon, which generally is considered the more challenging turn into the cerebral vessel. The microcatheter and intermediate catheter are held fixed while the guidewire is advanced alone a second distance (i.e. through the second turn of the siphon). Then, the guidewire and interventional catheter are held fixed while the microcatheter is advanced alone through that second turn over the guidewire. Then, the guidewire and the microcatheter are held fixed while the interventional catheter is advanced alone through the second turn. This multi-stage, step-wise procedure is a time-consuming process that requires multiple people performing multiple hand changes on the components. For example, two hands to fix and push the components over each other forcing the user to stage the steps. The step-wise procedure is required because the stepped transitions between these components (e.g. the guidewire, microcatheter, and intermediate catheter) makes advancement too challenging.

In contrast, the catheter 200 and catheter advancement element 300 eliminate this multi-stage, step-wise component advancement procedure to access distal sites across the siphon. The catheter 200 and catheter advancement element 300 can be advanced as a single unit through the both turns of the carotid siphon CS. Both turns can be traversed in a single smooth pass or throw to a target in a cerebral vessel without the step-wise adjustment of their relative extensions and without relying on the conventional step-wise advancement technique with conventional microcatheters. The catheter 200 having the catheter advancement element 300 extending through it allows a user to advance them in unison in the same relative position from the first bend of the siphon through the second bend beyond the terminal cavernous carotid artery into the ACA and MCA. Importantly, the advancement of the two components can be performed in a single smooth movement through both bends without any change of hand position.

The catheter advancement element 300 can be in a juxtapositioned relative to the catheter 200 that provides an optimum relative extension between the two components for single smooth advancement. The catheter advancement element 300 can be positioned through the lumen of the catheter 200 such that its distal tip 346 extends beyond a distal end of the catheter 200. The distal tip 346 of the catheter advancement element 300 eliminates the stepped transition between the inner member and the outer catheter 200 thereby avoiding issues with catching on branching vessels within the region of the vasculature such that the catheter 200 may easily traverse the multiple angulated turns of the carotid siphon CS. The optimum relative extension, for example, can be the distal tip 346 of the elongate body 360 extending distal to a distal end of the catheter 200. A length of the distal tip 346 extending distal to the distal end of the catheter 200 during advancement can be between 0.5 cm and about 4 cm. This juxtaposition can be a locked engagement with a mechanical element or simply by a user holding the two components together.

The components can be advanced together with a guidewire, over a guidewire pre-positioned, or without any guidewire at all. In some implementations, the guidewire can be pre-assembled with the catheter advancement element 300 and catheter 200 such that the guidewire extends through a lumen of the catheter advancement element 300, which is loaded through a lumen of the catheter 200, all prior to insertion into the patient. The pre-assembled components can be simultaneously inserted into the sheath 400 and advanced together up through and past the turns of the carotid siphon.

The tubular portion 360 of the catheter advancement element 300 can have a radiopaque marker band embedded within or positioned over a wall of the tubular portion 360 near the distal end region. A first radiopaque marker band 344a can be found at the distal end of the tapered tip portion 346 and a second radiopaque marker band 344b can be found at the proximal end of the tapered tip portion 346. The proximal radiopaque marker band 344b can have a proximal edge, a distal edge, and a width between the proximal and distal edges. When in the advancement configuration, the proximal edge of the radiopaque marker band 344b can align substantially with the distal end of the distal, catheter portion 222 such that the radiopaque marker band 344b remains external to the lumen 223 of the distal, catheter portion 222. At least a portion of the radiopaque marker band 344b can be positioned at the snug point, or the point of the catheter advancement element 300 where the outer diameter is no more than about 0.010", preferably between about 0.006" and 0.008" smaller than the inner diameter of the catheter 200 it is positioned within. The at least one snug point of the tubular portion 360 can be located proximal to the tip portion 346 and can be where the taper of the tip portion 346 substantially ends. This allows for full extension of the tapered tip portion 346 outside the distal end of the catheter 200 and the snug point aligned substantially within the distal opening from the lumen 223 of the distal, catheter portion 222 thereby minimizing any distal-facing lip that might be created by the catheter 200. The snug point can be located along at least a portion of a length of the outer diameter of the tubular portion 360 that has a length of at least about 5 cm up to about 10 cm, the outer diameter being substantially uniform or non-uniform.

Methods of Use

The systems described herein contemplate using a base sheath and a catheter that can pass through the sheath and having sufficient length to reach the intracerebral target, such as the M1 segment of the middle cerebral artery. The use of a delivery catheter or catheter advancement element with a tapered tip allow for large bore catheter delivery of full-length, "over-the-wire" catheters or catheters such as those described herein having a proximal extension. The catheter advancement element can include a pair of radiopaque markers configured to aid the operator in delivery of the system. The distal marker near the distal-most end of the catheter advancement element can be differentiated from the distal marker on the catheter by its characteristic appearance under fluoroscopy as well as by simply jogging back and forth the atraumatic catheter advancement element to understand the relationship and positioning of the catheter advancement element relative to the catheter. The second marker on the catheter advancement element that is proximal to the distal-most tip marker can delineate the taper of the distal tip, i.e. where the outer diameter of the catheter advancement element has a sufficient size to reduce the "lip" of the transition between the catheter advancement element and the catheter through which it is inserted and configured to deliver. The markers aid in positioning the catheter advancement element relative to the distal end of the large-bore catheter such that the tip of the catheter is aligned with the taper of the catheter advancement element and the best alignment is facilitated.

The relationship between the distal tip marker of the large-bore catheter is at or ideally just proximal to the taper marker of the catheter advancement element (i.e. the proximal marker identifying the start of the taper) is identifiable with the tandem marker system. The paired elements are in a "tip-to-taper" position. The relative extension between the catheter advancement element and the catheter can be adjusted at the insertion of the system into the RHV. However, the relative extension can become altered with advancement through the sheath or guide catheter. As the system exits the guide catheter, the large bore catheter and the catheter advancement element can be adjusted to that the tip-to-taper position is assumed as the system traverses the often tortuous proximal vessel (e.g. the cervical internal carotid artery) towards more distal targets. The system of the large bore catheter and the catheter advancement element can be locked into their relative extension so that the juxtaposition of the catheter advancement element and the large-bore catheter is maintained. As the large-bore catheter is visualized within the sheath distal end or even slightly beyond the distal end of the sheath, the catheter advancement element can be adjusted to assume the proper position relative to the catheter before advancement resumes. The optimum relative extension between the distal marker of the catheter to the taper marker on the catheter advancement element can be maintained through as much of the anatomy as possible to maximize the delivery capability of the catheter advancement element to navigate both tortuosity and to avoid side branches such as the ophthalmic artery. Once the target is reached, the catheter advancement element is then held fixed and the large-bore catheter then advanced over the catheter advancement element towards the target without crossing the target.

The catheter advancement element is designed specifically such that the catheter can be delivered without a need for a guidewire. This ability to deliver without crossing the embolus and without a guidewire is based upon the smooth transitions between the outer diameter of the catheter advancement element and the large-bore catheter as well as the smooth transition in flexibility between the two. When the catheter advancement element is bent into an arc of greater than 180 degrees, the softness and flexibility creates a smooth arc without severe bends or kinks in the geometry of the catheter. Thus, the catheter advancement element seeks the larger lumens and goes where the majority of blood flow goes as opposed to into the smaller branch arteries. The distal tip of the catheter advancement element can facilitates a strong preference to seek out the larger vessels during advancement into the distal vessels. This propensity to stay within the main channel allows for the advancement of large bore catheters without the aid of a guidewire. The propensity to follow the main channels of blood flow aligns with acute ischemic stroke pathophysiology where major emboli tend to follow these same routes to a point where the embolus lodges and interrupts antegrade blood flow. As well, these major channels are often ideal for placement of access catheters as these conduit arteries allow for smaller catheters to pass into specific target arteries for therapeutic intervention.

Standard neurovascular intervention, and nearly all endovascular intervention, is predicated on the concept that a guidewire leads a catheter to a target location. The guidewires are typically pre-shaped and often find side-branches of off-target locations where the guidewire will bunch or prolapse causing time-consuming nuisances during interventions that often require repeated redirection of the guidewire by the operator to overcome. In addition, this propensity of a guidewire to enter side-branches can be dangerous. Guidewires are typically 0.014" to 0.018" in the neuroanatomy and will find and often traumatize small branches that accommodate this size, which can lead to small bleeds or dissections and occlusion. In a sensitive area like the brain these events can be catastrophic. The tendency of a guidewire to bunch and prolapse can also cause a leading edge to the guidewire that can be advanced on its own or as part of a triaxial system to create dissection planes and traumatize small vessels.

In contrast, the catheter advancement element described herein preferentially stays in the larger lumen of a conduit vessel. In the setting of stroke treatment an embolus is driven to certain anatomies because of the blood flow that the arterial system draws in the cerebral anatomy. The catheter advancement element tends to traverse a path identical to the path an embolus will take, particularly an embolus driven from a location such as cardiac or carotid etiology. The catheter advancement element delivers to the largest lumen within the anatomy even in light of the highly tortuous anatomy and curves being navigated. The catheter advancement element can preferentially take the larger lumen at a bifurcation while also following the current of the greatest blood flow thereby maintaining the general direction and angulations of the parent vessel.

In viewing the standard anatomy found in the cerebral vasculature, the Circle of Willis is fed by two vertebral and two carotid conduit arteries. As these four arteries are the access points to the cerebral anatomy—the course of the catheter advancement element can be identified and has been validated in standard cerebral anatomy models. In the anterior circulation where the conduit artery point of entry for cerebral endovascular procedures is the internal carotid artery (ICA), the catheter advancement element can guide the large-bore catheter to the M1 segment of the middle cerebral artery (MCA). The very flexible nature of the catheter advancement element combined with the distal flexible nature of most cerebral catheters combine to allow delivery through severe tortuosity. Independent of the tortuous nature of the course of the arteries, the catheter advancement element tends to navigate the turns and deliver to the largest offspring from a parent artery, for example, ICA to M1 segment of the MCA. The M2 level branching of the M1 can be variable, but is often seen to have two major M2 branches (superior and inferior) and, depending on the anatomy, which can vary significantly between patients, may be seen to bifurcate "equally" or "unequally." If the caliber of the M2 branching is of similar size and angulation, the catheter advancement element may take one of the two branches. If the target for catheter placement is not in a favorable angulation or size of artery, the catheter advancement element may need to be curved (e.g. via shaping of a malleable distal tip) and directed or a guidewire may be used.

In some anatomies where the M2 bifurcation is "even" in size, a back-and-forth motion may aid in selecting one branch then the other while still avoid the need or use of a guidewire or a curved distal tip of the catheter advancement element. The back-and-forth motion can allow for the catheter advancement element to be directed into either branch of the M2. The catheter advancement element, even when initially straight, achieves some curvature that aids in directing it into a branch vessel. Thus, when an operator encounters an M2 bifurcation and there is a desire to cannulate either branch of an evenly divided bifurcation, selection of either branch is possible using the catheter advancement element without a guidewire.

Thus, main channels such as the ICA, the middle cerebral artery and its tributaries in the anterior circulation will naturally be the pathway of preference for the described catheter advancement element and subsequence large-bore catheter delivery (via access from the ICA). A similar phenomenon can occur in the posterior circulation, which is accessed via the vertebral arteries arising from the subclavian arteries on the right and the left. The catheter advancement element will take the main channels in this circulation as well by traversing the vertebral arteries to the basilar artery and to the major tributaries of the basilar: the posterior cerebral artery and superior cerebellar arteries in the posterior circulation.

Navigation using the catheter advancement element can provide maximal deliverability with minimal vascular trauma. Catheters can cause "razoring" effects in a curved vessel because the blunt end of a large bore catheter can tend to take the greater curve in rounding a vessel when pushed by the operator. This blunt end can gouge or "razor" the greater curve with its sharp edge increasing the risk for dissection along an anatomic plane within the multilayered mid- or large-sized artery or vein (see, e.g. Catheter Cardiovasc. Intern. 2014 February; 83(2):211-20). Placement of a partially-inflated balloon and guidewire through the catheter in this setting can mitigate this "razor" effect by taking the edge off the large-bore catheter. Similarly, the catheter advancement element can serve to minimize the edge of these catheters. Positioning the catheter advancement element within the lumen of the large-bore catheter such that the taper marker of the catheter advancement element is aligned optimally with the distal tip marker of the catheter minimizes the edge and thereby eliminates "razoring" as the large-bore catheter is advanced through turns of the vessel. This is particularly useful for the cerebral anatomy. Stroke treatments are typically needed in regions distal to the carotid siphon, particularly distal to the ophthalmic artery takeoff from the greater curve of the severe tortuosity of the final turn of the carotid siphon "5-turn", the "anterior genu" of the carotid siphon typically seen as part of the terminal internal carotid artery (ICA). The specifics of the catheter advancement element in proper alignment within the large bore catheter (the "tip-to-taper" position noted by the distal tip marker) relative to the taper marker of the catheter advancement element maximize the likelihood that razoring and hang-up on the ophthalmic artery are avoided. The taper marker of the catheter advancement element can be positioned at or past the take-off of the ophthalmic artery to minimize these deleterious effects and allows the large-bore catheter to pass the ophthalmic artery without incident. In a relatively straight segment, which is common after passing the siphon, the large-bore catheter can be advanced over the catheter advancement element, which serves still as a guiding element to the target. The transition between the catheter advancement element and the distal edge of the large-bore catheter is insignificant, especially compared to the step changes present with a typical microcatheter or guidewire, which do not prevent hand-ups on branches such as the ophthalmic artery. The catheter advancement element allows for maneuvering of the large-bore catheter clear to the face of the embolus without use of a microcatheter or guidewire and without crossing and/or fragmenting the embolus in any way.

Conventional techniques to treat AIS whether with a stent retriever, aspiration techniques, or a combination of the two, require crossing the target occlusion with a guidewire and a microcatheter. Crossing of the embolus with a guidewire and then microcatheter can create fragmentation of the occlusion, which can be friable and thrombotic in nature. Thus, an aspiration technique where the embolus is removed en toto without any crossing of the occlusion with any device is advantageous.

A stent retriever cannot cross or engage the target occlusion without the "unsleeving" of the stent retriever across the embolus. ADAPT is a frontline aspiration-only technique that avoids crossing the target occlusion with a stent retriever thereby lessening the risk of fragmentation. However, the ADAPT approach still requires crossing the target occlusion with both a guidewire and microcatheter (see Turk et al. *J. Neurointerv. Surg.* 2014 Apr. 1; 6(3):231-7). A guide catheter such as Neuron Max (Penumbra) is positioned as distally as possible. A microcatheter and a micro guidewire are advanced through the guide catheter and distal to the occlusion. Using the microcatheter and micro guidewire as support, a reperfusion catheter such as Penumbra 5 Max is advanced to the occlusion. Aspiration is applied until the occlusion corks or wedges within the tip of the reperfusion catheter. The reperfusion catheter is withdrawn and removed while maintaining aspiration and the occlusion within the catheter tip.

The systems described herein need not incorporate a guidewire or microcatheter. And, if a guidewire and microcatheter are used, they need not be advanced to cross the target occlusion. Thus, the systems described herein can incorporate relatively large bore catheters that are delivered without disturbing the target occlusion, reducing the risk for stroke and downstream effects from fragmentation of the occlusion, and having improved efficiency. Additionally, the systems described herein are single-operator systems allowing the operator to work at a single RHV and, in the case of spined components, can manipulate all the elements being used to navigate the anatomy with single-handed "pinches." This is sometimes referred to herein as "monopoint."

As described above, the catheter advancement element can be arranged coaxially within the single lumen of the distal catheter portion forming a coaxial catheter system. The catheter can have a distal, catheter portion and a proximal extension. The distal, catheter portion can have an inner diameter defining the single lumen and a distal end defining a distal opening from the lumen. The proximal extension can be coupled to and extend proximally from the distal, catheter portion. The catheter advancement element can have a tubular, polymeric portion having an inner diameter defining a lumen, a first outer diameter that is substantially uniform along a length, and a radiopaque marker band embedded within or positioned over a wall of the tubular, polymeric portion. The radiopaque marker band can create a second outer diameter that is located distal to and that is larger than the first outer diameter. A tapered, polymeric tip can be located distal to the second outer diameter that terminate at a distal opening from the lumen of the tubular portion. The tapered, polymeric tip can have a length that is between about 0.5 cm up to about 4 cm, for example, between about 1 cm and about 3 cm, or about 2.5 cm. The catheter advancement element can also include a proximal extension coupled to and extending proximally from the tubular, polymeric portion.

The coaxial catheter system can have an advancement configuration where the tapered, polymeric tip of the catheter advancement element extends distal to the distal end of the distal, catheter portion and the radiopaque marker band is substantially aligned with the distal end of the distal, catheter portion, and the first outer diameter is positioned within the lumen of the distal, catheter portion.

The operator can work from a single RHV of the guide sheath to manipulate both the catheter and the catheter advancement element. The coaxial catheter system can be advanced together, maintaining the advancement configuration. The relative relationship between the radiopaque marker band on the catheter advancement element and a second marker band near the distal end of the catheter can aid in maintaining the advancement configuration during delivery. The operator can hold the two in relative position to one another using a single pinch and advance this coaxial catheter system.

The coaxial catheter system can be advanced as far distal as possible until the catheter advancement element is positioned at the face of the embolus. The proximal extension of the catheter advancement element can be held "fixed" at the RHV and the catheter advanced over the catheter advancement element so that the distal end of the distal, catheter portion is advanced over the catheter advancement element to the face of the embolus. No guidewire or microcatheter is needed to advance the coaxial catheter system to the face of the embolus. Importantly, no devices need cross the embolus.

The catheter advancement element can then be withdrawn from the coaxial catheter system and removed from the single RHV while the catheter is held in position at the face of the embolus. The system is ready for initiation of aspiration as will be described in more detail below.

In some implementations, the first coaxial catheter system may not be able to reach the face of the embolus. Thus, the catheter advancement element of the coaxial catheter system can be removed leaving the lumen of the distal, catheter portion open for advancing a second coaxial catheter system through the first catheter. The second coaxial catheter system can include a second catheter and a second catheter advancement element and be advanced similarly as the first coaxial catheter system (i.e. via monopoint manipulations), but through the first catheter acting as a support catheter.

Once the catheter is in position at the face of the embolus, the RHV can be sealed and aspiration initiated through the same RHV such as via a side-arm. The embolus can be aspirated from the body through the catheter via the aspiration pressure alone. Alternatively, the catheter having the embolus corked at the distal opening of the catheter can be slowly withdrawn, for example towards a lumen of a larger bore catheter, as aspiration is applied to effect embolus removal.

Withdrawing an embolus corked at the distal opening of the catheter back to the distal opening of the guide sheath can increase the risk of fragmentation and embolization depending on the distance it must be withdrawn before being fully encapsulated within a lumen. Thus, it is desirable to use a nested system of successively larger catheter sizes to create a family of aspiration catheters all working from a single point of operation via the single RHV. This allows for the smallest bore catheter advanced most distal to withdraw only a short distance into a larger bore catheter, which in turn can suction the embolus en toto, or, if needed, be withdrawn another short distance into a larger bore catheter that can suction the embolus from the body. The likelihood of the captured clot from fragmenting is thereby reduced and the likelihood of the clot being aspirated en toto is increased.

The guide sheath can be a large 7F sheath configured to receive a larger bore catheter having an inner diameter of approximately 0.088", which in turn can receive an intermediate bore catheter having an inner diameter of approximately 0.070", which in turn can receive a smaller bore catheter having an inner diameter of approximately 0.054". Any of a variety of sizes is considered herein and that these examples are not intended to be limiting.

Although the larger bore catheter can more efficiently capture the embolus by aspiration, there is a possibility that the substantially larger dimension of the larger bore catheter can prevent it being advanced to reach the embolus without additional manipulations. In some implementations, a smaller bore catheter extending through the lumen of the larger bore catheter can be advanced to the face of the embolus. The smaller bore catheter (and its catheter advancement element) can be held fixed such that the larger bore catheter is advanced over the smaller bore catheter as distal as possible. If the larger bore catheter crawling over the smaller bore catheter is able to reach the embolus in this way, the catheter advancement element can be removed from the smaller bore catheter, the RHV closed to a seal, and aspiration initiated. Both the distal end of the smaller bore catheter and the distal end of the larger bore catheter are positioned at the face of the embolus. The smaller bore catheter can be removed from the system under continuous aspiration. If free flow is established with aspiration (e.g. as seen by the flow into the vacuum source), the operator can leave the larger bore catheter in place and consider whether to perform angiography to confirm establishment reconstitution of antegrade flow and resolution of the obstruction after insuring that the large-bore catheter is completely free of debris with aggressive aspiration and flushing. If free flow is not established, the aspiration can be continued and removal of the smaller bore catheter can be followed by removal of the larger bore catheter thereby removing the embolus from the body using the higher flow and forces generated by the larger bore catheter under full aspiration without the smaller bore catheter positioned within its lumen obstructing flow. A single, shared vacuum source may be used during removal of both the smaller bore and the larger bore catheters.

If the larger bore catheter is not able to reach the target embolus by crawling over the smaller bore catheter, the larger bore catheter and the catheter advancement element for the smaller bore catheter can be held fixed at the RHV such that the smaller bore catheter can be advanced between them to the face of the embolus. The smaller bore catheter can then provide a rail for another attempt at advancing the larger bore catheter towards the face of the embolus. These steps can be repeated in sequence to "inch" the larger bore catheter toward the embolus until both the distal end of the smaller bore catheter and the distal end of the larger bore catheter are positioned near the face of the embolus such that aspiration embolectomy can be performed through them.

The smaller bore catheter can be attached to the embolus and withdraw the embolus towards the larger bore catheter. Thus, where the embolus may be too large to fully enter the lumen of the smaller bore catheter it may be engulfed or retrieved by the lumen of the larger bore catheter. The smaller bore catheter having embolus attached to the distal end by aspiration can be withdrawn followed immediately by capture and withdrawal of the embolus via the larger bore catheter under aspiration.

Figure 12:
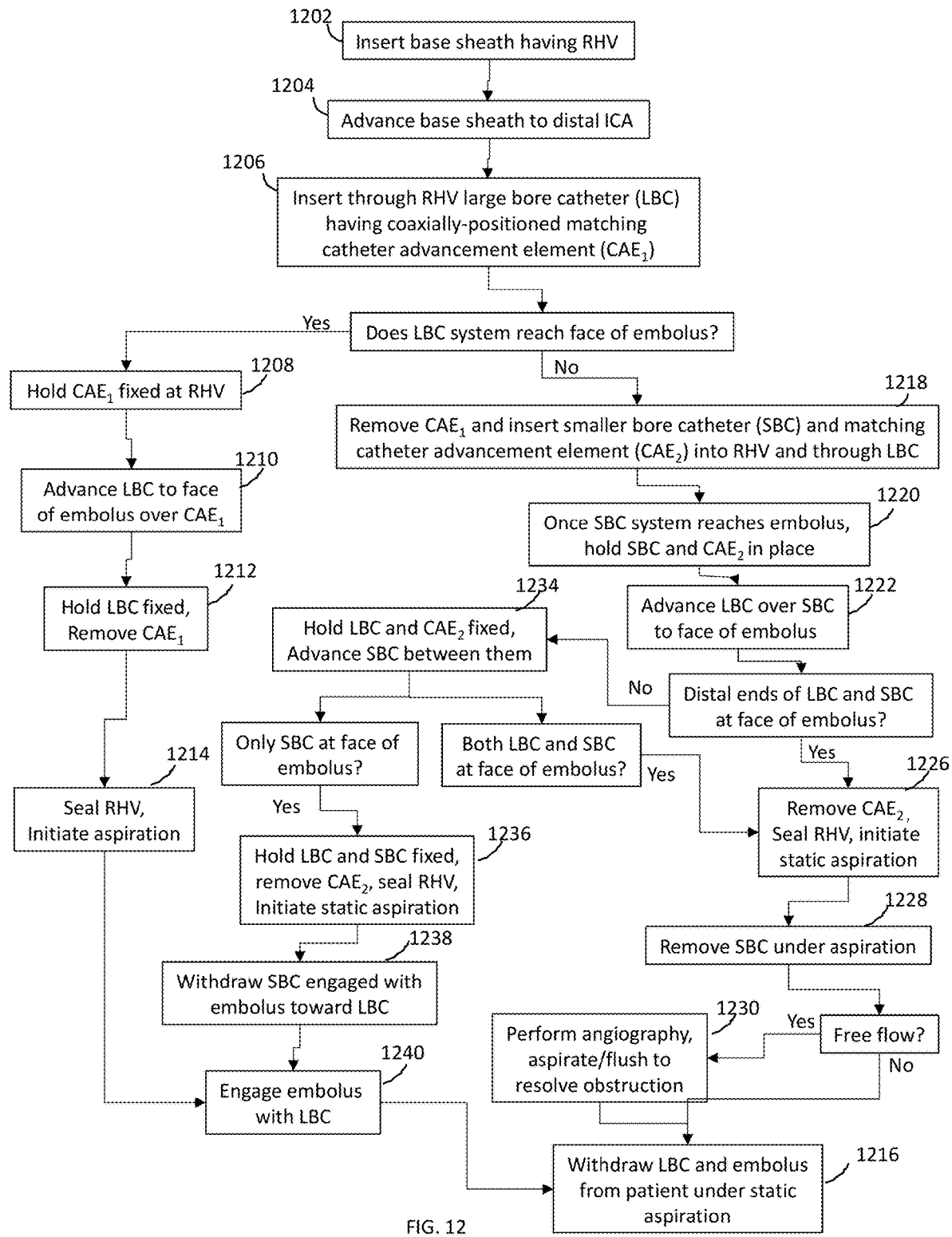
FIG. 12 illustrates an implementation of a sequential method of aspiration-only thrombectomy.

FIG. 12 illustrates an implementation of a method of aspiration-only thrombectomy. Each catheter system (i.e. the catheter and matching catheter advancement element) is preassembled and sequentially inserted through the RHV. FIG. 12 shows a base sheath inserted into a vessel (Box 1202). The base sheath is advanced until a distal end region of the base sheath is positioned distal to the common carotid artery such as within the distal ICA (Box 1204). A large bore catheter LBC arranged coaxially with a matching catheter advancement element $CAE_1$ is inserted through the RHV of the base sheath (Box 1206) and advanced out through the distal end of the base sheath. The large bore catheter LBC preferably has the largest inner diameter for aspiration that is desired to perform thrombectomy (e.g. 0.088" inner diameter). The large bore catheter LBC and its catheter advancement element $CAE_1$ are advanced together through the same RHV in an advancement configuration, for example, using a single pinch on one hand.

If the coaxial system is advanced sufficiently such that the catheter advancement element $CAE_1$ reaches the face of the embolus, the catheter advancement element $CAE_1$ is held fixed at the RHV (Box 1208) and the large bore catheter LBC is advanced further distal to the face of the embolus over the catheter advancement element $CAE_1$ (Box 1210). Once the large bore catheter LBC reaches the face of the embolus, the catheter advancement element $CAE_1$ is withdrawn while the large bore catheter LBC remains held in position at the face of the embolus (Box 1212). The RHV is sealed and aspiration is initiated, for example, through the side arm of the RHV (Box 1214). As will be discussed in more detail below, the aspiration can be static or cyclic aspiration. The large bore catheter LBC engages the embolus (Box 1240). If the distal end of the catheter is "corked", the large bore catheter LBC is withdrawn under static aspiration along with the embolus captured at the distal end (Box 1216).

Again with respect to FIG. 12, the large bore catheter LBC may not reach the face of the embolus on the first attempt due to its large dimension. If the large bore catheter LBC does not reach the face of the embolus, a smaller bore catheter SBC and matching catheter advancement element $CAE_2$ are inserted into the RHV and through the lumen of the large bore catheter LBC (Box 1218). The smaller bore catheter SBC can have an inner diameter that is less than 0.088", for example, 0.072". The smaller bore catheter SBC is advanced similarly as the first coaxial catheter system through the large bore catheter LBC, which remains held in place. Upon reaching a target advancement location, the smaller bore catheter SBC and matching catheter advancement element $CAE_2$ are held in place (Box 1220) and the large bore catheter LBC advanced over the smaller bore catheter SBC (Box 1222) until the large bore catheter LBC reaches the face of the embolus (1224). The large bore catheter LBC and smaller bore catheter SBC are advanced until the distal ends of both catheters reach the embolus face. The catheter advancement element $CAE_2$ is removed and static aspiration initiated (Box 1226). The smaller bore catheter SBC is removed from the system under static aspiration (Box 1228). If free flow is established with aspiration, the large bore catheter LBC is left in position and gentle angiography performed to reconstitute antegrade flow and resolve the obstruction (Box 1230). If free flow is not established, the static aspiration is continued and the large bore catheter LBC is withdrawn to remove the embolus using the higher flow and forces generated by the larger catheter without the smaller bore catheter SBC obstructing flow within its lumen (Box 1216). If the large bore catheter LBC does not reach the face of the embolus by crawling over the smaller bore catheter SBC, the large bore catheter LBC and the catheter advancement element $CAE_2$ of the smaller bore catheter SBC are held fixed at the RHV and the smaller bore catheter SBC advanced between them (Box 1234). The step is repeated sequentially to inch both catheters to the face of the embolus. If only the smaller bore catheter SBC reaches the face of the embolus, the catheter advancement element $CAE_2$ is removed, the RHV sealed, and static aspiration initiated (Box 1236). The smaller bore catheter SBC is used to draw the embolus towards the large bore catheter LBC (Box 1238). Static aspiration is applied through the large bore catheter LBC to engage the large bore catheter LBC with the embolus (Box 1240). As will be discussed in more detail below, the aspiration applied can be static or cyclic dependent on status of the method and whether or not the embolus is "corked" or engulfed. If the large bore catheter LBC is "corked" and not progressing, the large bore catheter LBC is withdrawn under static aspiration with the engaged embolus (Box 1216).

Tension can get stored in a catheter system advanced through tortuous cerebral anatomy. Downward and lateral forces may be created on the supporting catheter system as the distal tip of the catheter meets resistance. The entire system can propel forward as the distal tip of the catheter is released past these points of resistance. The resistance can occur at the tortuosity in the vessel or at obstructions or bifurcations or due to preexisting implants or other causes. Typically, the tension is stored without loss of position. The resultant effect is a back-and-forth type movement of the system to reach the target and the steady storage of tension in the guide sheath as it is relentlessly pushed downward (i.e. proximally back against the direction of insertion).

In the case of aspiration systems for stroke, the same stored tension can occur with advancement of a larger bore catheter (e.g. an 0.088" ID catheter). As the larger bore catheter develops stored tension and the operator tries to advance it to the target embolus (e.g. in the M1 branch of the MCA), the larger bore catheter traverses the anatomy in a "greater curve to greater curve" manner introducing an amount of slack in the system. The stored tension creates the resistance that causes a catheter to jam at a point and not reach a target. Should the larger bore catheter not reach the target, a smaller bore catheter can be advanced to reach the embolus due to smaller diameter and better deliverability. The smaller bore catheter can navigate the stored tension and also navigate the anatomy in a "greater curve to greater curve" manner as the larger bore catheter did. The smaller bore catheter can anchor onto the embolus via the aspiration pressure applied through the system. The smaller bore catheter can be fixed at the point of occlusion and aspiration turned on to maximum (e.g. via a pump). This affixes or anchors the smaller bore catheter to the embolus such that the operator can "straighten" the entire system and thereby apply a proximally-directed force on the smaller bore catheter to remove slack relative to the surrounding anatomy while the distal end of the smaller bore catheter remains anchored onto the occlusion. The catheters once the slack is reduced now traverse the anatomy in a "lesser curve to lesser curve" manner rather than a "greater curve to greater curve" manner thereby straightening their course relative to the surrounding anatomy. A straightened course allows the larger bore catheter to be advanced over the anchored smaller bore catheter such that its distal end can also reach the embolus target. Aspiration and anchoring through the smaller bore catheter is maintained and the operator creates a straighter, tension-free course to "rail" the larger bore catheter through it over the smaller bore catheter. Once the larger bore catheter is in place—even if the larger catheter does not reach the embolus—substantial embolic protection is afforded and off-target-embolization avoided, particularly if the larger bore catheter is placed distal to the nearest bifurcation proximal to the embolus site.

Once the larger bore catheter is in position, the smaller bore catheter extending through it can be withdrawn. Aspiration may still be applied by the single vacuum source and the seal between the corked embolus maintained as the smaller bore catheter is withdrawn towards the distal end of the larger bore catheter. Once the smaller bore catheter is pulled into the distal end of the larger bore catheter, the aspiration pressure may be automatically turned on within the larger bore catheter such that the embolus is captured within the lumen of the larger bore catheter. Due to the larger inner diameter, the embolus under continuous aspiration pressure via the single, shared vacuum source will likely evacuate the embolus. The smaller bore catheter and the larger bore catheter can both be withdrawn from the system.

Many operators prefer to assemble coaxially the devices to be used in sequence. An interrelated variant of the aspiration-only thrombectomy method involves preassembling the large bore catheter and the smaller bore catheter so that they may be advanced together with a catheter advancement element for the smaller bore catheter through the base sheath. Each of the methods can be performed without a guidewire or microcatheter and without any component being advanced distal to the embolus. The smaller bore catheter and matching catheter advancement element are preassembled outside the patient coaxially within the large bore catheter. A base sheath having an RHV is inserted into a vessel (Box 1302). The base sheath is advanced until a distal end region of the base sheath is positioned distal to the common carotid artery such as within the distal ICA (Box 1304). The preassembled system of devices is inserted as a unit into the base sheath (Box 1306) and advanced out through the distal end of the base sheath. Upon the catheter advancement element CAE of the smaller bore catheter SBC reaching the target location, the catheter advancement element CAE is held fixed (Box 1308) and its smaller bore catheter SBC advanced over it to the embolus face (Box 1310). The catheter advancement element CAE is removed while the smaller bore catheter SBC is held fixed (Box 1312). The smaller bore catheter SBC engages the embolus and static aspiration initiated (Box 1314). The smaller bore catheter SBC is withdrawn slightly to create a straighter "rail" and to confirm anchoring of the distal end of the smaller bore catheter SBC on the embolus (Box 1316). With the rail in place, the large bore catheter LBC is advanced to the embolus face over the smaller bore catheter SBC anchored to the embolus (Box 1318). Once the distal ends of the smaller bore catheter SBC and the large bore catheter LBC are in place at the embolus, clot engagement is confirmed by cessation of free flow (Box 1320). The smaller bore catheter SBC is left in place for a period of time (e.g. greater than about 90 seconds) and slowly withdrawn under static aspiration leaving the large bore catheter LBC in place (Box 1322). If cessation of flow persists, the smaller bore catheter SBC is removed completely under static aspiration. If cessation of flow continues to persist (Box 1324), the large bore catheter LBC is withdrawn under static aspiration (Box 1326).

As discussed above, the method can be performed without a guidewire or microcatheter and without any component being advanced distal to the embolus. However, the method can include the use of a guidewire (whether in the one-at-at-time approach or the preloaded approach). The guidewire can be positioned within the catheter advancement element and exit the RHV either directly or out the hub of a delivery catheter designed to have a guidewire its full-length. The guidewire can be advanced to the target or across the embolus and then held in position with the lead coaxial system is advanced over it. The guidewire can also be advanced to a fixed distance ahead of the lead coaxial system so that it "leads" the advancement of the entire system of components. The guidewire can also be positioned within the lead coaxial system, but not leading it. Rather, the guidewire can be withdrawn yet available should a guidewire be needed to advance the lead coaxial system to the target. The guidewire usage may be adjusted based upon operator preference, anatomic challenges, clinical features of the patient, etc.

Figure 13:
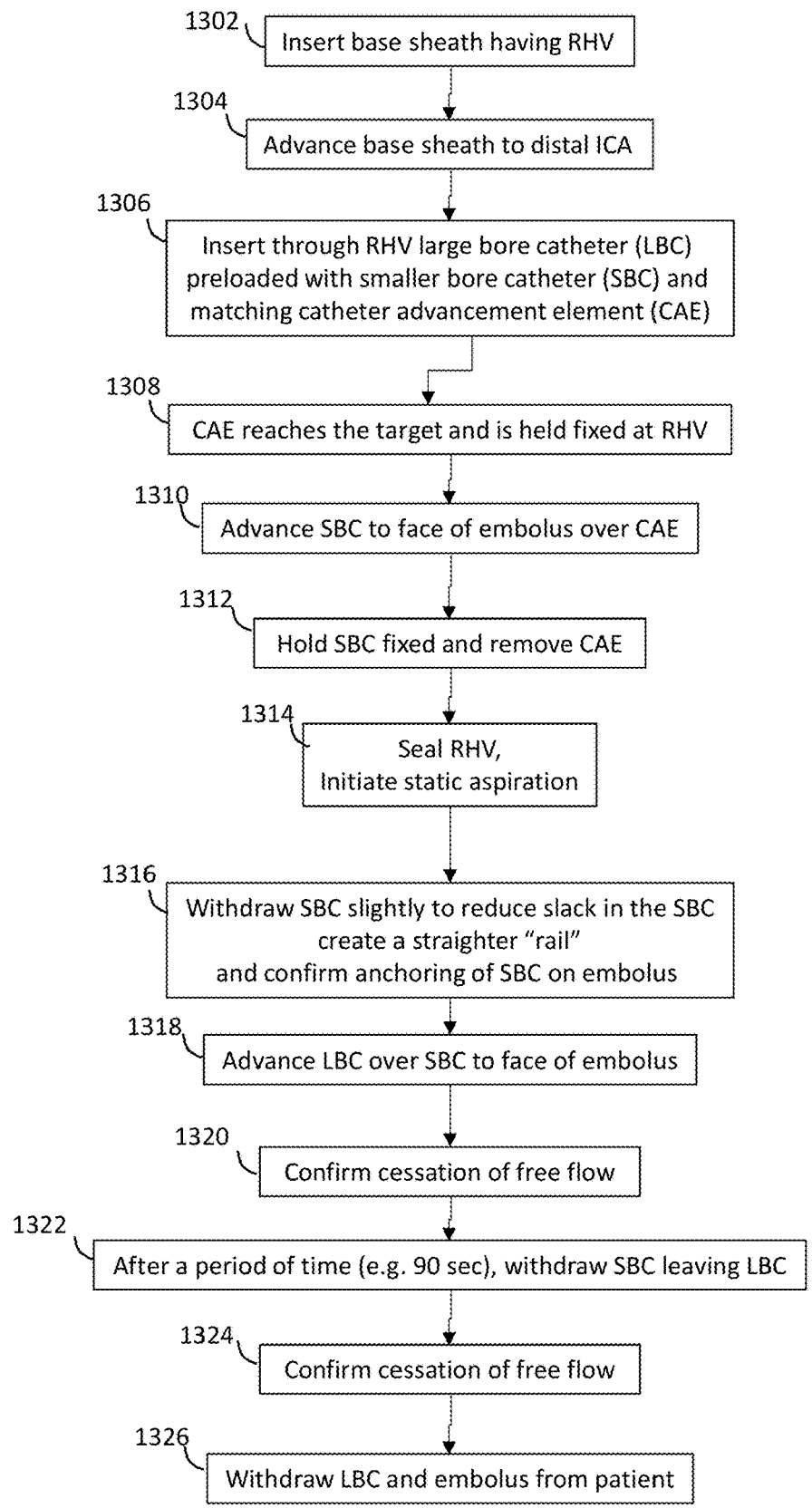
FIG. 13 illustrates an implementation of a preloaded method of aspiration-only thrombectomy.
Figure 14:
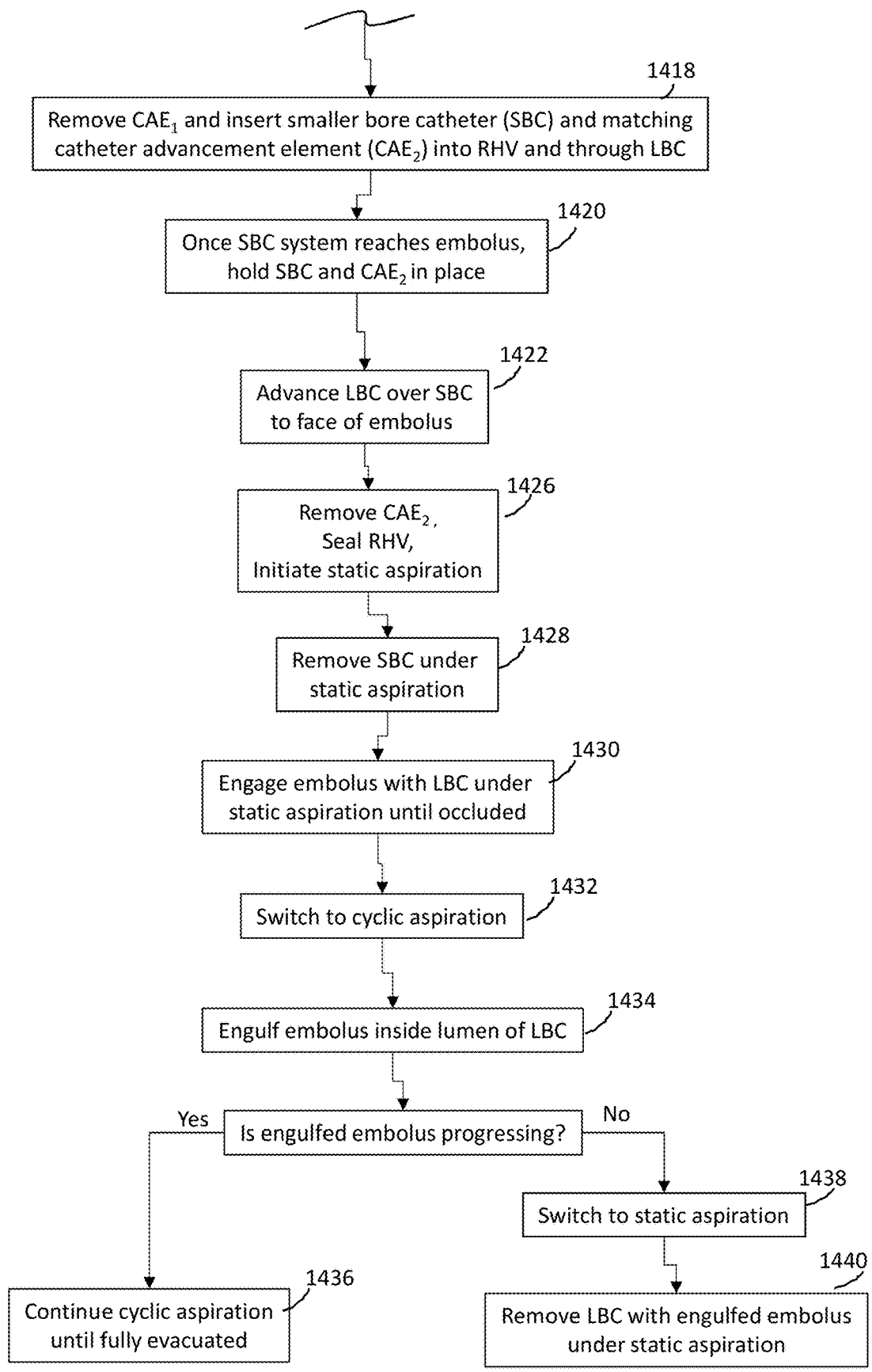
FIG. 14 illustrates an implementation of a method of aspiration-only thrombectomy incorporating cyclic aspiration.

The aspiration used in the methods described about and methods shown in FIG. 12 or FIG. 13 may include static aspiration and cyclic aspiration. Whether the pressure is held static or cycled can depends upon the stage of the method, progress of evacuation, and the nature of the embolus. FIG. 14 illustrates a variation of the method shown in FIG. 12 where a smaller bore catheter SBC and matching catheter advancement element $CAE_2$ are inserted into the RHV through a lumen of an already positioned large bore catheter LBC (Box 1418). As in the method of FIG. 12, once the smaller bore catheter system reaches the embolus, the smaller bore catheter SBC and the catheter advancement element $CAE_2$ are held in place (Box 1420) and the large bore catheter LBC advanced over the small bore catheter SBC to the face of the embolus (Box 1422). The catheter advancement element $CAE_2$ is removed, the RHV sealed, and static aspiration initiated (Box 1426). The smaller bore catheter SBC is removed under static aspiration (Box 1428). Once the distal tip of the large bore catheter LBC is occluded by the embolus (Box 1430), the static aspiration is switched to cyclic aspiration (Box 1432). Cyclic aspiration aids the large bore catheter to fully engulf the embolus inside its lumen (Box 1434). Cyclic aspiration continues while the engulfed embolus progresses through the lumen of the large bore catheter LBC until, desirably, it is fully evacuated from the patient (Box 1436). However, if the engulfed embolus fails to progress through the lumen and there is cessation of flow, the cyclic aspiration is switched back to full static aspiration (Box 1438). The large bore catheter LBC is withdrawn with the embolus still engulfed in the lumen under static aspiration and removed from the patient (Box 1440).

The catheter advancement element allows for the delivery of much larger size catheters to the levels of the cerebral anatomy typically seen in large vessel occlusion in acute ischemic stroke. As an example, the target embolus can be in the M1 segment of the middle cerebral artery, which can accommodate a large bore catheter having an ID much greater than 0.050", such as an 0.088" inner diameter catheter that can have an outer diameter of 2.6 mm or greater. A typical M1 segment as measured from a population of computed tomographic images of stroke patients is 3.1±0.4 mm suggesting a distribution where 95% of the population will accommodate a 2.6 mm catheter (see Rai A. T. et al. "Cerebrovascular geometry in the anterior circulation: an analysis of diameter, length and the vessel taper" *JNIS* 2013; 5:371-375). As the size of the catheter gets closer and closer to the size of the offending embolus, the likelihood that the aspiration catheter will engulf and completely evacuate the embolus into the syringe or pump canister increases. This will also increase the likelihood the aspiration catheter will be successful in the primary removal of the embolus and recanalization of the artery rather than the embolus "corking" in the catheter tip. Withdrawing a catheter corked with an embolus has the drawbacks of potential fragmentation and distal embolization within the vessel as the exposed embolus is traumatized during withdrawal through narrow vessels and tortuous bends.

Catheters having an 0.088" inner diameter can be navigated through tortuous anatomy, for example, with the help of the catheter advancement element described herein, to reach an embolus having a diameter that approximates the inner diameter of the catheter. Aspiration applied through these large-bore catheters can capture and fully engulf the embolus more quickly and with fewer drawbacks of fragmentation and distal embolization.

Emboli found in stroke can be heterogeneous from patient to patient. The ability of a catheter to fully engulf an embolus in the stroke setting may vary depending on the consistency of the embolus and patient conditions. The likelihood the catheter will successfully engulf the embolus increases for the larger bore sized catheters assuming the distal end of the catheter can be brought into close approximation with the embolic target. If the distal end of the catheter is too far away from the embolus target, aspiration through the catheter will simply draw in blood from the intrinsic antegrade flow proximal to the embolic occlusion. The catheter advancement element aids in advancing larger bore catheters that come close in size the target vessel directly to the face of the embolus thereby improving recanalization rates with a variety of embolic types due to the increased likelihood of complete engulfment of the clot and any embolic fragments that would otherwise travel downstream. The catheters described herein can include a proximal control element (see, for example, proximal control element 230 in FIG. 3) and thus, undergo a significant step-up in inner diameter moving proximally along the system. The aspiration performance is greatly improved compared to standard catheters in which no significant step-up in inner diameter occurs, which can further contribute to increased likelihood of full engulfment (see, e.g., Arslanian R. A. et al. "Pump or Syringe? Evaluation of Aspiration Efficacy with Neurovascular Catheters." SNIS, 2018)

Changing the aspiration force during a procedure, referred to herein as cyclic aspiration, can aid in the success of capturing an embolus over static or near static application of aspiration. Cyclic aspiration can be incorporated as part of the methods described above in order to improve outcomes. In some implementations, the cycling can be performed according to methods in Simon et al. *J. Neurointerv. Surg.* 2014, November; 6(9):677-83, which is incorporated by reference herein. Simon et al. described cyclic aspiration in a cerebral thrombectomy model improving overall emboli removal versus static aspiration in terms of speed and overall clearance of synthetic clots in an experimental model. Increasing cycling frequency, using specific pressure cycle waveforms and water rather than air as the aspiration medium all improved efficacy of aspiration. Introduction of cyclic aspiration forces in suction thrombectomy can generate clot fatigue and by fatiguing the clot, the aspiration performance can be measurably improved compared to static forces of conventional suction thrombectomy techniques. Cyclic aspiration creates a dynamic pressure curve where the pressure cycles between a maximum and minimum value at a specific frequency (maximum and minimum relative to the magnitude of pressure) or cycles between a specific range or recipe of frequencies.

In some implementations, the aspiration catheter systems described herein can be coupled by a vacuum line 502 to a vacuum source 505. The vacuum source 505 can vary in its configuration. The vacuum source 505 can be an active source of aspiration such as an aspiration pump, a regular or locking syringe, a hand-held aspirator, hospital suction, or the like, configured to draw suction through the working lumen of the base sheath. As described above, the RHV of the base sheath may be sealed and aspiration initiated via a side arm of the RHV. The side arm of the RHV can be coupled to any of a variety of vacuum sources. In a preferred implementation, the vacuum source 505 is an aspiration pump such as the Gomco 405 Tabletop Aspirator (Allied Healthcare Products, Inc., St. Louis, Mo.). The aspiration pump may incorporate a programmable pump motor, such as motor controlled by a pulse width modulation, a brushless motor and controller or similar controllable motors. Alternatively, a controllable valve may be used to conduct the cyclic aspiration as described herein. In another preferred implementation the vacuum source 505 is a locking syringe, such as a VacLok type syringe.

Material aspirated from the aspiration catheter system can be collected within a proximal vacuum canister 510 connected to the vacuum line 502. In some implementations, the proximal vacuum canister 510 can itself be the vacuum source 505, such as a barrel of a locking syringe (see FIG. 5). In other implementations, the proximal vacuum canister 510 is coupled to the vacuum source 505 via tubing 512 (see FIGS. 4A-4D).

Figure 16B:
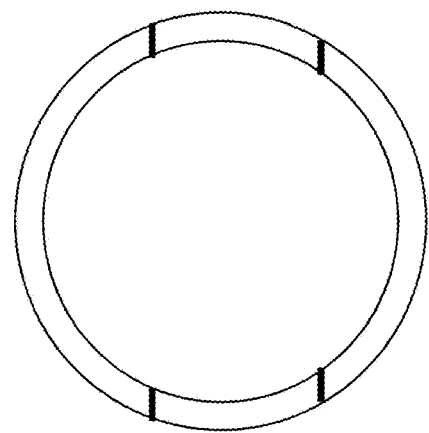
FIG. 16B is a cross-sectional view of the fitting of FIG. 16A taken along line B-B.
Figure 16A:
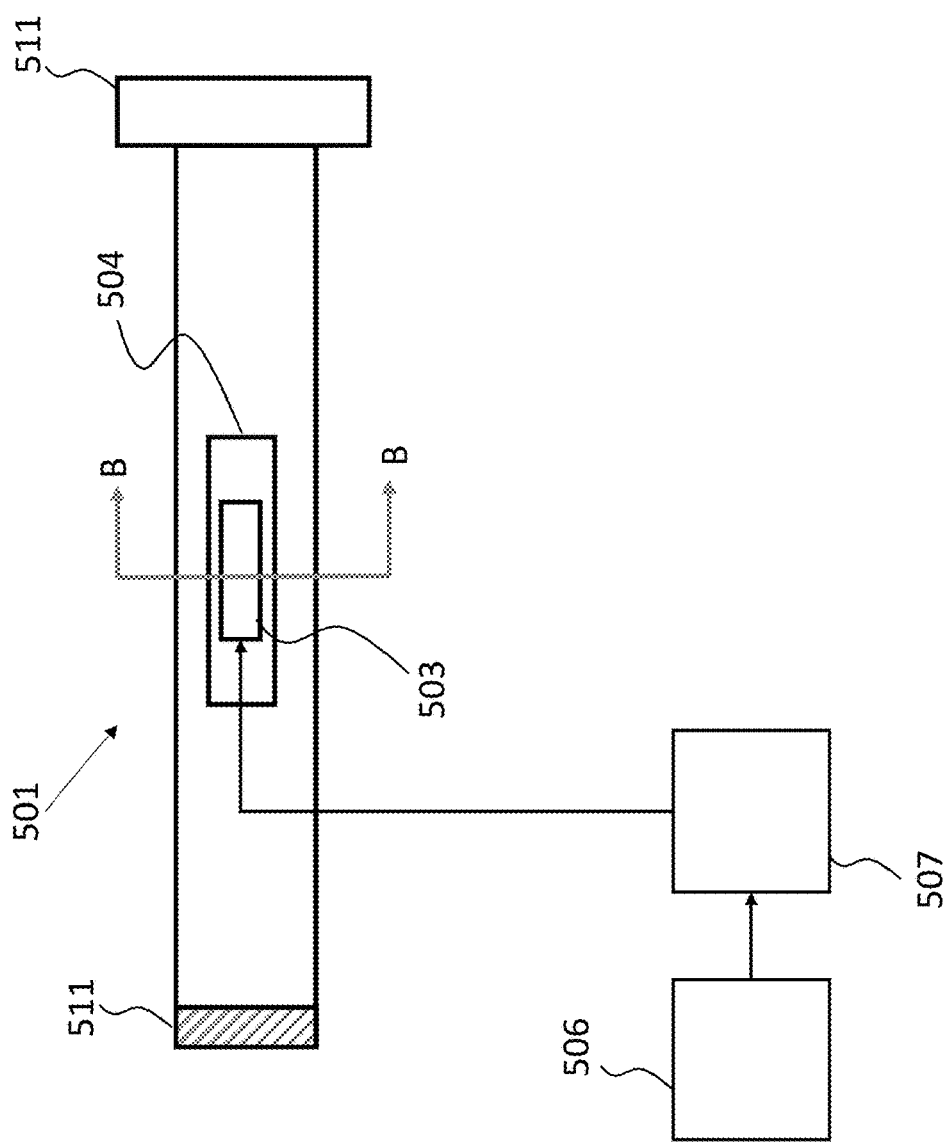
FIG. 16A is a schematic diagram of a fitting for use with a vacuum line.

As blood flows through the vacuum line 502 and into the proximal vacuum canister 510, it can be difficult to visually identify if any clot has been removed by the aspiration procedure. Therefore, there is a need for an improved system that can be easily adapted to any vacuum line that provides for confirmation of detection of clot during aspiration. In an implementation and as shown in FIGS. 16A-16B, the vacuum line 502 can further include an in-line fitting 501 in fluid communication with the vacuum line 502 coupled to the vacuum line 502 via luers 511 or similar coupling feature. The fitting 501 includes an emitter 503 and a receiver 504 disposed opposite to each other. The emitter 503 emits a signal, such as but not limited to an infrared light, which is received by the receiver 504. Fitting 501 is further coupled to a power source 506 and a display 507, wherein the display 507 may be embodied as one or more LED indicators or may be embodied as a visible display such as a LED, LCD, paperwhite or similar lower power display module. In use, as blood flows through the vacuum line 502, the blood passes through the fitting 501 and past the emitter 503 and receiver 504. Should any clot be disposed within the blood flowing through the vacuum line 502, the clot would block the emitted light as it passes in front of the emitter 503. The receiver 504 would then detect that the emitted signal has been blocked by the clot and then provide a notification that embolus has been detected in the blood flowing past the fitting 501. FIG. 16B is a cross-sectional view of the fitting 501 of FIG. 16A taken along line B-B.

The cyclic aspiration force can be enabled through one or more valves 515 positioned between the vacuum source 505 and the distal end of the catheter of the aspiration catheter system 500, which is shown schematically in FIG. 4A-4D. The valve 515 can control patency between the vacuum source 505, the catheter tip, and an external environment that provides the pressure differential. The valve 515 can establish open continuity between the vacuum source 505, the catheter tip, and the external environment (e.g. air) when the valve 515 is opened. Temporarily closing the valve 515 to the external environment (e.g. manually, mechanically, or via software programming on a pump) can allow the vacuum source 505 to establish a vacuum at the catheter tip whereas subsequently opening the valve 515 to the external environment diminishes the vacuum at the catheter tip in a controlled manner. Repeatedly opening and closing the valve 515 develops cyclic pressure profiles at the catheter tip. Changes in the operation of the valve 515 produces different cyclic aspiration profiles at the catheter tip and can be tailored to maximal efficacy for each patient.

The valve 515 can be a three-way valve (Harvard Apparatus, Holliston, Mass.). The valve 515 can vary in its configuration including any of a variety of valves, valve types, valve/fitting combinations, as well as any of a variety of external environments. The valve can be pneumatic, electromechanical, mechanical, or other type of valve. In some implementations, the valve 515 can be a solenoid valve.

Figure 4A:
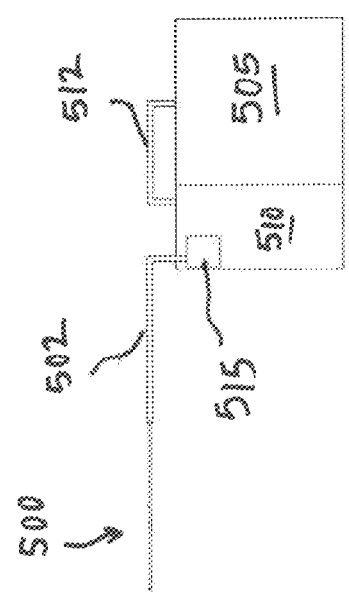
FIGS. 4A-4D are schematic views of various implementations of a cyclic aspiration system.
Figure 4B:
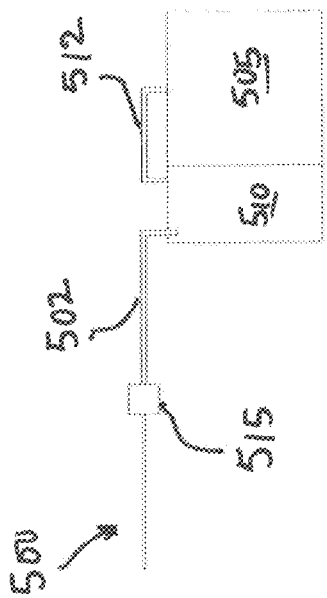
Figure 4C:
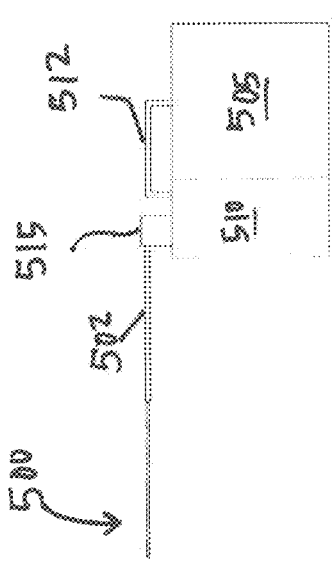
Figure 4D:
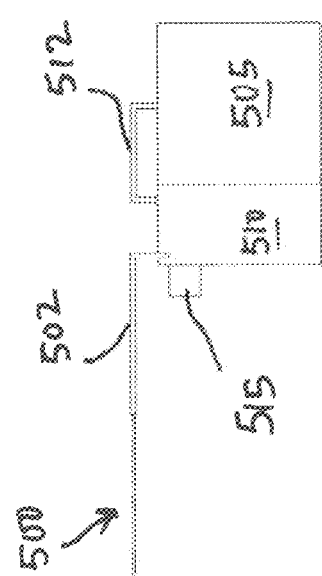
Figure 6A:
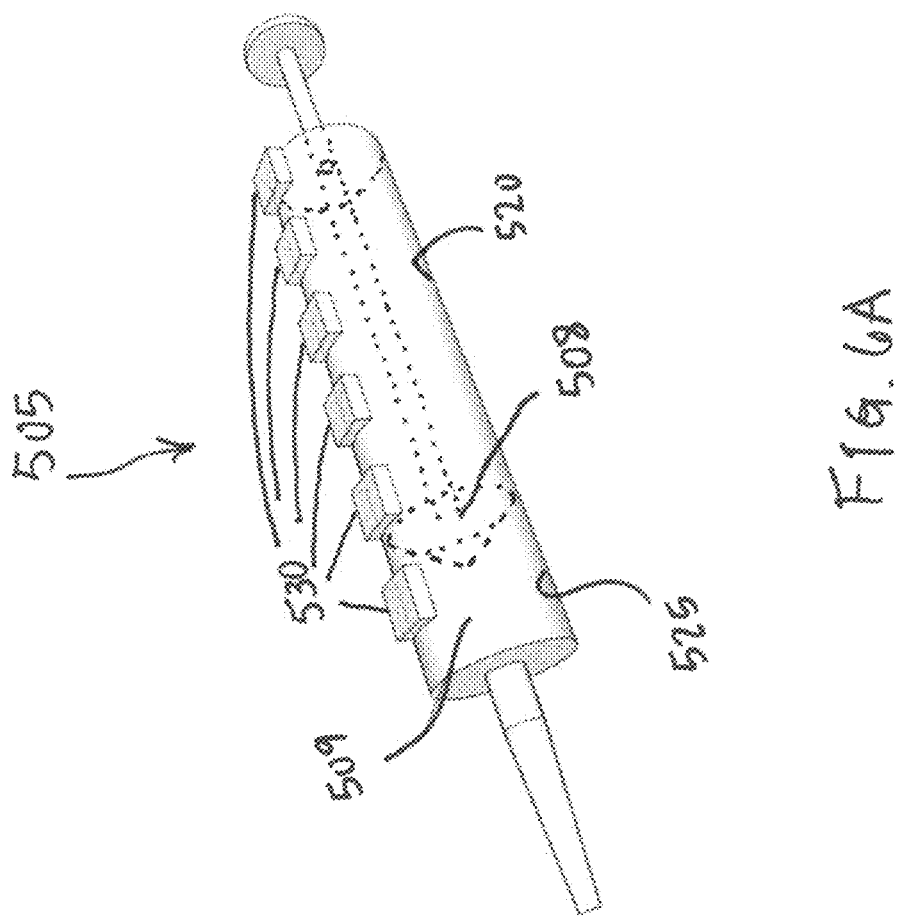

The valve 515 can be positioned in various locations. FIG. 4A shows a pneumatic valve 515 located on the vacuum line 502 near a proximal section bridging the proximal canister 510 and the catheter system 500. The valve 515 may be positioned anywhere along a length of the tubing 502. FIG. 4B shows the valve 515 located inside the proximal vacuum canister 510. The valve 515 can be positioned attached to or near an outlet from the canister 510 to the catheter line 502. FIG. 4C shows the valve 515 located on a surface of the proximal canister 510. The valve 515 can be located on an outer surface, an inner surface, or embedded/integrated into the wall of the canister 510. FIG. 4D shows the valve 515 located on a distal end of the vacuum line 502 bridging the canister 510 and the catheter system 500. The valve 515 can be integrated into the catheter system 500. The valve 515 can be incorporated into the RHV attached to the guide sheath. The valve 515 can include a connection for the vacuum line 502 as well as another connection for the proximal end of the catheter system 500. Additionally, more than one valve 515 may be used. The multiple valves 515 may be serially coupled in fluid communication, or may be coupled in a parallel configuration, wherein each valve may be controlled or programmed to cycle at different frequencies/times, thereby providing a surgeon multiple different cyclic aspiration cycles or allowing multiple different cyclic aspiration cycles to be utilized simultaneously or in series.

FIG. 5 shows a valve 515 designed to connect to a vacuum source 505. In this implementation, the vacuum source 505 can be a standard syringe or other manual vacuum forming mechanism. The valve 515 can connect directly or indirectly to the syringe via tubing 502.

The valve 515 can be controlled electronically such as with a microcontroller relay system or by another mechanism to create a cyclic pressure environment by alternately opening and closing a connection between the aspiration column (sometimes referred to herein as the inter-catheter environment) that is under vacuum pressure and another environment of different ambient pressure, such as the ambient room pressure or some other controlled pressure chamber. The valve 515 can also be controlled via a manual actuation such as a button press, a predetermined cycle, or by detecting vacuum pressure within the line. In some implementations, the valve 515 may be controlled upon the system detecting the plunger 508 in the syringe barrel 509 is withdrawn.

In an implementation, the vacuum source 505 is a syringe configured to provide cyclic aspiration perturbations through its operation. The syringe can include one or more mechanisms within the syringe barrel 509 that move (independently or in tandem) so as to oscillate the applied aspiration pressure during use.

FIGS. 6A-6D show a vacuum source 505 that is a syringe configured to provide cyclic aspiration directly without the need for a valve. The syringe can have a plunger 508 positioned within a syringe barrel 509 dividing the syringe barrel 509 into a first region 520 located proximal of the plunger 508 and a second region 525 located distal of the plunger 508. The size of the first and second regions 520, 525 varies depending on the position of the plunger 508 within the barrel 509. As with conventional syringes, the plunger 508 seals with the inner wall of the syringe barrel 509 to form a vacuum within the syringe barrel 509 distal to the plunger 508 as the plunger 508 is withdrawn. As best shown in FIGS. 6A-6D, the syringe barrel 509 can incorporate one or more bridges 530. The bridges 530 can be indentations or imperfections in the wall of the syringe barrel 509 resulting in a break of the seal between the inner wall and the plunger 508. Positioning the plunger 508 between the bridges 530 allows for the plunger 508 to seal with the wall of the syringe barrel 509 typical in syringes (see FIGS. 6B and 6D). Sealing between the plunger 508 and the inner wall of the syringe barrel 509 prevents fluid communication between the first region 520 and the second region 525. Positioning the plunger 508 within the region of a bridge 530 allows for fluid communication between the first region 520 and the second region 525 past the plunger 508 (see FIG. 6C). The air within the first region 520 proximal of the plunger 508 can enter the second region 525 of the syringe barrel 509 distal to the plunger 508. The first portion 520 of the syringe barrel 509 can be at ambient pressure and the second portion 525 of the syringe barrel 509 distal to the plunger 508 can be under vacuum. During retraction of the plunger 508, vacuum is created in the second portion 525 of the syringe barrel 509. However, some vacuum is lost as the plunger 508 slides past each bridge 530. Speed of retraction of the plunger 508 can be sufficient to maintain at least some vacuum within the distal portion 525. Retraction of the plunger 508 within the syringe barrel 509 causes vacuum created within the distal portion 525 to be lost, regained, and then lost again as the plunger 508 moves past each bridge 530 thereby creating pulsatile or cyclic aspiration patterns at the distal end of the catheter.

Geometry of the syringe barrel and the bridges 530 can be designed to achieve specific cyclic profiles of pulsatile aspiration. For example, the syringe barrel length, inner diameter, distance between bridges 530, number of bridges 530, size of bridges 530 (length, width, depth, etc.) can each be varied to achieve a particular cyclic pattern. Syringes can be designed for specific plunger retraction speeds (or typical retraction speeds) to provide ideal cyclic profiles. Additionally, a one-way valve 515 can be installed or integrated into the system such that, once the plunger 508 is retracted fully it can be depressed again without loss of vacuum in the catheter line in order to facilitate multiple pulls and extended treatment time without the need for changing out the syringe. The vacuum source 505 can be the sole source of aspiration or can be utilized in tandem with another source of aspiration to provide just the cyclic pressure relief sections of the aspiration curve. For example, a tee can be placed in the aspiration line just before the catheter with one end of the tee connected to the catheter, another to a vacuum source (e.g. a Gomco Tabletop Aspirator Pump) and the final end to the syringe vacuum source 505. A cyclic aspiration profile can be attained with the Gomco Tabletop Aspirator Pump providing the base aspiration and actuation of the syringe vacuum source 505 providing the requisite pressure cycling. Similar manual or mechanical mechanisms to a syringe such as the one detailed in FIG. 6A can be used for direct or indirect cyclic aspiration.

In an implementation, the valve 515 can control aspiration pressure profile by rotating between a "closed" and an "open" state. The speed of rotation can control the cyclic aspiration pressure profile.

In an implementation, a cyclic aspiration pressure profile can be achieved via a tactile device configured to augment the movement of a user such as a surgeon or other medical practitioner such that cyclic aspiration may be performed manually. For example, a user may perform an "on"-"off" cycle by motion of a user's finger relative to a trigger device. The control of aspiration can also be controlled manually by use of a foot pedal or other actuation device known in the art. Manual control of the aspiration can also provide feedback to the user, such as tactile, audio, visual, or a combination thereof.

The cyclic aspiration can involve fast pressure cycling, for example, between 1 Hz and 100 Hz. The cycling can be performed at a single frequency, multiple frequencies, a dynamic array or recipe of frequencies, and for extended periods of time. A pressure cycling mechanism such as a solenoid valve in or near the vacuum line to the catheter, to work in tandem with an aspiration pump to apply fast oscillations in pressure. These pressure oscillations, or cycles, improve the clot removal capability of aspiration catheters and, in general, the pressure oscillating device is most effective if the distance between the pressure oscillating device and the catheter tip is minimized as pressure losses are minimized. Because the cyclic aspiration system hinges around an independent pressure oscillating mechanism it can be easily integrated into current aspiration thrombectomy systems without the need to replace the entire or existing vacuum pump assembly.

In an implementation, the cyclic frequency can be between 1 Hz and 50 Hz, and more preferably between 2 Hz and 10 Hz. In an implementation, the cyclic pressure profile includes a fast "burst" of higher frequency cycles within the frequency range (e.g. approximately 10 Hz) followed by a section of either static aspiration or slow "recovery" frequency cycles within the frequency range (e.g. approximately 3 Hz). The static or slow cyclic profile following the period of higher frequency cycles allows for building up pressure to a maximum operating pressure after pressure deteriorates at the high-speed cycling. For manual systems, aspiration cycles can include cycling between −23.8 inHg and 0 inHg at 1 Hz; cycling between −22 inHg and 0 inHg at 2 Hz; and cycling between −18.9 inHg and −5.0 inHg at 6.3 Hz. Cycling can be in the range of between 1 Hz and 3 Hz or between 1 Hz and 6 Hz, or between 1 Hz and 10 Hz, or between 1 Hz and 50 Hz. Generally, cycling can be below frequencies that increase the risk of compromising a vessel wall or increasing hemorrhage or thermal tissue damage. Low frequency mechanical perturbations should not exceed local elastic limits.

Cycling aspiration (e.g. up to about 6.3 Hz) in a catheter having a proximal control element 230 (sometimes referred to herein as a "tethered catheter") for acute ischemic stroke where the aspiration physics are already enhanced can provide the additional therapeutic effect of material fatigue and then fracture of the embolus. In a procedural sense, cycling can allow for both engulfment and evacuation or clearance of the embolus, but also provide embolic protection from downstream loss of debris into the distal vascular bed based upon better communication of the aspiration force beyond the catheter tip once the obstruction of the emboli at the catheter tip is eliminated. Cyclic aspiration enhances primary embolus capture within the catheter and restores flow more quickly and thus also imparts better distal protection. A larger bore catheter can be delivered further distally to engage the emboli at the face of the offending mass using the catheter advancement element further increasing the likelihood of success of the aspiration embolectomy.

The cyclic aspiration profile can be controlled to provide dynamic cycles, stable cycles, and/or "smart" cycles. The cyclic aspiration profile can be tailored to the treatment scenario to provide the best chance of clot removal. The intensity, duration, and frequency of cyclic aspiration may be changed dynamically (i.e., creating dynamic cycles) to improve treatment. For example, specific frequencies may be more or less effective at aspirating clots depending on clot material properties. If a patient has presented with stroke symptoms for 4 hours before treatment then a lower frequency in the range of 1-4 Hz may be employed whereas if a patient has presented with symptoms for 7 hours another higher frequency in the range of 3-10 Hz may be employed. Additionally, "test" or "echo" cycles may be applied to gauge the clot consistency, which can be used to guide the cyclic frequency used during a procedure. The test cycles can be automated within the cyclic aspiration system. As described above, another application of this can be fast "destructive" cycles that can be applied for a maximum time before the average vacuum pressure decreases too much, after which "recovery" cycles or static aspiration is applied. The recovery period allows for building the vacuum pressure back to maximum levels. This can include cycling at 10 Hz for 3 seconds followed by 7 seconds of static aspiration for an average of 3 Hz cycling, but more effective than a continuous 3 Hz profile. In other situations, a stable cyclic pressure environment where the cyclic pressure profile is consistent over time and the frequency remains unchanged may be more beneficial. For example, a 5 Hz cyclic aspiration for 10 minutes for clot retrieval can be used. Aspirating with a set frequency for a period of time can be more effective with clots that are more likely to release distal emboli. The cycling can improve clot retrieval while minimizing clot breakup outside of the catheter. Additionally, "smart" cycles may be incorporated whereby different degrees of dynamic and stable cycles are used based on patient and vascular feedback to maximize treatment efficacy. As an example, a patient or vascular response to a pressure profile may be sensed and/or recorded within the cyclic vacuum system. The pressure profile may be compared to a different aspiration scenario (e.g. open catheter tip, corked tip, corked at some distance up the catheter line) to provide insight into material properties of the clot such as clot consistency, location, velocity, and optimal pressure profile for removal. Modal analysis (vibration analysis), displacement sensors, strain gauges, and the like can also be used to determine clot consistency and location to provide feedback and tailor treatment. In an implementation of a method, the modal response of the catheter body can be analyzed throughout treatment, for example, by an automated continuous measurement. A control response can be recorded once the catheter is in place adjacent a clot, but before initiation of aspiration. The control response recorded can take into account the specific conforming shape of the catheter body within the patient. Aspiration can be initiated and performed during which the modal response can be monitored. The catheter can be removed after the response recorded indicates clot advancement beyond the catheter tip.

Figure 11A:
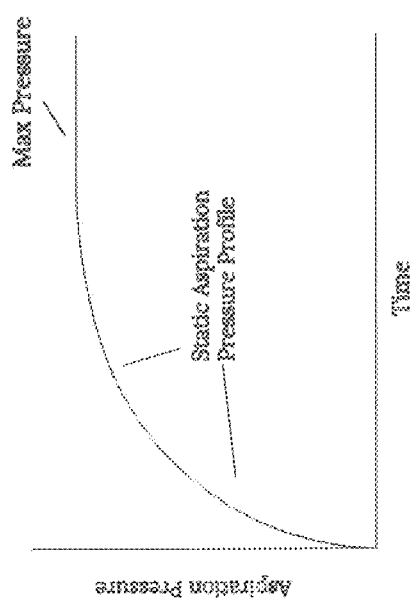
FIGS. 11A and 11B illustrate aspiration pressure over time for a static and a cyclic aspiration system, respectively.

FIG. 11A shows a static aspiration pressure profile. The vacuum source 505 is turned on at time=0, the vacuum pressure builds as air is evacuated from the pump body 505, canister 510, tubing 502, and catheter system 500. The aspiration pressure eventually reaches a maximum value after which the pressure is held static until either aspiration is stopped or the blockage is removed. This pressure profile can be modified through the use of the in-line valve 515, allowing the pressure to build up with the valve 515 to the catheter system 500 closed and then increase rapidly at the catheter tip as the valve 515 is opened. In each case, the pressure reaches a maximum and the curve is stable.

Figure 11B:
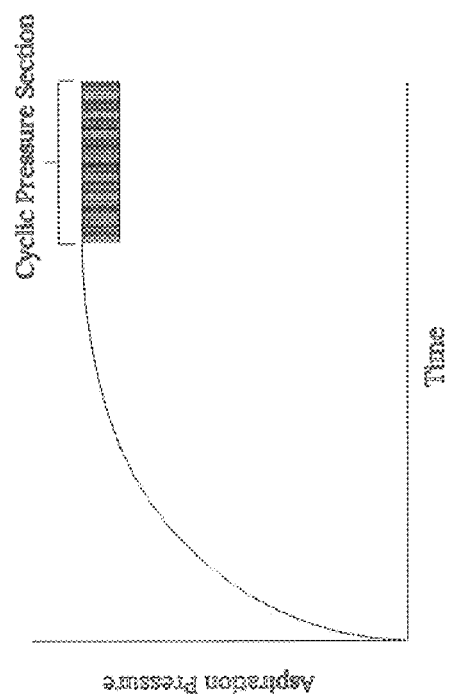

FIG. 11B shows a cyclic aspiration profile example. The aspiration pressure is allowed to build similar to the static aspiration pressure profile described above. However, once sufficient negative pressure is achieved, pressure cycling can begin. Cycling can be initiated during other points of the pressure curve including before, during, or after the plateau part of the pressure curve. For example, it may be beneficial to cycle the pressure during the building phase of the curve before the plateau is reached. The cycling mechanism may be used to modulate the aspiration pressure within the system such that the functional portion of the catheter system 500, for example the distal opening at the distal tip of a telescoping catheter, experiences significant changes in pressure. This is in contrast to a cycling mechanism that cycles pressure only within the proximal canister 510, which may be insufficient in manifesting significant pressure cycling at the functional portion of the catheter system 500. Pressure buffering within the canister 510 and pressure losses due to long lengths of the tubing 502 between the canister 510 and the distal tip of the catheter system 500 may contribute to poor transmission of pressure cycles to the catheter tip when the valve location is not placed in an optimal position. As the cyclic aspiration valve is moved closer to the catheter, the pressure drop per cycle at the catheter tip increases. Meaning, the pressure transfer to the distal tip improves thereby creating a greater magnitude of pressure drop at the catheter tip. Having the cycling mechanism (valve 515) as close to the proximal end of the catheter minimizes losses within the system and maximizes the pressure transfer at the distal tip.

In addition to optimizing the placement of the valve 515 in relation to the catheter, layers of pressure cycling can be utilized to further encourage clot ingestion. For example, using a cyclic aspiration pressure profile where the valve 515 is opened for between about 40 to 50 ms, then closed for between about 100 to 150 ms (Cycle 1), then opened for between about 5 to 10 ms, then closed for between about 100 to 150 ms (Cycle 2) and repeated for a total of between about 40 to 80 cycles after which static aspiration is initiated for between about 5 to 10 seconds to reestablish maximal aspiration pressure. This profile described above uses an average cyclic frequency of about 3 Hz. The valve 515 opening times above may be varied to optimize clot ingestion, for example, either of the valve 515 opening times may be varied to encourage clot ingestion or the static aspiration may be varied.

The cycling as well as the pressures applied during aspiration can vary depending on the phase of the procedure. A range of applied pressure and a range of frequencies can be used to assess and tune the cyclical minimum and maximum applied force inHg and frequency (Hz) during the "ingestion" phase of aspiration. The operator may decide to transition from the "ingestion" phase, for example if there is cessation of flow and evacuation of the embolus is determined not to be possible, to an "ADAPT" phase where the withdrawal of a presumably "corked" embolus would begin. In this phase, the operator may switch aspiration back to a maximum pressure static mode (e.g. 29 inHg) and hold pressure constant during withdrawal of the catheter corked with an embolus. By using a static pressure at this point, the embolus, presumably immobile, is compacted and as much hold is exerted on the embolus as possible. Both of these effects are desired to minimize the risk of the embolus fragmenting and embolizing distally during withdrawal.

The spined catheters described herein can transmit aspiration forces through a stepped aspiration column that includes the distal catheter inner diameter that steps up to the larger inner diameter of the more proximal access sheath. For example, a distal catheter having an 0.070" inner diameter (ID) can extend beyond the distal end of a sheath having an 0.088" inner diameter. The ID of the aspiration column can step up from 0.070" to 0.088". The much larger ID of the proximal aspiration column can change the transmission of forces to the embolus, especially under cyclic aspiration. In contrast, standard catheters undergo no step-up in inner diameter along the aspiration column. The fixed ID for the entire length in a standard catheter system results in a muted transmission of cycling aspiration forces between the maximum and minimum pressures where the walls of the catheter create resistance. The mean pressure may be transmitted to the open ended catheter tip, the fidelity of the sharp waves and the peaks and valleys of the cyclic pressure waveform would be diminished in a standard catheter system compared to that of a spined catheter system. The amplitude and the fidelity of the pressure waveform would be diminished in a standard catheter creating less of the desired fatiguing effect on the clot to fracture and break up the clot in order to evacuate it. Cyclic aspiration may also improve clot retrieval due to stretching the clot; reducing friction on the vessel wall by the clot; and/or other mechanisms besides clot material fatigue. Cyclic aspiration may also more effectively stress connections the clot has with the vessel wall thereby leading to easier retrieval of the clot.

The spined catheter creates a stepped aspiration column with the sheath such that the peaks and valleys of the cyclic aspiration are better transmitted to the distal tip. In the case of an 0.070" spined catheter, the aspiration column can step up to 0.088" at the sheath. In the case of nested catheters, an 0.070" spined catheter can telescope from an 0.088" spined catheter that can telescope from an 0.106" sheath. The much larger conduit proximal to the narrower 0.070" conduit more effectively transmits the amplitude and fidelity or sharpness of the pressure wave further down the column before the narrower 0.070" conduit is reached. This results in a more direct communication of the cyclic aspiration force to a point that represents the majority of the length of the aspiration column before narrowing to the smaller ID telescoping segment where the amplitude and fidelity of the aspiration wave diminishes, albeit to a lesser degree than the full length 0.070" catheter.

The emboli can be engulfed initially into the catheter tip during aspiration for stroke thrombectomy/embolectomy. The nature of the emboli varies widely. A softer, more "thrombotic" or "fresh" clot is generally friable and may dissociate into multiple fragments and evacuate in a matter of seconds through the thrombectomy catheter. If the clot is more "organized" or more like "chewing gum" in nature, the clot more commonly will lodge in the lumen of the thrombectomy catheter. The clot may not progress down the catheter or may progress very slowly at a certain velocity. Cycling aspiration enhances the movement of a slow moving clot through the catheter shaft by creating shearing and likely fragmentation thereby facilitating evacuation. With static or cyclic evacuation, a slow moving, organized embolus may take a matter of minutes to traverse a long catheter length. A stepped aspiration column can help to minimize the duration of embolus travel through the catheter. The majority of the length of the aspiration column will likely be the larger bore size in a system of spined catheters. The slowly traversing embolus will almost instantly evacuate at the transition to the step-up in inner diameter within the system (i.e. where the distal luminal portion ends and the proximal control element begins) once relieved of the side wall friction in the smaller inner diameter of the telescoping extension catheter. The time of evacuation will therefore be shortened compared to conventional, full length catheters as the embolus will traverse a much shorter distance at the slow pace before reaching the point of rapid evacuation into the pump canister or syringe barrel. The time of full evacuation is a key parameter to be optimized during a procedure. If the clot is fully engulfed within the catheter, but not traversing through the catheter quickly, the surgeon has little to no feedback. For example, the surgeon is unable to see that the clot is removed without the use of time-consuming imaging techniques. Another technique is to use the largest catheter sizes to maximize clot removal, however larger catheters may unnecessarily block restorative blood flow. Clots are more likely to be cleared completely and quickly using cyclic aspiration patterns described herein, and may be further enhanced through the use of a step-up in catheter diameter to expedite clot retrieval to reduce treatment time and decrease the time to reperfusion. Additionally, aspiration parameters can be tailored to different catheters with different physical and material properties. In an example, a catheter with a small diameter may be very flexible and exhibit unwanted lateral movement when subjected to large cyclic pressure differentials. Thus, the aspiration profile can be modified to both maximize pressure transmission to the catheter tip while minimizing unwanted catheter movement. In another example, a large-bore catheter may be able to efficiently transmit very large cyclic pressure differentials to the catheter tip. Thus, the aspiration profile can be changed to accommodate this new scenario. The cyclic aspiration system can incorporate a manual setting whereby certain aspiration profiles can be preprogrammed for generic catheter properties (e.g. "small" "medium" and "large-bore catheters"). Alternative or additionally, the cyclic aspiration system can incorporate a strain gauge or other detection mechanism (e.g. vibration sensor with or without vibration source, modal analysis, etc.) to automatically assess the compatibility of cyclic profiles and catheters being used. An additional detection element involving a strain gauge at the distal tip of the catheter can determine the relative position and speed of the clot in and around the catheter. For example, one or more strain gauges at the catheter tip can provide feedback informing a user that the clot was either fully engulfed or partially engulfed and, in either case, whether the clot was progressing up the catheter or stationary. The strain gauge can be fabricated in the wall of the catheter utilizing a wire reinforcement layer. For example, a portion of the wire reinforcement layer can be configured as a strain gauge. This information is beneficial to the surgeon who can make an informed decision about retracting the catheter or leaving it in place based on the readings. If a clot is partially-engulfed but progressing up the catheter, a user may conclude that continuing treatment is a good course of action. Alternatively, if the clot is fully-engulfed and not progressing, the user may conclude the catheter should be removed to fully extract the clot. In another example, if the clot is "corked," i.e. not fully engulfed but aspiration is not progressing the clot up the catheter, a surgeon may decide to remove the catheter corked with the clot while under static aspiration.

Delivery of larger bore catheters with maximum inner diameter aided with the catheter advancement element described herein to reach the face of the clot will facilitate complete engulfment using cyclic aspiration. The catheter best suited to remove an embolus is one that approximates the size of the vessel within which the embolus is found. An additional benefit of choosing a catheter that approximates the size of the vessel is that the distal tip of the catheter will be more centered within the lumen of the vessel. When aspiration is performed, the embolus is positioned more in-line with the bore of the catheter for improved retrieval during aspiration. The catheter advancement elements described herein ensure these larger bore catheters having a size that approximates the size of the vessel can be advanced as far distal as possible to the face of the clot.

The aspiration system described herein has the capability of "shifting gears" during a procedure. The aspiration system can include a variety of aspiration settings optimized for each diameter catheter to be advanced. As an example, a nested system of spined catheters can include an 0.070" spined catheter sleeved inside of an 0.088" spined catheter and be positioned at the face of an embolus. The two catheters can be delivered to the face of the embolus (e.g. in the M1 segment of the middle cerebral artery). The operator can initiate aspiration embolectomy by selecting a setting for cyclic aspiration parameters for the 0.070" system. The aspiration system can be set to an "070 INGEST MODE" to apply cyclic aspiration through the tip of the 0.070" catheter for a period of minutes to allow for complete ingestion and restoration of complete flow. The operator may choose, based upon clinical judgment, that ingestion will not occur and choose to withdraw the 0.070" spined catheter. The operator can switch to a "WITHDRAWAL MODE," which can be a high-pressure static aspiration (e.g. 29 inHg). Upon switching to the "WITHDRAWAL MODE," the operator may wait a period to achieve a steady state of embolus compression and "hold" before the operator then withdraws the 0.070" spined catheter out of the proximal RHV with continuous high pressure applied to the presumably "corked" emboli. This can minimize the risk of dislodging the embolus from the distal tip of the catheter being withdrawn. Aspiration forces in the "070 INGEST MODE" and the "WITHDRAWAL MODE" may be applied to the side arm of the RHV creating a single point of aspiration for both the 0.070" spined catheter removal and later for removal of the 0.088" spined catheter as well as for clearing the sheath with aspiration as a final cleansing step.

Upon removal of the 0.070" spined catheter and the RHV closed, the operator may initiate the "088 INGEST mode" cyclic setting and apply immediate ingestion-inducing cyclic aspiration via the 0.088" distal tip. The "088 INGEST MODE" may be different from the "070 INGEST MODE". The different caliber aspiration columns may need different cyclic forces, mediums (e.g. air, water), and frequencies. The tuning of the cyclic aspiration parameters may be focused on settings that facilitate creeping relentless movement of the most challenging embolic material likely to be faced in acute stroke cases and adjusted for the smallest caliber distal extension of the spined catheter-based aspiration column. In the setting of an 0.070" spined catheter, for example, the settings can be tuned to the 0.070" catheter element.

The likelihood of ingestion is much higher with a larger bore catheter that approximates the size of the artery. However, if withdrawal were to be contemplated and free flow of blood into the canister of the pump not realized, an operator may switch to "WITHDRAWAL MODE" and remove the 0.088 catheter similarly if it is presumed to be corked. The combination of a larger bore catheter and cyclic aspiration may increase the likelihood of complete engulfment and clearance of the emboli into the canister or syringe barrel. A user can convert current practice with aspiration-based stroked intervention from primarily corking emboli onto the catheter to one where the clot is completely evacuated through the catheter. The system thus avoids the drawbacks of slow withdrawal of embolus captured on the distal tip of the catheter that creates risk of distal embolization or off-target embolization into a separate new region that could lead to new damage of brain tissue.

The methods described above may be used in combination with other devices such as a stent retriever. The operator may choose to use a stent retriever and the cyclic and/or static aspiration applied as the stent retriever is withdrawn into either the 0.070" or the 0.088" spined catheter. Some operators may withdraw the stent retriever into the large-bore catheter at the site of occlusion (so-called "Solumbra" technique as per Spiotta et al., Endovascular Today 2016; 15(2):68-70). If during stent retriever removal a cessation of flow occurs, the sequence of a cyclic "INGEST" mode as defined by the catheter dimensions should be considered to enhance fragmentation and reestablishment of distal flow at the catheter tip, which imparts protection from distal embolization should flow be restored. If the operator continues to withdraw the stent retriever with the large bore catheter still in the distal position this can be continued with cyclic INGEST mode with or without cessation of flow. Should the stent retriever be completely withdrawn and cessation of flow remain an attempt to engulf and evacuate the clot can continue in the INGEST mode. If it is assumed that the corked situation is present with the embolus and a decision is made to withdraw, subsequent catheter withdrawals with cessation of flow may be performed under the "WITHDRAWAL MODE" so static maximum pressure is applied presuming that the stent retriever left behind embolic material that created a corked catheter in an attempt to engulf the embolus on its own or resort to an ADAPT-type of withdrawal.

Other operators may withdraw the embolus with the stent retriever remaining beyond the large-bore catheter given fear of shearing off the embolus with withdrawal into the mouth of the catheter. In this setting, ideally, the embolus is corked on the catheter tip and it may be treated as if is a corked catheter with various modes of aspiration. Any catheter withdrawal should be done with maximum static pressure applied in a WITHDRAWAL MODE.

Materials

One or more components of the catheters described herein may include or be made from a variety of materials including one or more of a metal, metal alloy, polymer, a metal-polymer composite, ceramics, hydrophilic polymers, polyacrylamide, polyethers, polyamides, polyethylenes, polyurethanes, copolymers thereof, polyvinyl chloride (PVC), PEO, PEO-impregnated polyurethanes such as Hydrothane, Tecophilic polyurethane, Tecothane, PEO soft segmented polyurethane blended with Tecoflex, thermoplastic starch, PVP, and combinations thereof, and the like, or other suitable materials.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material and as described elsewhere herein.

Inner liner materials of the catheters described herein can include low friction polymers such as PTFE (polytetrafluoroethylene) or FEP (fluorinated ethylene propylene), PTFE with polyurethane layer (Tecoflex). Reinforcement layer materials of the catheters described herein can be incorporated to provide mechanical integrity for applying torque and/or to prevent flattening or kinking such as metals including stainless steel, Nitinol, Nitinol braid, helical ribbon, helical wire, cut stainless steel, or the like, or stiff polymers such as PEEK. Reinforcement fiber materials of the catheters described herein can include various high tenacity polymers like Kevlar, polyester, meta-para-aramide, PEEK, single fiber, multi-fiber bundles, high tensile strength polymers, metals, or alloys, and the like. Outer jacket materials of the catheters described herein can provide mechanical integrity and can be contracted of a variety of materials such as polyethylene, polyurethane, PEBAX, nylon, Tecothane, and the like. Other coating materials of the catheters described herein include paralene, Teflon, silicone, polyimide-polytetrafluoroetheylene, and the like. The inner liner may further include different surface finishes, such as dimples, bumps, ridges, troughs. The surface finishes may be randomly disposed, linearly disposed, spirally disposed, or otherwise disposed using a specific pattern along the length of the catheter. It is further contemplated that the inner liner may include a mixture of different surface finishes, for example, one section may have dimples, another section may have troughs, etc. Additionally, the surface finish may be incorporated along the entire length of the catheter or only in sections of the catheter. It is also contemplated that the inner liner may further include an electrosprayed layer, whereby materials could be incorporated into the inner liner. Examples of materials can include low friction materials as described above. Alternatively, the electrosprayed or electrospun layer may incorporate a beneficial agent that becomes free from the coating when exposed to blood, or to compression from a clot, for example, the beneficial agent may be a tissue plasminogen activator (tPA) or heparin encased in alginate.

Implementations describe catheters and delivery systems and methods to deliver catheters to target anatomies. However, while some implementations are described with specific regard to delivering catheters to a target vessel of a neurovascular anatomy such as a cerebral vessel, the implementations are not so limited and certain implementations may also be applicable to other uses. For example, the catheters can be adapted for delivery to different neuroanatomies, such as subclavian, vertebral, carotid vessels as well as to the coronary anatomy or peripheral vascular anatomy, to name only a few possible applications. Although the systems described herein are described as being useful for treating a particular condition or pathology, that the condition or pathology being treated may vary and are not intended to be limiting. Use of the terms "embolus," "embolic," "emboli," "thrombus," "occlusion," "clot", etc. that relate to a target for treatment using the devices described herein are not intended to be limiting. The terms may be used interchangeably and can include, but are not limited to a blood clot, air bubble, small fatty deposit, or other object carried within the bloodstream to a distant site or formed at a location in a vessel. The terms may be used interchangeably herein to refer to something that can cause a partial or full occlusion of blood flow through or within the vessel.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detail in order to not unnecessarily obscure the description. Reference throughout this specification to "one embodiment," "an embodiment," "one implementation," "an implementation," or the like, means that a particular feature, structure, configuration, or characteristic described is included in at least one embodiment or implementation. Thus, the appearance of the phrase "one embodiment," "an embodiment," "one implementation," "an implementation," or the like, in various places throughout this specification are not necessarily referring to the same embodiment or implementation. Furthermore, the particular features, structures, configurations, or characteristics may be combined in any suitable manner in one or more implementations.

The use of relative terms throughout the description may denote a relative position or direction. For example, "distal" may indicate a first direction away from a reference point. Similarly, "proximal" may indicate a location in a second direction opposite to the first direction. The reference point used herein may be the operator such that the terms "proximal" and "distal" are in reference to an operator using the device. A region of the device that is closer to an operator may be described herein as "proximal" and a region of the device that is further away from an operator may be described herein as "distal". Similarly, the terms "proximal" and "distal" may also be used herein to refer to anatomical locations of a patient from the perspective of an operator or from the perspective of an entry point or along a path of insertion from the entry point of the system. As such, a location that is proximal may mean a location in the patient that is closer to an entry point of the device along a path of insertion towards a target and a location that is distal may mean a location in a patient that is further away from an entry point of the device along a path of insertion towards the target location. However, such terms are provided to establish relative frames of reference, and are not intended to limit the use or orientation of the catheters and/or delivery systems to a specific configuration described in the various implementations.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

The catheter system disclosed herein may be packaged together in a single package, where the catheters and catheter advancement element are packaged in a coil tube. The finished package would be sterilized using sterilization methods such as Ethylene oxide or radiation and labeled and boxed. Instructions for use may also be provided in-box or through an internet link printed on the label.

What is claimed is:

1. A method of performing a medical procedure in a cerebral vessel, the method comprising:
  inserting a catheter system into a blood vessel, the catheter system comprising:
    a guide sheath comprising a distal end, a proximal end, a lumen extending between the distal end and the proximal end, and a rotating hemostatic valve disposed on the proximal end;
    a catheter comprising a proximal end, a distal end, and a lumen, wherein an outer diameter of the catheter is sized to be slidably disposed within the lumen of the guide sheath through the rotating hemostatic valve;
    a vacuum source configured to be placed in fluid communication with the lumen extending through the catheter; and
    a second valve positioned between the vacuum source and the catheter;
  advancing the guide sheath into an internal carotid artery;
  advancing the catheter within the lumen of the guide sheath until the distal end of the catheter is adjacent to an embolus in the cerebral vessel;
  activating the vacuum source to create a vacuum in the lumen of the catheter; and
  cyclically controlling the vacuum applied with the second valve, wherein the vacuum is cyclically controlled by opening the second valve for a first time period, closing the second valve for a second time period longer than the first time period, opening the second valve for a third time period shorter than the first time period, then closing the second valve for a fourth time period greater than the first time period, repeating for at least 40 cycles.

2. The method according to claim 1, further comprising applying static aspiration forces for between about 5 to 10 seconds to reestablish maximal aspiration pressure after completing the cycles.

3. The method according to claim 2, wherein the vacuum source comprises a pump, and the pump comprises a programmable pump motor controller.

4. The method according to claim 1, further comprising providing a pressure differential between the vacuum source, the distal end of the catheter, and an external environment using the second valve to control patency.

5. The method according to claim 4, further comprising temporarily closing the second valve to the external environment causing the vacuum source to create a vacuum at the distal end of the catheter, and subsequently opening the second valve to the external environment diminishing the vacuum applied at the distal end of the catheter.

6. The method according to claim 1, wherein the second valve is a three-way valve.

7. The method according to claim 1, wherein the second valve is pneumatic, electromechanical, or mechanical.

8. The method according to claim 1, wherein the second valve is a pneumatic valve located on a vacuum line near a proximal section bridging a proximal canister and the catheter.

9. The method according to claim 8, wherein the second valve is located inside, attached to, or near an outlet from the proximal canister.

10. The method according to claim 8, wherein the second valve is attached to the proximal end of the guide sheath.

11. The method according to claim 1, wherein the second valve comprises a plurality of valves serially coupled in fluid communication, wherein each of the plurality of valves is controlled or programmed to cycle at different frequencies.

12. The method according to claim 1, further comprising electronically controlling the second valve with a microcontroller relay system to create a cyclic pressure environment at the distal end of the catheter.

13. The method according to claim 12, wherein the microcontroller relay system alternately opens and closes a connection between the lumen of the catheter and a second environment.

14. The method according to claim 13, wherein the second environment comprises a controlled pressure chamber or ambient atmosphere.

15. The method according to claim 1, wherein the first time period is between about 40 to 50 ms.

16. The method according to claim 1, wherein the second time period is between about 100 to 150 ms.

17. The method according to claim 1, wherein the third time period is between about 5 to 10 ms.

18. The method according to claim 1, wherein the fourth time period is between about 100 to 150 ms.

19. The method according to claim 1, wherein the cycles are repeated up to 80 cycles.

* * * * *